(12) United States Patent
Nitin et al.

(10) Patent No.: US 10,864,168 B2
(45) Date of Patent: Dec. 15, 2020

(54) BIOACTIVE DELIVERY VEHICLES

(71) Applicant: The Regents of the University of California, Oakland, CA (US)

(72) Inventors: Nitin Nitin, Davis, CA (US); Stephen Young, Davis, CA (US); Jean Vandergheynst, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 240 days.

(21) Appl. No.: 15/521,253

(22) PCT Filed: Oct. 28, 2015

(86) PCT No.: PCT/US2015/057805
§ 371 (c)(1),
(2) Date: Apr. 21, 2017

(87) PCT Pub. No.: WO2016/069740
PCT Pub. Date: May 6, 2016

(65) Prior Publication Data
US 2018/0296490 A1    Oct. 18, 2018

Related U.S. Application Data

(60) Provisional application No. 62/072,394, filed on Oct. 29, 2014.

(51) Int. Cl.
| | | |
|---|---|---|
| A61K 9/50 | (2006.01) | |
| A61K 36/05 | (2006.01) | |
| A61K 38/28 | (2006.01) | |
| A61K 31/07 | (2006.01) | |
| A61K 31/12 | (2006.01) | |
| A61K 31/352 | (2006.01) | |
| A61K 31/353 | (2006.01) | |
| A23P 10/35 | (2016.01) | |
| A61K 8/11 | (2006.01) | |
| A61K 8/99 | (2017.01) | |
| A61Q 19/00 | (2006.01) | |
| A61K 35/745 | (2015.01) | |
| A61K 35/741 | (2015.01) | |
| A61K 35/747 | (2015.01) | |
| A61K 35/20 | (2006.01) | |
| A23L 27/00 | (2016.01) | |
| A61K 8/9722 | (2017.01) | |
| A61K 8/9728 | (2017.01) | |
| A61K 8/9789 | (2017.01) | |
| A61K 8/9794 | (2017.01) | |
| A23L 33/14 | (2016.01) | |
| A23L 33/135 | (2016.01) | |
| A61P 1/00 | (2006.01) | |
| A61P 29/00 | (2006.01) | |
| A23L 2/52 | (2006.01) | |
| A61K 35/74 | (2015.01) | |
| A61K 36/06 | (2006.01) | |
| A61K 36/064 | (2006.01) | |
| A61K 35/00 | (2006.01) | |

(52) U.S. Cl.
CPC .............. *A61K 9/5089* (2013.01); *A23L 2/52* (2013.01); *A23L 27/72* (2016.08); *A23L 33/135* (2016.08); *A23L 33/14* (2016.08); *A23P 10/35* (2016.08); *A61K 8/11* (2013.01); *A61K 8/9722* (2017.08); *A61K 8/9728* (2017.08); *A61K 8/9789* (2017.08); *A61K 8/9794* (2017.08); *A61K 8/99* (2013.01); *A61K 9/5068* (2013.01); *A61K 31/07* (2013.01); *A61K 31/12* (2013.01); *A61K 31/352* (2013.01); *A61K 31/353* (2013.01); *A61K 35/20* (2013.01); *A61K 35/74* (2013.01); *A61K 35/741* (2013.01); *A61K 35/745* (2013.01); *A61K 35/747* (2013.01); *A61K 36/05* (2013.01); *A61K 36/06* (2013.01); *A61K 36/064* (2013.01); *A61K 38/28* (2013.01); *A61P 1/00* (2018.01); *A61P 29/00* (2018.01); *A61Q 19/00* (2013.01); *A23V 2002/00* (2013.01); *A61K 2035/11* (2013.01); *A61K 2800/56* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,364,631 A | 11/1994 | Janoff | |
| 5,580,575 A * | 12/1996 | Unger | .................... A61K 9/127 424/450 |
| 2008/0044464 A1 | 2/2008 | Tardi | |
| 2010/0297222 A1 | 11/2010 | Kanaya | |

FOREIGN PATENT DOCUMENTS

| | | |
|---|---|---|
| EP | 0453316 A1 | 10/1991 |
| EP | 1454534 A1 | 9/2004 |
| WO | 8702253 | 4/1987 |

(Continued)

OTHER PUBLICATIONS

IB WIPO, International Preliminary Report on Patentability dated May 2, 2017, related PCT international application No. PCT/US2015/057805, pp. 1-6, claims examined, pp. 7-19.

(Continued)

*Primary Examiner* — Blaine Lankford
(74) *Attorney, Agent, or Firm* — O'banion & Ritchey LLP; John P. O'banion

(57) ABSTRACT

Provided are lipid membrane microcapsules encapsulating or containing bioactives, and methods of production and use.

19 Claims, 19 Drawing Sheets

(56) References Cited

FOREIGN PATENT DOCUMENTS

| WO | WO-8702253 A1 * | 4/1987 | ........... A61K 9/1277 |
|---|---|---|---|
| WO | 0069440 A2 | 11/2000 | |
| WO | 0069440 A3 | 11/2000 | |
| WO | 2005102508 A1 | 11/2005 | |
| WO | 2016069740 A1 | 5/2016 | |

OTHER PUBLICATIONS

ISA US, International Search Report dated Jan. 14, 2016, related PCT international application No. PCT/US2015/057805, pp. 1-3, claims searched, pp. 4-17.

Young, Stephen et al., "Vacuum facilitated infusion of bioactives into yeast microcarriers: Evaluation of a novel encapsulation approach", Food Fesearch International 100 (2017) pp. 100-112, published online Aug. 2, 2017.

European Patent Office (EPO), Communication (extended European search report) dated May 25, 2018, related European patent application No. 15854249.8, pp. 1-8, claims searched, pp. 9-16.

European Patent Office (EPO), Communication pursuant to Article 94(3) EPC dated Nov. 4, 2019, related European patent application No. 15854249.8, pp. 1-8, claims examined, pp. 9-22.

* cited by examiner

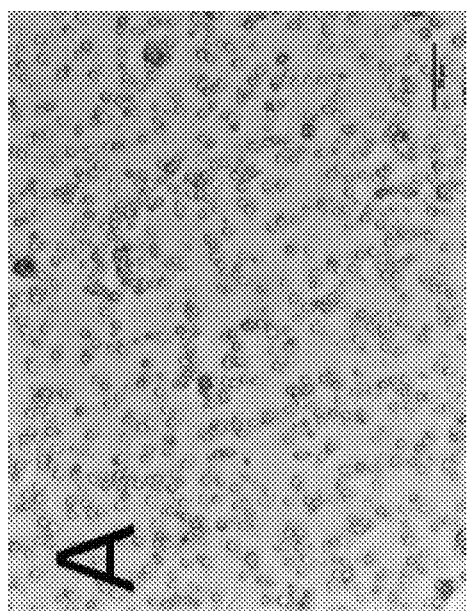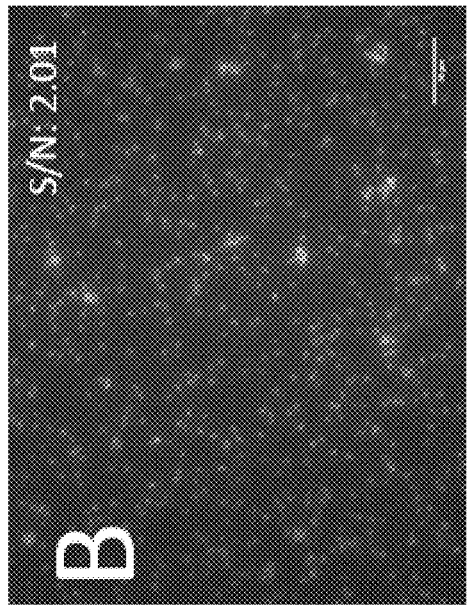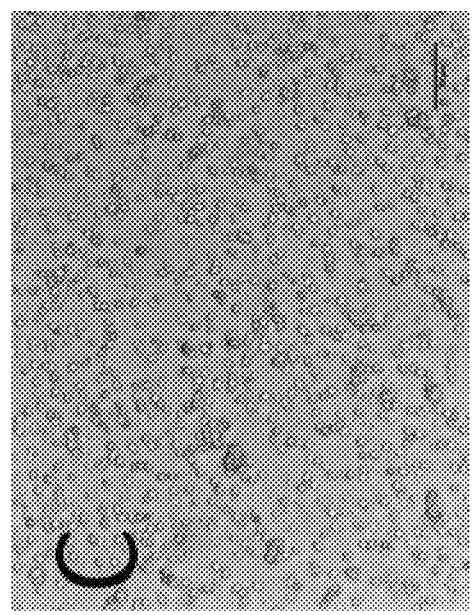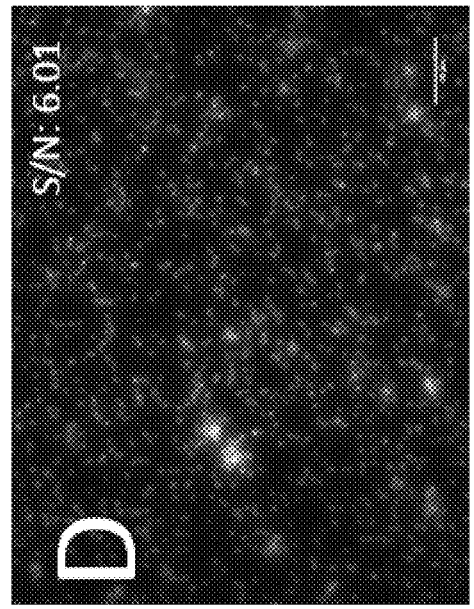
Fig. 2

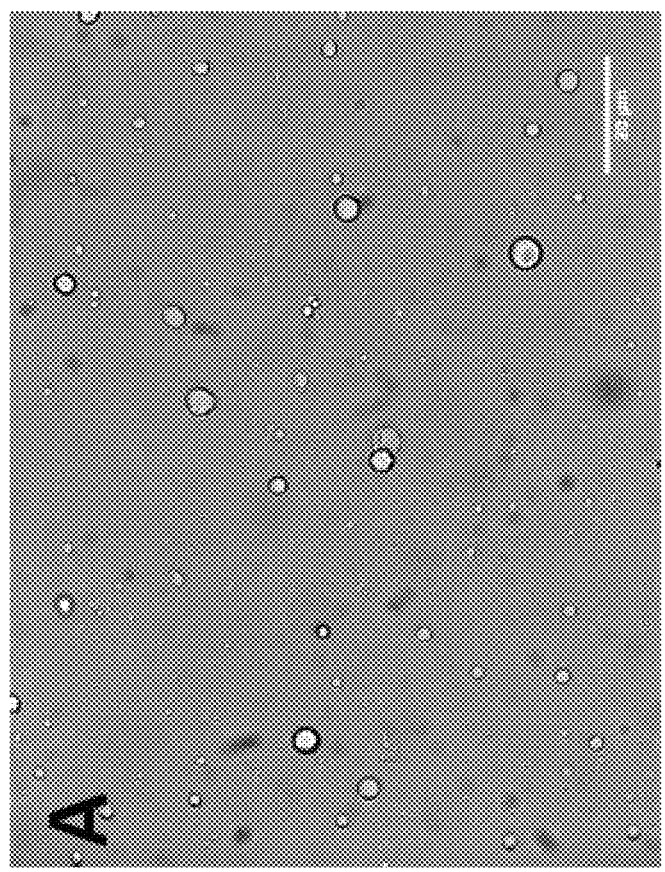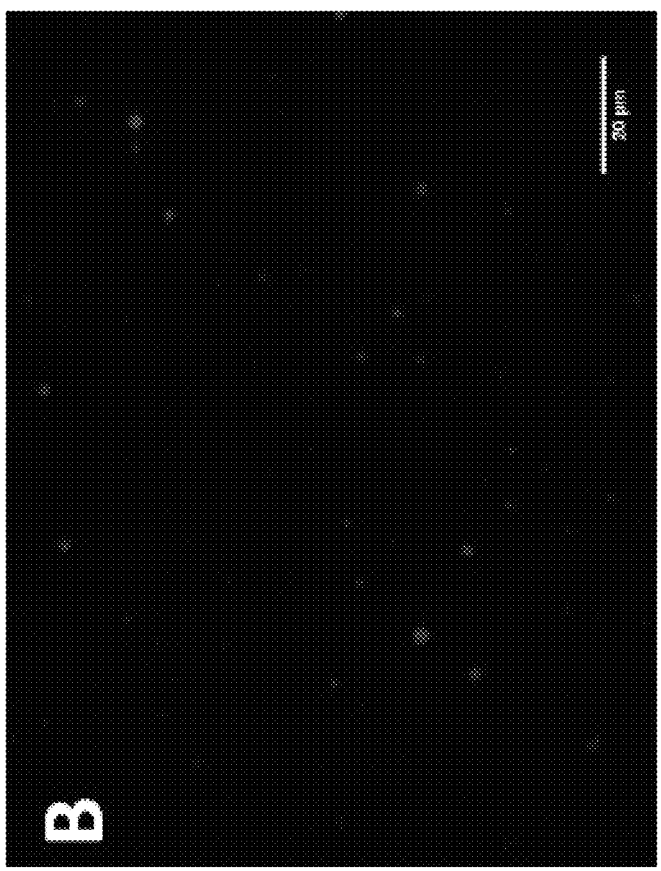
Fig. 9

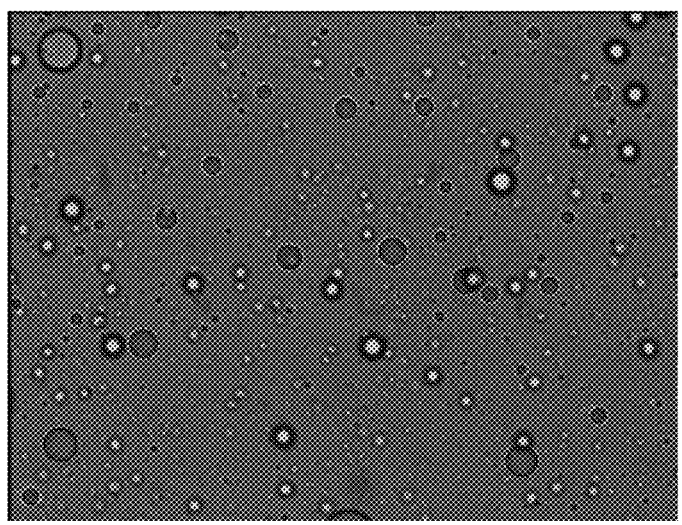
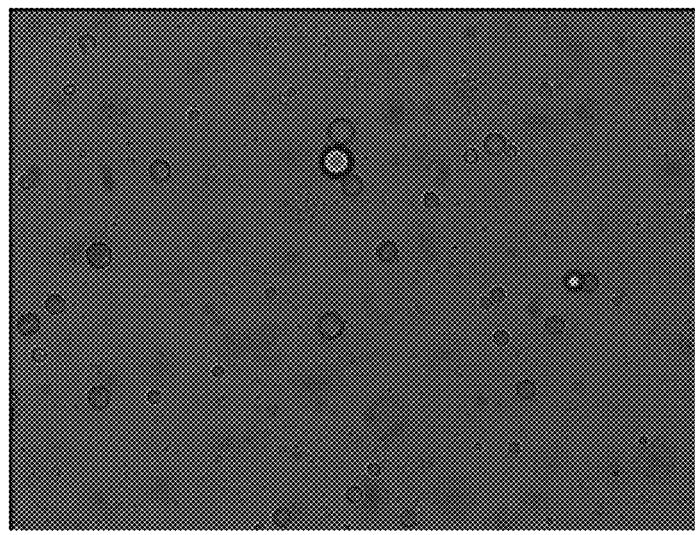
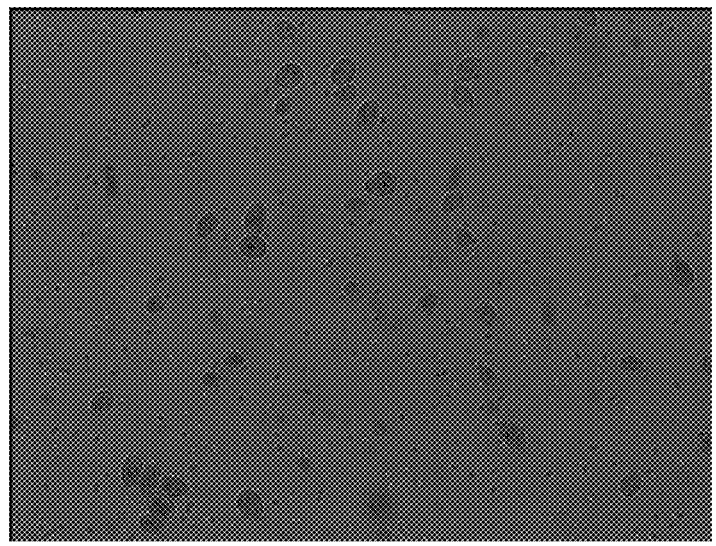
Fig. 14A-C

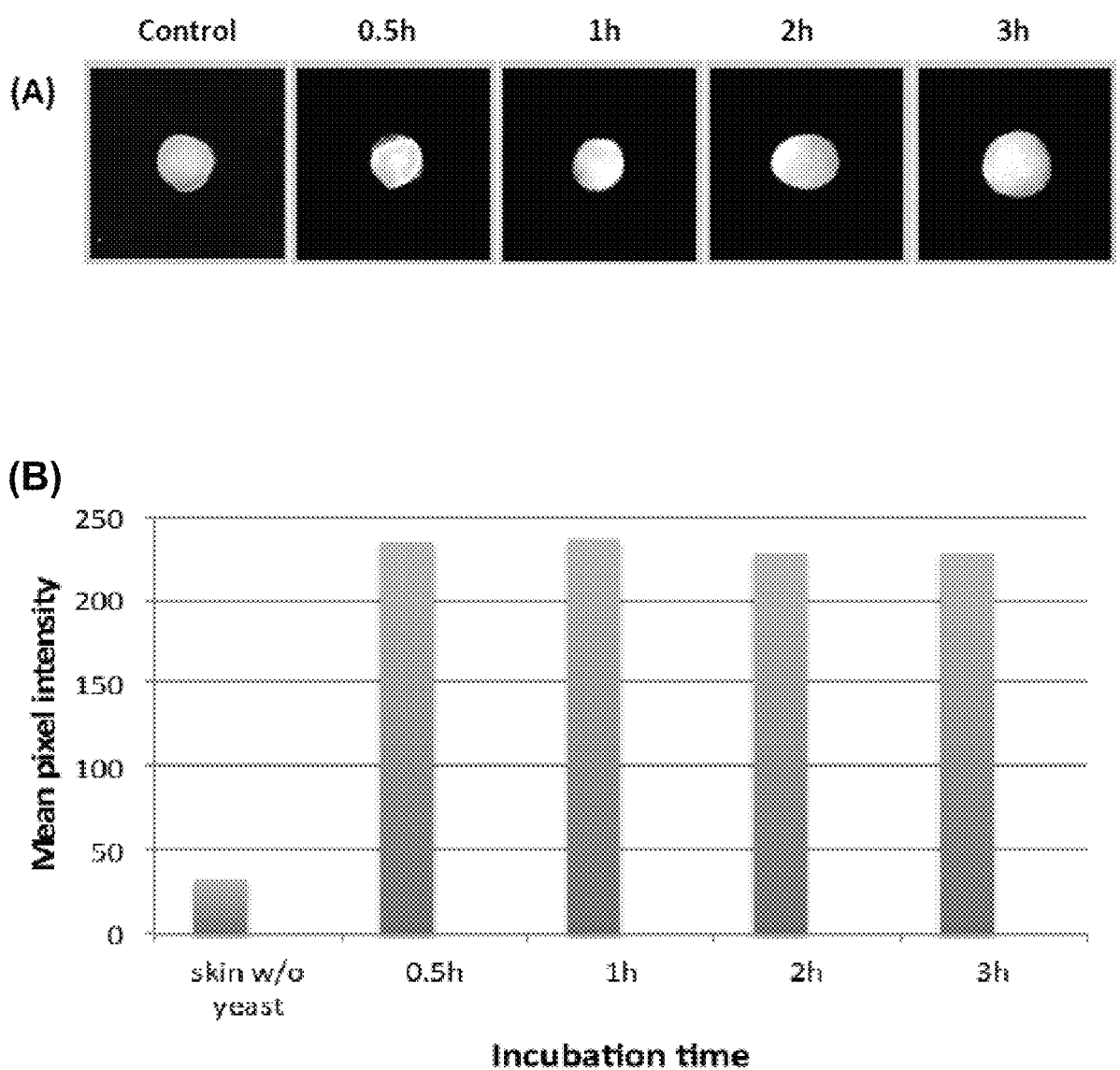
Fig. 15A-B

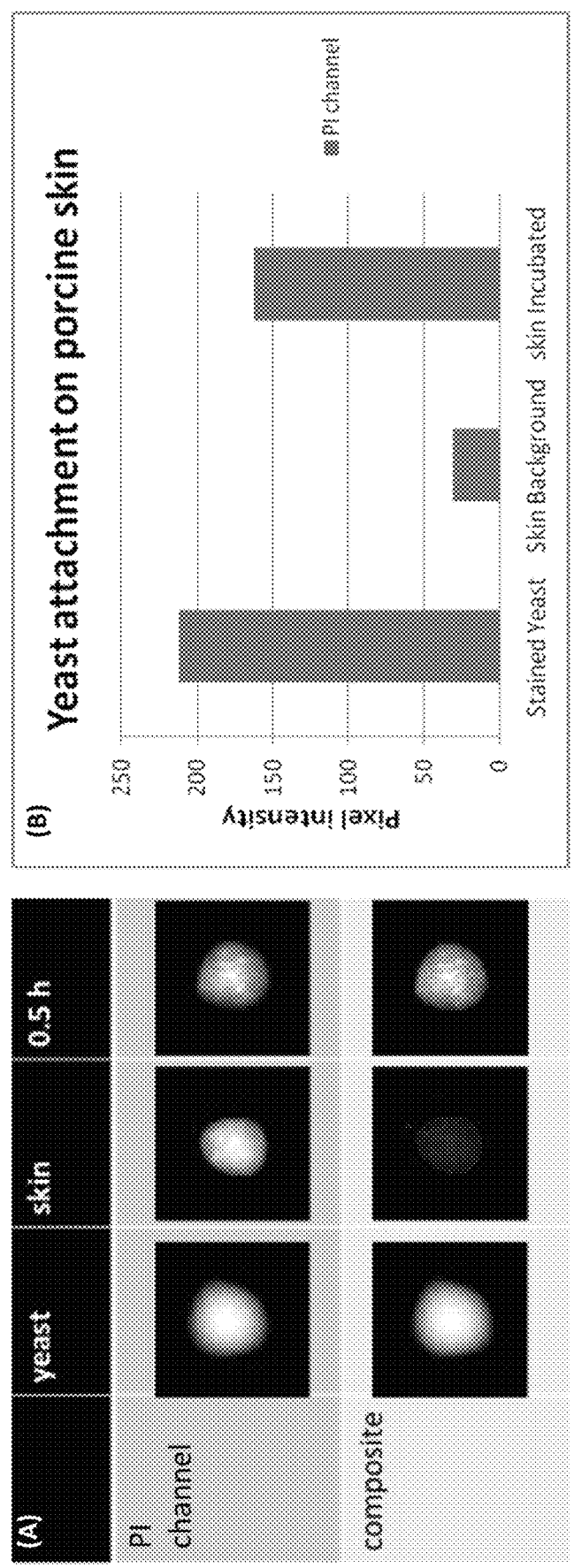
Fig. 16A-B

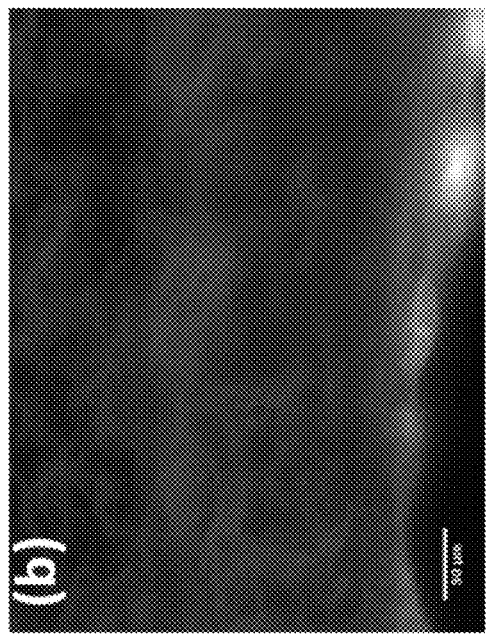
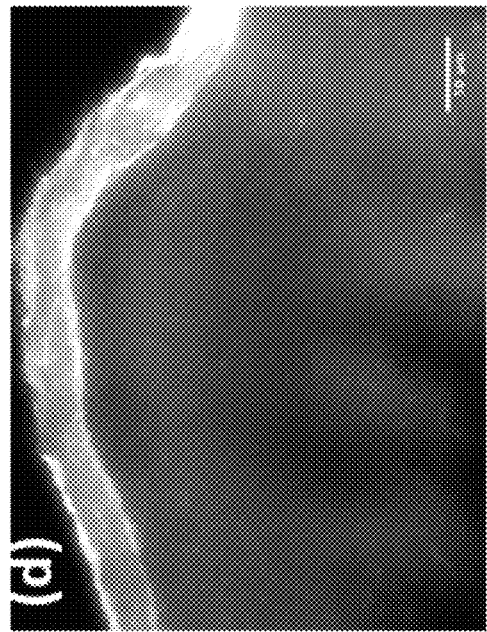
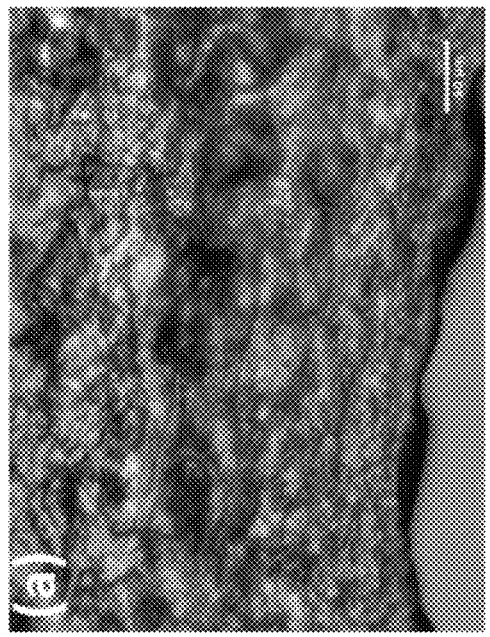
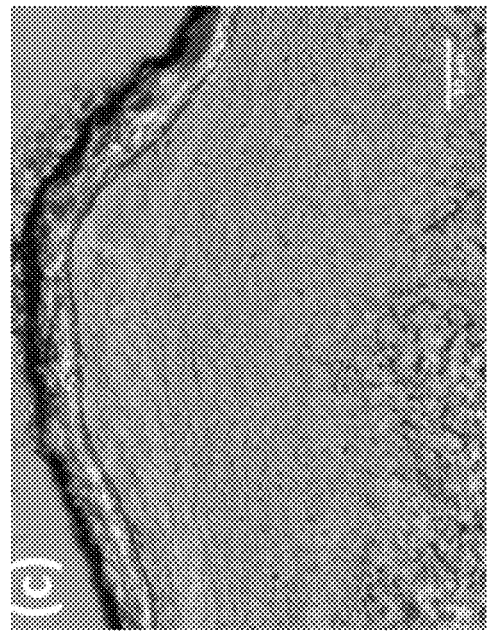
Fig. 17A-D

BIOACTIVE DELIVERY VEHICLES

CROSS-REFERENCE TO RELATED APPLICATIONS

This application is a U.S. national phase of Intl. Application No. PCT/US2015/057805, filed on Oct. 28, 2015, which claims the benefit under 35 U.S.C. 119(e) of U.S. Provisional Patent Application No. 62/072,394, filed on Oct. 29, 2014, which are hereby incorporated herein by reference in their entireties for all purposes.

FIELD

Provided are lipid membrane microcapsules encapsulating or containing bioactives, and methods of production and use.

BACKGROUND

Oxidation of bioactives both during food processing and storage is one of the key factors that limit incorporation of bioactives in food products and the shelf-life of bioactive enriched food materials (Emin, et al., *Lwt-Food Science and Technology* (2012) 48(2): 302-307; Bricarello, et al., *Soft Matter* (2012) 8(43):11144-11151; Chandler, et al., *Agro Food Industry Hi-Tech*, (2010) 21(5):24-28). The leading approaches for reducing oxidation in processed food systems include: chelation of metal ions using EDTA (Ethylenediaminetetraacetic acid) (Qian, et al., *Food Chemistry*, (2012) 135(3): 1036-1043; Guzun-Cojocaru, et al., *Food Chemistry*, (2011) 125(2):326-333; Guzun-Cojocaru, et al, *Food Hydrocolloids*, (2010) 24(4):364-373; Alamed, et al., *Food Chemistry*, (2006) 95(4):585-590), use of sacrificial antioxidants (Choe, et al., *Comprehensive Reviews in Food Science and Food Safety*, (2009) 8(4):345-358) and a combination of both these approaches in micro and nanoencapsulation methods (Guzun-Cojocaru, et al., supra; Alamed, et al., supra; Bou, R., et al., *European Journal of Lipid Science and Technology*, (2011) 113(6):724-729; Jacobsen, et al., *Trends in Food Science & Technology*, (2008) 19(2):76-93). In spite of significant efforts, oxidative stability of bioactives in processed food systems remains suboptimal (Charoen, et al., *Food Chemistry*, (2012) 131(4): 1340-1346; Meynier, et al., *Food Chemistry*, (2014) 153:94-100; Gomez-Estaca, et al., *Lwt-Food Science and Technology*, (2011) 44(6):1517-1524; Pedrosa, et al., *Ciencia E Agrotecnologia*, (2011) 35(2):404-409; Silva, et al., *Food Chemistry*, (2010) 121(4): 1177-1187; Bustos, et al., *Journal of Food Engineering*, (2003) 56(2-3):289-293). Current approaches for reducing oxidation of bioactives add significant cost to food formulations, often have stringent regulatory requirements (FDA requirements for EDTA levels in foods) and are generally associated with negative consumer perception of the processed food (Cheftel, *Advances in Food Protection: Focus on Food Safety and Defense*, (2011): p. 223-254).

Limited Shelf Life of Bioactive Compounds in Food and the Role of Food Additives Loss of food products due to limited shelf-life of the most susceptible ingredients, such as bioactive lipids and antioxidants, is the leading cause of food waste in the United States (Eriksson, et al., *Resources Conservation and Recycling*, (2014) 83:44-52; Pushkala, et al., *Innovative Food Science & Emerging Technologies*, (2012) 16:11-20; Taoukis, Case Studies in Novel Food Processing Technologies: Innovations in Processing, Packaging, and Predictive Modelling, (2010) 197:351-366). Ingredients such as lipids, vitamins and bioactives are often lost to oxidation incurred either during processing or during storage (Fukumoto, et al., *Journal of Agricultural and Food Chemistry*, (2000) 48(8): 3597-3604). Oxidation reactions impact quality of the food by inducing rapid development of off-flavors and deterioration of nutrients. The food industry has, therefore, explored various food additives to mitigate product loss and food waste due to oxidation. One such approach relies upon the use of synthetic antioxidants such as TBHQ (tertiary butylhydroquinone) and BHT (butylated hydroxyquinone). The use of such compounds in food, pharmaceutical and cosmetic systems dates back to the 1940's and 1950's. However, there is growing demand for processed foods without these synthetic food additives due to their perceived and potential health hazards (Botterweck, et al., *Food and Chemical Toxicology*, (2000) 38(7):599-605). Furthermore, the level of these synthetic antioxidants in food is highly regulated by the FDA due to safety concerns. In response to this trend, the food industry has sought to use natural compounds such as tocopherols (vitamin E), flavonoids and phenol antioxidants. Natural antioxidants, however, are significantly more expensive and, in some cases, these natural antioxidants can function as pro-oxidants in the food matrix, further enhancing the degradation of bioactives (Fukumoto, et al., supra).

In addition to the use of sacrificial antioxidants, the food industry has utilized chelators, specifically EDTA (ethylenediaminetetraacetic acid), which sequesters metal ions, particularly iron. As one of the most abundant minerals in the soil, iron is of particular concern as both common forms $Fe^{2+}$ and $Fe^{3+}$, due to their redox properties, initiate oxidation in foods (Alamed, et al., *Food Chemistry*, (2006) 95(4):585-590). However, as with synthetic antioxidants, EDTA use must be regulated and the allowed amounts added to food products are low (25-500 ppm), depending on the food system (on the internet at fda.gov/food/ingredientspackaginglabeling/foodadditivesingredients/ucm091048.htm). Moreover, chelators nonspecifically bind to most trace metals ions such as $Ca^{2+}$ and $Mg^{2+}$ that are necessary for adequate nutrition (Bothwell, et al., *International Journal for Vitamin and Nutrition Research*, (2004) 74(6):421-434).

Challenges with the Current Micro and Nanoencapsulation Approaches

Micro and nanoencapsulation are common approaches used in food products to enhance functional and sensory properties of diverse food products (Kaya-Celiker, et al., *Food Engineering Reviews*, (2012) 4(2): 114-123; McClements, et al., *Critical Reviews in Food Science and Nutrition*, (2009) 49(6):577-606; Sagalowicz, et al., *Current Opinion in Colloid & Interface Science*, (2010) 15(1-2):61-72; Taneja, et al., Challenges for the Delivery of Long-Chain n-3 Fatty Acids in Functional Foods, in Annual Review of Food Science and Technology, Vol. 3, M. P. Doyle and T. R. Klaenhammer, Editors. 2012. p. 105-123). Reactive oxygen species (ROS)-induced oxidative degradation of encapsulated bioactive compounds, such as omega-3 oils and vitamin E, is a major food quality issue that limits shelf life and sustainability of food products (Kaya-Celiker, et al., supra; Sagalowicz, et al., supra; Taneja, et al., supra; Coupland, et al., *Trends in Food Science & Technology*, (1996) 7(3):83-91; Gasperlin, et al., *European Journal of Pharmaceutical Sciences*, (2003) 19(4):181-189). Oxidation challenges in encapsulated systems are significantly exacerbated due to the large surface area of micron and sub-micron scale droplets and particles, abundant presence of metal ions in aqueous environments and rapid diffusion of oxygen from ambient air (Sagalowicz, et al., supra; Kanner, Metals and food oxidation, in Oxidation in Foods and Beverages and Antioxidant Applications, Vol 1: Understanding Mechanisms of Oxidation and Antioxidant Activity, E. A. Decker, R. J. Elias, and D. J. McClements, Editors. 2011. p. 36-56; Lee, et al., *Journal of Agricultural and Food Chemistry*, (2011) 59(11): 6271-6276; Nitin, et al., *Journal of Food Engineering*, (2011) 103(1): 14-20; Tikekar, et al., *Food Research International*, (2011) 44(1): 139-145). Depending on the encapsulation system, the initiation step of free radical generation can be triggered by many factors such as the presence of metal impurities, exposure to light, and high temperatures (Gasperlin, et al., supra; Decker, et al., *Journal of Agricultural and Food Chemistry*, (2000) 48(2): 213-219; Jacobsen, et al., *European Journal of Lipid Science and Technology*, (2008) 110(10):949-961; Lewis, et al., *Annals of Biomedical Engineering*, (2002) 30(5):721-730; Lichtenberg, et al., *European Biophysics Journal with Biophysics Letters*, (2007) 36(4-5):499-515). To limit these oxidation reactions, current approaches based on addition of sacrificial antioxidant compounds to the bulk aqueous or oil phase of the encapsulation systems and metal chelators, such as EDTA, are commonly used (Qian, C., et al., supra; Lee, et al., supra; Tikekar, et al, supra; Berton, et al., *Food Chemistry*, (2012) 131(4): 1360-1369; Berton, et al., *Journal of Agricultural and Food Chemistry*, (2011) 59(9):5052-5061). Other design approaches, such as electrostatic layer-by-layer assembly of materials to modify interfacial thickness and charge, have also been explored. Although this approach is successful in reducing oxidation of encapsulated materials, it is not commercially viable, as it is a multi-step process involving separation of colloidal particles at each coating step (Zhao, et al., *Journal of Food Engineering*, (2013) 118(4):421-425). In addition, colloidal instability can be induced due to bridging flocculation among droplets (Zhao, et al., supra).

Current Status of Bio-Encapsulation Process

Cell Based Carriers:

At present, limited research has been conducted to evaluate bioencapsulation approaches using cells as an encapsulation matrix (Shi, et al., *Vibrational Spectroscopy*, (2010) 53(2): 289-295; Shi, et al, *International Journal of Pharmaceutics*, (2008) 349(1-2):83-93; Paramera, et al., *Food Chemistry*, (2011) 125(3):913-922; Paramera, et al., *Food Chemistry*, (2011) 125(3):892-902). Some of the prior research in this area has used conventional diffusion-based approaches to encapsulate bioactives in cells and lipid bodies. Often, to aid diffusion processes in cells and isolated lipid bodies, elevated temperatures are used for an extended period of time (Shi, et al., *Vibrational Spectroscopy*, (2010) supra; Paramera, et al., *Food Chemistry*, (2011) supra). Despite these efforts, these processes have low encapsulation efficiencies (~15%), typically requiring over 24-48 hours of incubation time (Shi, et al, *International Journal of Pharmaceutics*, (2008) supra). In addition, incubation of bioactive compounds at high temperatures for an extended period of time itself can damage the bioactive compounds. See, e.g., Wang, et al., *Journal of Pharmaceutical and Biomedical Analysis*, 1997. 15(12): p. 1867-1876; Ansari, et al., *J Pharm Biomed Anal*, 2005. 39(1-2): p. 132-8; Perez-Conesa, et al., *Innovative Food Science & Emerging Technologies* 10.2 (2009): 179-188; Seeram, et al., *Journal of Agricultural and Food Chemistry* 49.10 (2001): 4924-4929; Rose, et al., *Natural product reports* 22.3 (2005): 351-368; Mrkic, et al., *Journal of the Science of Food and Agriculture* 86.10 (2006): 1559-1566; and Nilles, et al., *Journal of agricultural and food chemistry* 23.3 (1975): 410-415.

Although low encapsulation efficiencies limit the utility and marketability of these previous methods, in vitro studies have demonstrated promising results for bio-inspired systems, showing retention and stability of bioactives in simulated gastric fluid (SGF) and release in simulated intestinal fluid (SIF) (Paramera, et al., *Food Chemistry*, (2011) 125(3):913-922; Paramera, et al., *Food Chemistry*, (2011) 125(3):892-902).

Oleosomes and Milk Fat Globule-Based Carriers:

In oil seeds, such as soybean, sunflower and almond, oil is stored in discrete sub-cellular structures that are called oleosomes (Kapchie, et al., *Food Research International*, (2010) 43(1):241-247). These oleosomes are coated with phospholipids and interfacial proteins called oleosins that impart remarkable stability to these oleosomes against environmental stresses such as moisture, temperature and oxidation (Iwanaga, et al, *Journal of Agricultural and Food Chemistry*, (2008) 56(6):2240-2245). Recent studies showed significant oxidative stability of soybean oil within its oleosomes (Chen, et al., *Food Chemistry*, (2012) 132(3): 1514-1520; Kapchie, et al., *Food Chemistry*, (2013) 141(3): 2286-2293). Significant prior studies have been performed on extraction and isolation of these oleosomes from various sources, including almonds, soybeans and sunflower seeds (Kapchie, et al., *Journal of Agricultural and Food Chemistry*, (2008) 56(5): 1766-1771; Millichip, et al., *Biochemical Journal*, (1996) 314:333-337; Beisson, et al., *Plant Physiology and Biochemistry*, (2001) 39(7-8):623-630). However, little work has been performed in the area of infusion of bioactives into these oleosomes, e.g., to improve the stability of the bioactives.

Similar to oleosomes, milk fat globules are the natural lipid structures that are present in raw, un-homogenized milk from various dairy animals. Each fat globule is surrounded and stabilized by a milk fat globule membrane. This membrane is typically composed of a sophisticated arrangement of polar lipids and specific proteins, some of which may have a significant protective effect on human health (Le, et al., *International Dairy Journal*, (2013) 32(2): 110-120). Although milk fat globules and their membranes have been extensively studied, there is little or no evidence of them being used for encapsulation and delivery of bioactives.

Type II diabetes, cardiovascular disease, and hypertension are metabolic diseases associated with obesity. Although excessive energy intake (i.e. overeating, particularly foods high in fat) and lack of exercise contribute to obesity, a large body of recent research has shown that gut microbes have a profound effect on fat accumulation and chronic inflammation (Kim, et al., *Environmental Microbiology Reports*, (2013) 5(5):765-775; Burcelin, et al., *MS-Medecine Sciences*, (2013) 29(8-9):800-806; Vajro, et al., *Journal of Pediatric Gastroenterology and Nutrition*, (2013) 56(5): p. 461-468; Delzenne, et al., *British Journal of Nutrition*, (2013) 109:S81-S85; Vipperla, et al., *Nutrition in Clinical Practice*, (2012) 27(5):624-635; Hullar, et al., *Obesity Treatment and Prevention: New Directions*, (2012) 73:67-79; De Bandt, et al., *Current Opinion in Clinical Nutrition and Metabolic Care*, (2011) 14(4):334-340). Gut microbes can influence systemic chronic inflammation by many pathways, including translocation of gram negative bacterial cell wall fragments, such as lipopolysaccharides (LPS), from the gut into the body (Moreira, et al., *British Journal of Nutrition*, (2012) 108(5):801-809; Nakamura, et al., *Nutrition & Metabolism*, (2012) p. 9; Laugerette, et al., *Biochimie*, (2011) 93(1):39-45; Cani, et al., *Acta Gastro-Enterologica Belgica*, (2010) 73(2):267-269; Cani, et al., *Pathologie Biologie*, (2008) 56(5):305-309). Dietary components, such as flavonoids, curcumin, and other bioactive compounds present in plant foods, have the potential to modulate inflammation by altering intestinal tight junction permeability and the composition and numbers of gut bacteria (the microbiome) (Moreira, et al., *British Journal of Nutrition*, (2012) 108(5):801-809; Neyrinck, et al., *Plos One*, (2013) 8(11); Machado, et al., *Helicobacter*, (2012) 17:97). Despite significant potential, there are key technical and social challenges that limit the beneficial impact of a plant diet. The key technical challenges include: (a) low and variable concentration of bioactive compounds per plant cell (Bae, et al., *Journal of Food Composition and Analysis*, (2014) 33(2): 195-202; Cermak, et al, *Molecular Nutrition & Food Research*, (2009) 53:S184-S193; Dekker, et al., *Proceedings of the 3rd International Symposium on Applications of Modelling as an Innovative Technology in the Agri-Food Chain*, (2005) 674:71-76); (b) a single plant source lacking diversity of bioactive compounds and (c) plant microstructures limiting bioaccessibility and bioavailability of the bioactive compounds (Cermak, et al., supra; Dekker, et al., supra; Schweiggert, et al., *British Journal of Nutrition*, (2014) 111(3):490-498; Schweiggert, et al., *Food Chemistry*, (2012) 135(4):2736-2742). In addition to technical challenges, there are also societal, regional and socio-economic factors that limit the beneficial impact of a plant diet. To address some of these limitations, including consumer preference, synthetic encapsulation systems such as emulsions, micro and nanoparticles have also been proposed for the delivery of bioactives through consumer friendly products such as beverages and snack foods. However, many of these synthetic encapsulation systems lack the complexity of plant cell walls to retard release of bioactives in gastric and intestinal tissue, thus limiting the activity of bioactives in colon tissue.

SUMMARY

In one aspect, provided are methods of loading one or more bioactive agents into a lipid membrane microcapsule. In varying embodiments, the methods comprise subjecting the lipid membrane microcapsule in the presence of the one or more bioactive agents to vacuum pressure. In varying embodiments, the lipid membrane microcapsule is subjected to the one or more bioactive agents in an aqueous solution. In varying embodiments, the lipid membrane microcapsule is subjected to the one or more bioactive agents in a non-aqueous solution. In varying embodiments, the lipid membrane microcapsules are suspended in a solution isotonic to the microcapsule containing saturating levels of the bioactives to be loaded or encapsulated into the microcapsules. In varying embodiments, the lipid membrane microcapsules are suspended in a solution hypertonic to the microcapsule containing saturating levels of the bioactives to be loaded or encapsulated into the microcapsules. In varying embodiments, the lipid membrane microcapsules are suspended in a solution hypotonic to the microcapsule containing saturating levels of the bioactives to be loaded or encapsulated into the microcapsules. In some embodiments, the vacuum pressure (e.g., negative pressure) is at least about 3 Torr, e.g., at least about 4 Torr, 5 Torr, 6 Torr, 7 Torr, 8 Torr, 9 Torr. In some embodiments, the vacuum pressure is less than about 10 Torr. In varying embodiments, the lipid membrane microcapsule is subjected to vacuum pressure for less than about 30 minutes, e.g., less than about 25, 20, 15 or 10 minutes. In varying embodiments, the lipid membrane microcapsule is sealed in a container comprising at least about 50% of absolute vacuum levels, e.g., at least about 55%, 60%, 65%, 70%, 75%, 80%, 85% or 90% of absolute vacuum levels, e.g., at least about 91%, 92%, 93%, 94%, 95%, 96%, 97%, 98% or 99% of absolute vacuum levels. In varying embodiments, the methods further comprise, after subjecting the lipid membrane microcapsule to vacuum pressure, subjecting the lipid membrane microcapsule to positive external pressure. In some embodiments, the positive external pressure is at least about 30 MPa. In some embodiments, when subjecting the lipid membrane microcapsule to positive external pressure, the lipid membrane microcapsule is sealed in a container comprising at least about 50% of absolute vacuum levels, e.g., at least about 55%, 60%, 65%, 70%, 75%, 80%, 85% or 90% of absolute vacuum levels, e.g., at least about 91%, 92%, 93%, 94%, 95%, 96%, 97%, 98% or 99% of absolute vacuum levels. In varying embodiments, the lipid membrane microcapsule is subjected to multiple iterations, e.g., 2, 3, 4, 5, 6, 7, 8, 9, 10 iterations, of vacuum pressure. In varying embodiments, the lipid membrane microcapsule is subjected to multiple iterations, e.g., 2, 3, 4, 5, 6, 7, 8, 9, 10 iterations, of vacuum pressure and positive external pressure. In varying embodiments, the bioactive lipid membrane microcapsule is subjected to additional bioactive between each iteration of vacuum pressure. In varying embodiments, the bioactive lipid membrane microcapsule is not subjected to additional bioactive between each iteration of vacuum pressure. In varying embodiments, the lipid membrane microcapsule is subjected to positive external pressure for less than about 90 minutes, e.g., for less than about 80, 70, 60, 50, 40, 30, 20 or 10 minutes. In varying embodiments, the loading does not comprise heating or is performed at ambient temperature. In varying embodiments, the loading is performed at a temperature of less than about 38° C. In some embodiments, the loading does not comprise plasmolysing the lipid membrane microcapsule. In some embodiments, the methods further comprise plasmolysing the lipid membrane microcapsule. In varying embodiments, the loaded lipid membrane microcapsule releases less than about 5% of the encapsulated compound. In varying embodiments, the loading efficiency of the bioactive is at least about 15%, e.g., at least about 20%, 25%, 30%, 35%, 40%, 45%, 50%, 55%, 60%, 65%, 70%, 75%, 80%, 85%, or more. In some embodiments, the lipid membrane microcapsule is subjected to positive external pressure for less than 10 minutes, wherein the loading efficiency of the bioactive is at least about 20%. In varying embodiments, the lipid membrane microcapsule is a cell. In some embodiments, the cell comprises a cell wall. In varying embodiments, the cell wall permeability is modified, e.g., increased in comparison to the unmodified cell wall, e.g., wherein the modified cell wall has reduced or fewer disulfide crosslinkages of cell wall proteins in comparison to the unmodified cell wall. In some embodiments, the cell is a eukaryotic cell. In some embodiments, the cell is a plant cell. In some embodiments, the cell is an algal cell, for example, a Chlorophyta cell or a *Chlorella* cell. In some embodiments, the *Chlorella* cell is selected from *Chlorella minutissima* and *Chlorella sorokiniana*. In some embodiments, the cell is a fungal cell. In some embodiments, the cell is a yeast cell, for example, an ascomycetes, for example, a *Saccharomyces* cell, for example, a *Saccharomyces cerevisiae* cell. In some embodiments, the yeast cell is selected from the group consisting of *Saccharomyces cerevisiae, Candida utilis, Lipomyces starkeyi* and *Phaffia rhodozyma*. In varying embodiments, the yeast cell has been cultured in oxygen-rich conditions sufficient to induce lipogenesis. In varying embodiments, the yeast cell has been cultured in oxygen-poor conditions sufficient to repress lipogenesis. In some embodiments, the cell is a prokaryotic cell, for example, a bacterial cell. In some embodiments, the bacterial cell is selected from the group consisting of a *Bifidobacterium* cell and a *Lactobacillus* cell (e.g., *L. casei*). In some embodiments, the bacterial cell is a gram negative bacterial cell, for example, an *E. coli* cell or an *Agrobacterium tumefaciens* (i.e., *Rhizobium radiobacter*) cell. In some embodiments, the methods further comprise the step of reducing disulfide crosslinking between cell wall proteins. In some embodiments, the cell is not viable. In some embodiments, the cell is inactivated. In varying embodiments, the lipid membrane microcapsule is an extracellular membrane of a cell or is from an extracellular membrane of a cell. In varying embodiments, the lipid membrane microcapsule is a subcellular organelle of a cell or is from a subcellular organelle of a cell. In some embodiments, the subcellular organelle is selected from the group consisting of nucleus, a mitochondrion, chloroplast, Golgi body, nucleoid, microsome, vacuole, adiposome, cytoplasm and endoplasmic reticulum. In varying embodiments, the lipid membrane microcapsule is an exosome or is from an exosome. In varying embodiments, the lipid membrane microcapsule is an oil body or is from an oil body (e.g., an oleosome from a plant cell and/or a plant seed). In some embodiments, the lipid membrane microcapsule is a milk lipid globule or is from a milk lipid globule. In varying embodiments, the lipid membrane microcapsule can withstand pressures of at least about 100 MPa, temperatures of at least about 50° C., and a pH in the range of about 2 to about 10. In some embodiments, the lipid membrane microcapsules have an average or mean diameter in the range of about 0.03 µm to about 100 µm, e.g., in the range of about 0.1 µm to about 100 µm. In varying embodiments, the one or more bioactives are independently selected from the group consisting of a small organic compound, a peptide, a polypeptide, a polynucleotide, and a fatty acid. In varying embodiments, the one or more bioactives have a molecular weight in the range of about 10 Da to about 30 kDa. In some embodiments, at least one of the one or more bioactives is hydrophobic. In some embodiments, at least one of the one or more bioactives is hydrophilic. In some embodiments, at least one hydrophobic bioactive and at least one hydrophilic bioactive are encapsulated into the lipid membrane microcapsule. In some embodiments, the hydrophobic bioactive is selected from the group consisting of curcurmin, an omega-3 lipid, an omega-6 lipid, retinol, betacarotene, and mixtures thereof; and the hydrophilic bioactive comprises catechin and/or epicatechin. In some embodiments, at least one of the one or more bioactives is insulin. In some embodiments, at least one of the one or more bioactives is a small organic compound. In varying embodiments, the small organic compound is solubilized or suspended in an aqueous solution comprising a lower alcohol (e.g., methanol, ethanol, propanol, isopropanol). In some embodiments, the small organic compound is selected from the group consisting of curcumin, turmeric, a flavonoid, a retinoid, a vitamin, a flavoring, a colorant, a dye, a pesticide, an herbicide, a fungicide, an antioxidant, a chemotherapeutic agent, and mixtures thereof. In some embodiments, the small organic compound is selected from the group consisting of a phenolic acid, a flavonoid, a terpenoid, a carotenoid, an alkaloid, a phytosterol, a lipid-soluble vitamin, a water-soluble vitamin, a bioactive lipid, a stilbenoid, a coumarin, a lignoid, a xanthonoid, a glycoside, an anthraquinone, and mixtures thereof. In some embodiments, the phenolic acid is selected from the group consisting of a hydroxybenzoic acid, a hydroxycinnamic acid, and derivatives and mixtures thereof.

In some embodiments, the phenolic acid is a hydroxybenzoic acid derivative selected from the group consisting of p-hydroxybenzoic acid, gallic acid, protocatechuic acid, vanillic acid and syringic acid. In some embodiments, the phenolic acid is a hydroxycinnamic acid derivative selected from the group consisting of p-coumaric acid, caffeic acid, ferulic acid, curcurmin, chlorogenic acid and sinapic acid. In some embodiments, the flavonoid is selected from the group consisting of flavonols (fisetin, quercetin, kaempferol, myricetin, and galangin), flavones (luteolin, apigenin, and chrysin), flavanols (catechin, epicatechin, epigallocatechin (EGC), epicatechin gallate (ECG), and EGC gallate (EGCG)), flavanones (naringenin, hesperitin, and eriodictyol), biflavanoids (isocryptomerin and amentoflavone), anthocyanidins and/or anthocyanins (cyanidin, malvidin, peonidin, pelargonidin, and delphinidin), isoflavonoids (genistein, daidzein, glycitein, and formononetin), chalcones (isobavachalcone, kanzonol C, erioschalcones A and B, and panduratin C), quinones, xanthones, acridones, kalihinanes, artemisinin and its derivatives, quinine and its derivatives, and mixtures thereof. In some embodiments, the terpenoid is selected from the group consisting of carotenoids (lycopene, lutein, zeaxanthin, β-carotene, β-cryptoxanthin, retinol and its derivatives), saponins (ginsenoside, astragaloside, and phanoside), terpenoid acids (dehydrotrametenolic acid), and mixtures thereof. In some embodiments, the alkaloid is selected from the group consisting of β-carbolines (nostocarboline, manzanine A, and homofascaplysin), xanthines (caffeine, theophylline, and theobromine), phenethylamines (dopamine, epinephrine, and norepinephrine), quinolones (berberine, protopine, and β-hydrastine), isoquinolines (schulzeines A, B and C) carbazoles (mahanimbine), bisbenzylisoquinolines (fangachinoline, tetrandine and stephenanthrine), quinolizidines (lupanine and 2-thionosparteine), and mixtures thereof. In some embodiments, the sulfur-containing compound is selected from the group consisting of isothiocyanates (sulforaphane, allyl isothiocyanate, and phenethyl isothiocyanate). In some embodiments, the phytosterol is selected from the group consisting of sitosterol (3β-stigmast-5-en-3ol); sitostanol (3β,5α-stigmastan-3-ol), campesterol (3β-ergost-5-en-3-ol), campestanol (3β,5α-ergostan-3-ol), stigmasterol (3β-stigmasta-5,22-dien-3-ol), brassicasterol (3β-ergosta-5,22-dien-3-ol), and mixtures thereof. In some embodiments, the lipid-soluble vitamin is selected from the group consisting of vitamin A (retinol, beta-carotene), retinal, retinoic acid, retinyl esters (e.g., retinyl acetate, retinyl palmitate and retinyl propionate) and provitamin A carotenoids (e.g., beta-carotene, alpha-carotene and beta-cryptoxanthin), vitamin E, vitamin D, vitamin K, and mixtures thereof. In some embodiments, the water-soluble vitamin is selected from the group consisting of vitamin C, B vitamins (B-1, B-2, B-3, B-6, B-7, B-9, B-12, B10 or coenzyme b10), nicotinic acid, niacinamide, nicotinamide, 5-methyltetrahydrofolate (5-MTHF), and mixtures thereof. In varying embodiments, the bioactive lipid is selected from the group consisting of Docosahexaenoic Acid (DHA); Eicosapentaenoic Acid (EPA); Alpha-linolenic Acid (ALA), omega-6 fatty acids (Arachidonic acids), and mixtures thereof. In some embodiments, the small organic compound is a colorant selected from the group consisting of fisetin, annatto extract, beet extract, caramel extract, beta-carotene, grape skin extract, cochineal extract, carmine, paprika oleoresin, saffron extract, FD&C Blue No. 1, FD&C Blue No. 2, FD&C Green No. 3, FD&C Red No. 3, FD&C Red No. 40, FD&C Yellow No. 5, FD&C Yellow No. 6, Orange B, and Citrus Red No. 2, a fluorescein dye, a rhodamine dye, an anthocyanin, a coumarin, a pyrene dye, a xanthene dye, an azo dye, and mixtures thereof. In some embodiments, the small organic compound is a flavorant selected from the group consisting of diacetyl (buttery), isoamyl acetate (banana), benzaldehyde (bitter almond), cinnamic aldehyde (cinnamon), ethyl propionate (fruity), methyl anthranilate (grape), limonene (orange), ethyl decadienoate (pear), allyl hexanoate (pineapple), ethyl maltol (cotton candy), ethylvanillin (vanilla), methyl salicylate (wintergreen), 2-methyl-2-pentenoic acid (fresh strawberry), 2-methyl-4-pentenoic acid (cooked strawberry), menthol, glutamic acid, glycine, guanylic acid, inosinic acid, a 5'-ribonucleotide salt, acetic acid, ascorbic acid, citric acid, fumaric acid, lactic acid, malic acid, phosphoric acid, tartaric acid, and mixtures thereof. In some embodiments, the small organic compound is a vitamin selected from the group consisting of retinol, retinal, retinoic acid, retinyl esters (e.g., retinyl acetate, retinyl palmitate and retinyl propionate) and provitamin A carotenoids (e.g., beta-carotene, alpha-carotene and beta-cryptoxanthin), retinol (vitamin A), thiamine (vitamin B1), riboflavin (vitamin B2), niacin, pyridoxine HCl (vitamin B6), folate, cyanocobalamin (vitamin B12), biotin, pantothenic acid, vitamin C, vitamin D (including cholecalciferol (D2) and ergocalciferol (D3)), vitamin E, vitamin K, and mixtures thereof. In some embodiments, the small organic compound is a chemotherapeutic agent selected from the group consisting of alkylating agent(s), stimulant(s), platinum-coordination complex(es), anti-metabolite(s), plant alkaloid(s) and/or terpenoid(s), vinca alkaloid(s), podophyllotoxin(s), camptothecin(s), anthracycline(s), aromatase inhibitor(s), taxane(s), topoisomerase inhibitor(s), antibiotic(s), hormone(s), differentiating agent(s), kinase inhibitor(s), antineoplastic agent(s), and mixtures thereof.

In a further aspect, provided are lipid membrane microcapsules encapsulating or containing one or more bioactives produced by the methods described above and herein. In varying embodiments, the lipid membrane comprises one or more ligands on its external surface. In varying embodiments, the one or more bioactives encapsulated into the lipid membrane microcapsule are chemically stable for at least 5 days, e.g., at least about 6, 7, 8, 9, 10, 14, 21 or more, days, e.g., at a temperature in the range of about 4° C. to about 45° C., e.g., about 4° C. to about 30° C., in an isotonic solution and a pH in the range of about 6-8. In varying embodiments, the lipid membrane microcapsule releases less than 25%, e.g., less than 20%, 15%, 10%, 5%, or less, of the encapsulated bioactive in a gastric acidic environment or simulated gastric acid environment.

In a further aspect, provided are lipid membrane microcapsules encapsulating or containing at least one hydrophobic bioactive and at least one hydrophilic bioactive. In varying embodiments, the hydrophobic bioactive is selected from the group consisting of curcurmin, an omega-3 lipid, an omega-6 lipid, retinol, betacarotene, and mixtures thereof; and the hydrophilic bioactive comprises catechin and/or epicatechin. In some embodiments, the lipid membrane microcapsule is a cell. In varying embodiments, the cell comprises a cell wall. In varying embodiments, the cell wall permeability is modified, e.g., increased in comparison to the unmodified cell wall, e.g., wherein the modified cell wall has reduced or fewer disulfide cross-linkages of cell wall proteins in comparison to the unmodified cell wall. In some embodiments, the cell is a eukaryotic cell, e.g., a plant cell, an algal cell, a fungal cell, a yeast cell. In some embodiments, the algal cell is a Chlorophyta cell. In some embodiments, the algal cell is a *Chlorella* cell. In some embodiments, the *Chlorella* cell is selected from *Chlorella minutissima* and *Chlorella sorokiniana*. In some embodiments, the yeast cell is an ascomycetes, e.g., a *Saccharomyces* cell, e.g., a *Saccharomyces cerevisiae* cell. In some embodiments, the yeast cell is selected from the group consisting of *Saccharomyces cerevisiae, Candida utilis, Lipomyces starkeyi* and *Phaffia rhodozyma*. In varying embodiments, the yeast cell has been cultured in oxygen-rich conditions sufficient to induce lipogenesis. In varying embodiments, the yeast cell has been cultured in oxygen-poor conditions sufficient to repress lipogenesis. In some embodiments, the cell is a prokaryotic cell, for example, a bacterial cell. In some embodiments, the bacterial cell is selected from the group consisting of a *Bifidobacterium* cell and a *Lactobacillus* cell (e.g., *L. casei*). In some embodiments, the bacterial cell is a gram negative bacterial cell, for example, an *E. coli* cell or an *Agrobacterium tumefaciens* (i.e., *Rhizobium radiobacter*) cell. In varying embodiments, the cell is not viable. In some embodiments, the cell is inactivated. In some embodiments, the lipid membrane microcapsule is an extracellular membrane of a cell or is from an extracellular membrane of a cell. In some embodiments, the lipid membrane microcapsule is a subcellular organelle of a cell or is from a subcellular organelle of a cell. In some embodiments, the subcellular organelle is selected from the group consisting of nucleus, a mitochondrion, chloroplast, Golgi body, nucleoid, microsome, vacuole, adiposome, cytoplasm and endoplasmic reticulum. In some embodiments, the lipid membrane microcapsule is an exosome or is from an exosome. In some embodiments, the lipid membrane microcapsule is an oil body or is from an oil body, e.g., an oleosome (e.g., from a plant cell and/or a plant seed). In some embodiments, the lipid membrane microcapsule is a milk lipid globule or is from a milk lipid globule. In some embodiments, the lipid membrane microcapsule can withstand pressures of at least about 100 MPa, temperatures of at least about 50° C., and a pH in the range of about 2 to about 10. In some embodiments, the lipid membrane microcapsules have an average or mean diameter in the range of about 0.03 µm to about 100 µm, e.g., in the range of about 0.1 µm to about 100 µm.

In a further aspect, provided are compositions edible by a mammal comprising a lipid membrane microcapsule as described above and herein. In varying embodiments, the edible composition is selected from a beverage, a food, a nutraceutical, a compressed cake, a powder, a suspension, and a capsule.

In another aspect, provided are methods of topically administering or delivering a bioactive compound to a mammalian subject. In varying embodiments, the methods comprise contacting the skin or mucosal tissues (e.g., oral cavity, intranasal passages) of the mammalian subject with a lipid membrane microcapsule as described above and herein. In varying embodiments, the lipid membrane microcapsule binds to the skin or mucosal tissue and releases the bioactive into the tissue. In varying embodiments, the lipid membrane microcapsule releases the bioactive into the tissue within about 30 min, 25 min, 20 min, 15 min, 10 min, 5 min, or less, of contacting or binding to the tissue.

In a further aspect, provided are methods of administering or delivering a bioactive compound to the intestine of a mammalian subject, comprising orally administering to the mammalian subject a lipid membrane microcapsule as described above and herein. In some embodiments, the intestine comprises the upper or small intestine (e.g., duodenum, jejunum, ileum). In some embodiments, the intestine comprises the lower or large intestine (e.g., colon, rectum). In another aspect, provided are methods of administering or delivering a bioactive compound to the colon of a mammalian subject. In some embodiments, the methods comprise orally or rectally administering to the mammalian subject a lipid membrane microcapsule as described above and herein. In varying embodiments, the lipid membrane microcapsule binds to the intestinal tissue and/or gut bacteria, and releases the bioactive into the tissue or in the intestinal tract. In varying embodiments, the lipid membrane microcapsule releases the bioactive into the tissue within about 30 min, 25 min, 20 min, 15 min, 10 min, 5 min, or less, of contacting or binding to the tissue.

In another aspect, provided are methods of preventing, reducing, ameliorating, mitigating and/or treating a disease condition in a mammal. In some embodiments, the methods comprise administering to the mammal a lipid membrane microcapsule as described above and herein. In varying embodiments, the lipid membrane microcapsule is administered via a route selected from the group consisting of orally, rectally, vaginally, topically, intravenously, intraperitoneally, intradermally and intralesionally. In varying embodiments, the disease condition is selected from obesity, metabolic syndrome, Type II diabetes, cardiovascular diseases, cancer prevention and therapy, inflammatory diseases, gut inflammation (inflammatory bowel disease, Crohn's disease), and skin disorders (including atopic dermatitis, healing of burn and scars, skin-rejuvenation, inflammation, infection and wounds).

Definitions

The phrases "loading efficiency" or "encapsulation efficiency" interchangeably refer to the encapsulation efficiency on both wet basis determined as follows:

$$EE(\%) = \frac{C_E}{C_T} \times 100,$$

where $C_E$ is the mass of extracted bioactive from the lipid membrane microcapsules after encapsulation on a wet basis and $C_T$ is the amount of bioactive initially added to the lipid membrane microcapsules.

The terms "bioactive agent" and "bioactive compound" interchangeably refer to small organic compounds, polypeptides (e.g., ligands, antibodies), peptidomimetics, nucleic acids, small organic compounds, carbohydrates, lipids and the like, that can be encapsulated in the lipid membrane microcapsules described herein.

The term "hydrophobic" with respect to a bioactive compound refers to compounds having superior solubility in non-polar organic solvents and oils as compared to water (e.g., aqueous) and polar solvents.

The term "hydrophilic" with respect to a bioactive compound refers to compounds having superior solubility in water (e.g., aqueous) and polar solvents as compared to non-polar organic solvents and oils.

As used herein, "administering" refers to local and systemic administration, e.g., including enteral, parenteral, pulmonary, and topical/transdermal administration. Routes of administration for lipid membrane microcapsules that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "effective amount" or "pharmaceutically effective amount" refer to the amount and/or dosage, and/or dosage regime of one or more compounds necessary to bring about the desired result e.g., an amount sufficient to mitigating in a mammal one or more symptoms associated with the target disease (e.g., obesity, metabolic syndrome, Type II diabetes, cardiovascular diseases, cancer prevention and therapy, inflammatory diseases, gut inflammation (inflammatory bowel disease, Crohn's disease), and skin disorders (including atopic dermatitis, healing of burn and scars, skin-rejuvenation, inflammation, infection and wounds)); an amount sufficient to lessen the severity or delay the progression of the target disease in a mammal (e.g., therapeutically effective amounts); or an amount sufficient to reduce the risk or delay the onset, and/or reduce the ultimate severity of a disease characterized by amyloid deposits in the brain in a mammal (e.g., prophylactically effective amounts).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds/lipid membrane microcapsules for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments the subject may not be under the care or prescription of a physician or other health worker.

BRIEF DESCRIPTION OF THE DRAWINGS

FIGS. 2A-D illustrate fluorescence image of curcumin in yeast. A) and B) represent white light and FITC images, respectively, of curcumin encapsulated into yeast using conventional diffusion limited processing. C) and D) represent white light and FITC images, respectively, of curcumin encapsulated into yeast using vacuum infusion processing. The S/N value located at the top rights of images B and D represent the average signal intensity divided by the average background intensity. The S/N for the control is 2.01 while that for the yeast containing curcumin is 6.01, nearly a three-fold increase. Magnification: 20× (Images were left unedited; only a scale bar was added).

FIGS. 9A-B illustrate encapsulation of β-carotene into raw milk fat globules using vacuum infusion. A: White light; B: Fluorescence signal from beta-carotene (red)

FIGS. 14A-C illustrate fermentation gut bacteria association with microcapsules. A) Emulsion with no observable associated bacteria. B) Milk fat globule (MFG) with some associated bacteria. C) Yeast with significant gut bacteria association with microcapsules.

FIGS. 15A-B illustrate (A) Imaging of porcine oral tissue with and without inactivated yeast cells. The yeast cells were inactivated using 35% ethanol. Yeast cells were labeled with propidium iodide (PI) dye and (B) Signal intensity (PI or red channel) of yeast attachment on porcine mouth mucosal tissue as a function of time. The oral tissue was rinsed 4-5 times following the initial incubation of yeast cells on the tissue for a specified period of time.

FIGS. 16A-B illustrate attachment of inactivated yeast cells on the surface of porcine skin. (A) The image shows the yeast cells (labeled with PI dye) (left panel), the autofluorescence of skin tissue (center panel) and the resulting signal of incubation of labeled yeast cells on skin after 30 minutes of incubation (right panel). (B) Signal intensity (PI or red channel) of yeast attachment on porcine skin tissue as a function of time.

FIGS. 17A-D illustrate Nile red fluorescence signal contrast of porcine skin between (d) incubated with yeast encapsulation system and (b) non-incubated. The images were taken after 12 h of incubation at room temperature using an Olympus inverted fluorescence microscope with a ×20 objective. (a),(c) are corresponding brightfield images of (b),(d), respectively.

DETAILED DESCRIPTION

1. Introduction

Figure 1:
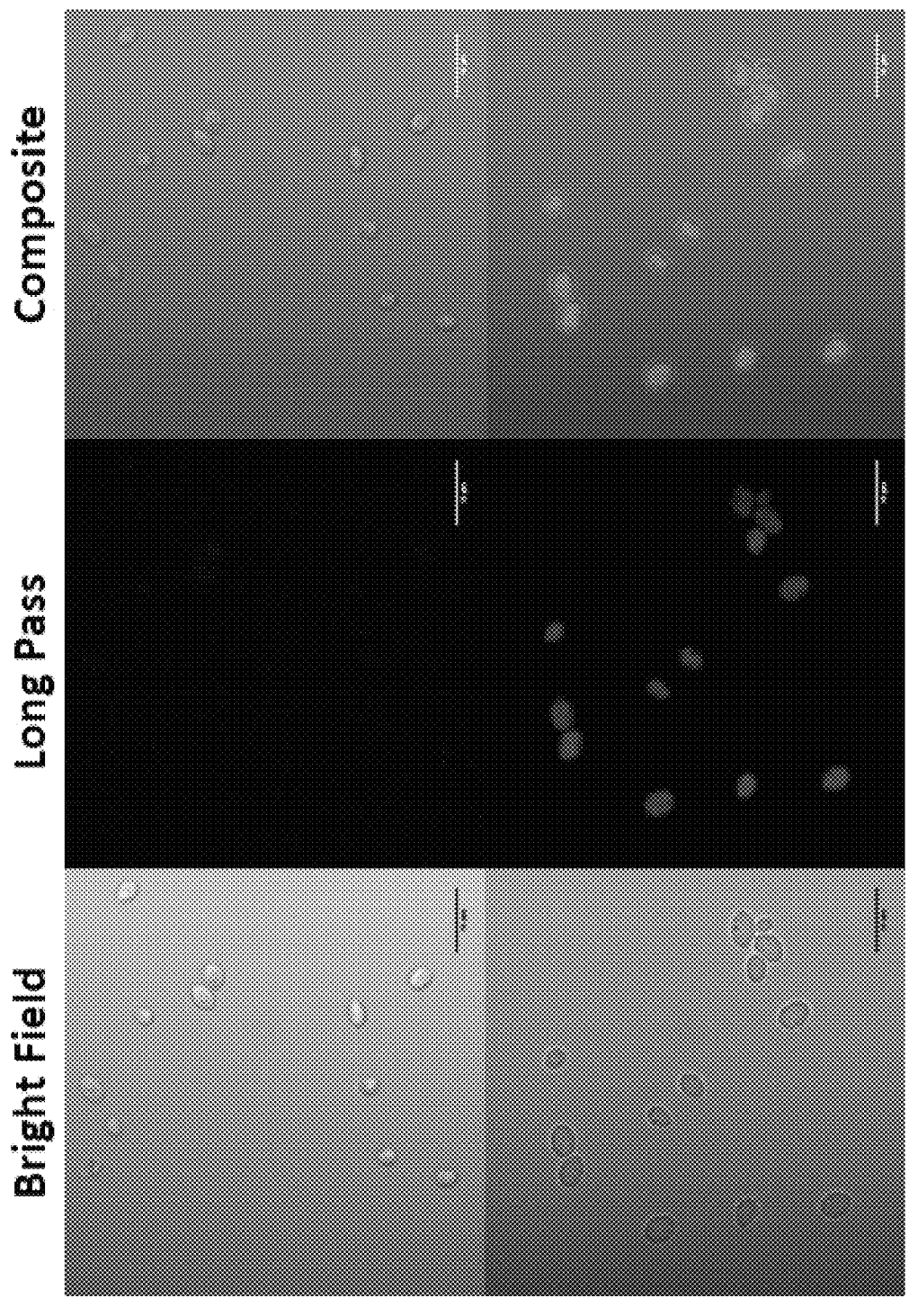
FIG. 1 illustrates confocal microscopy of curcumin in yeast. Curcumin was encapsulated in yeast cells using vacuum infusion; the control yeast cells without the bioactive were treated in the same manner. From left to right, top row: White light image of control yeast; Long pass image of control yeast; Composite image of control yeast. From left to right, bottom row: White light image of curcumin encapsulated in yeast; Long pass image of curcumin encapsulated in yeast; Composite image of curcumin encapsulated in yeast. The average mean fluorescence signal in the cell with respect to the background in the image ("S/N") for the control is 1.68 while that for the yeast containing curcumin is 56.33. The S/N value represents the average signal intensity divided by the average background intensity. Magnification: 100×.
Figure 3:
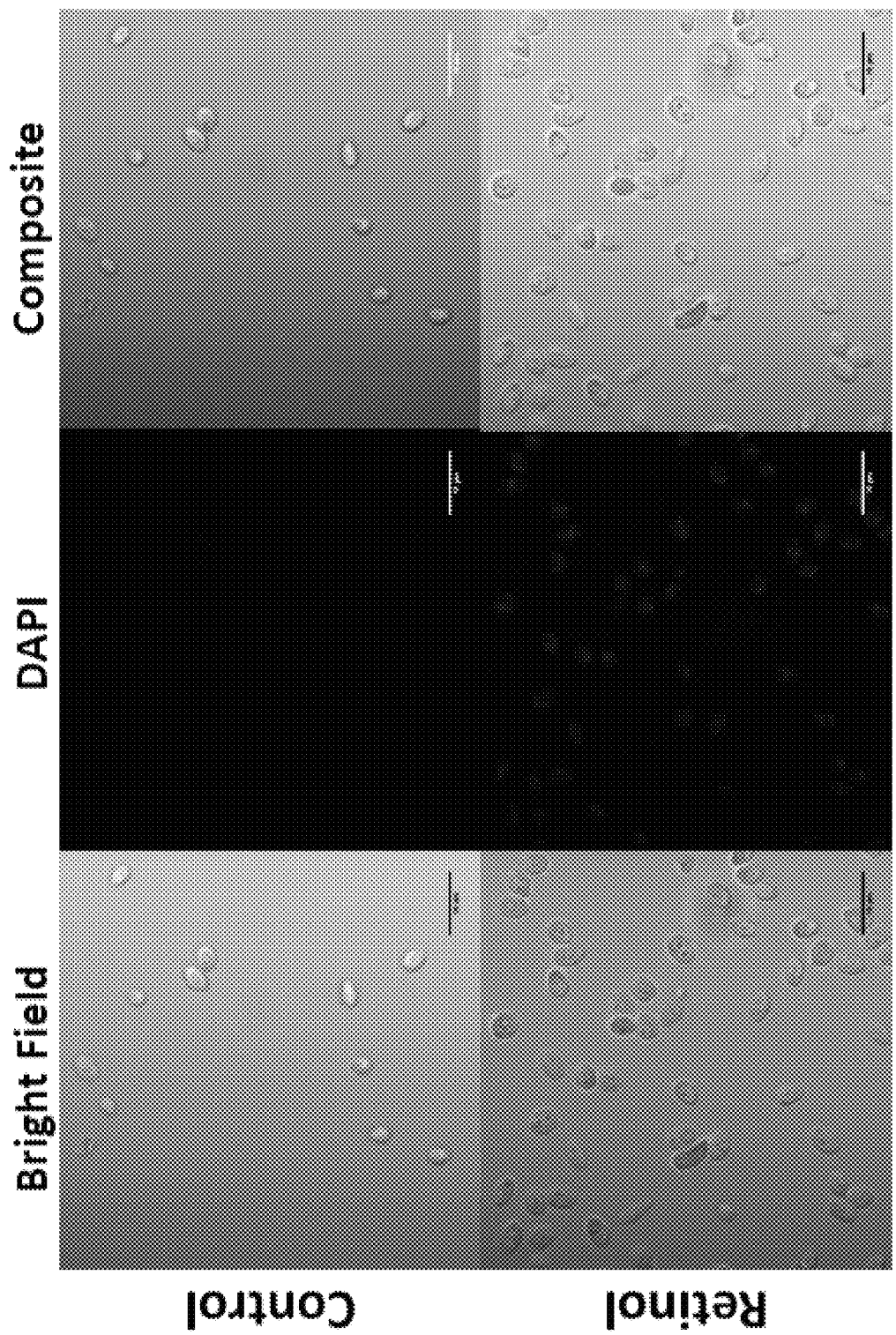
FIG. 3 illustrates confocal, multiphoton microscopy of retinol in yeast. Retinol was encapsulated in yeast cells using vacuum infusion; the control yeast cells without the bioactive were treated in the same manner. From left to right, top row: White light image of control yeast; Image of control yeast in DAPI channel; Composite image of control yeast. From left to right, bottom row: White light image of retinol encapsulated in yeast; Image of retinol encapsulated in yeast in DAPI channel; Composite image of retinol encapsulated in yeast. The S/N for the control is 1.71 while that for the yeast containing retinol is 17.12. The S/N value represents the average signal intensity divided by the average background intensity. Magnification: 100×.
Figure 4:
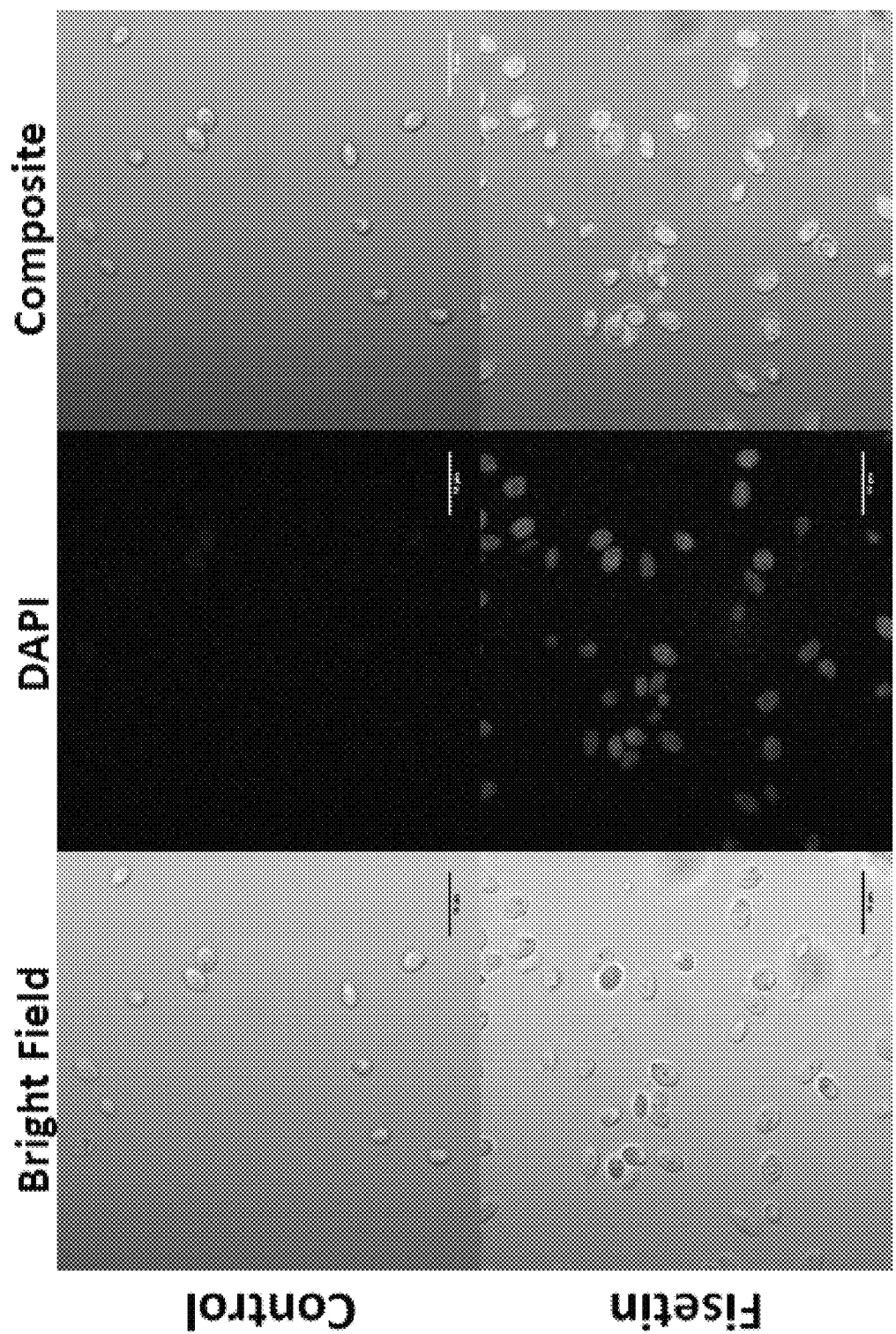
FIG. 4 illustrates confocal, multiphoton microscopy of fisetin in yeast. Fisetin was encapsulated in yeast cells using vacuum infusion; the control yeast cells without the bioactive were treated in the same manner. From left to right, top row: White light image of control yeast; Image of control yeast in DAPI channel; Composite image of control yeast. From left to right, bottom row: White light image of fisetin encapsulated in yeast; Image of fisetin encapsulated in yeast in DAPI channel; Composite image of fisetin encapsulated in yeast. The S/N for the control is 1.71 while that for the yeast containing retinol is 15.30. The S/N value represents the average signal intensity divided by the average background intensity. Magnification: 100×.
Figure 5:
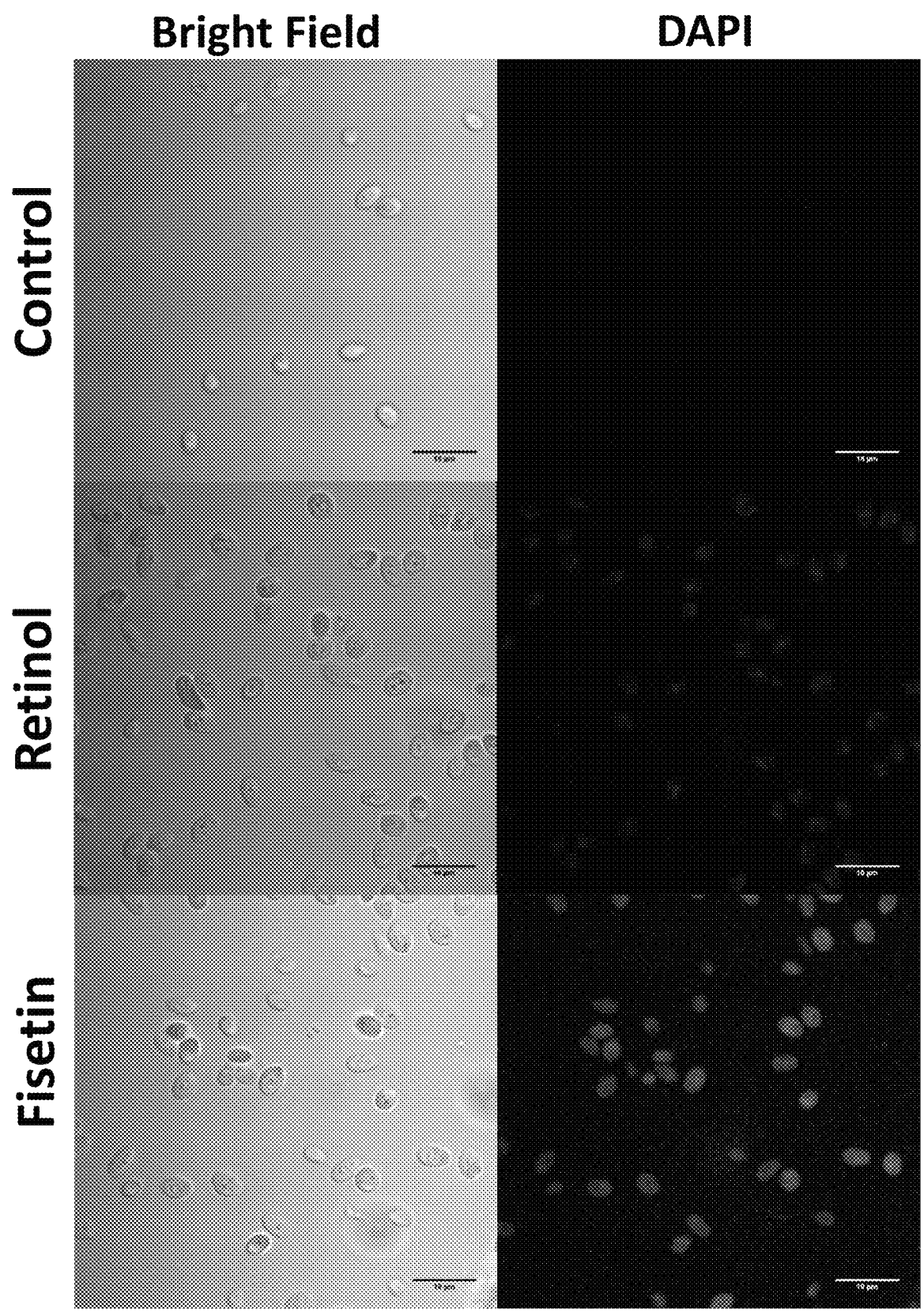
FIG. 5 illustrates confocal multi-photon fluorescence imaging of simultaneously loaded bioactives in yeast carrier. Retinol and fisetin, respectively, were encapsulated into yeast via vacuum infusion and imaged at 370 nm and 488 nm excitation. Magnification: 100×.
Figure 6:
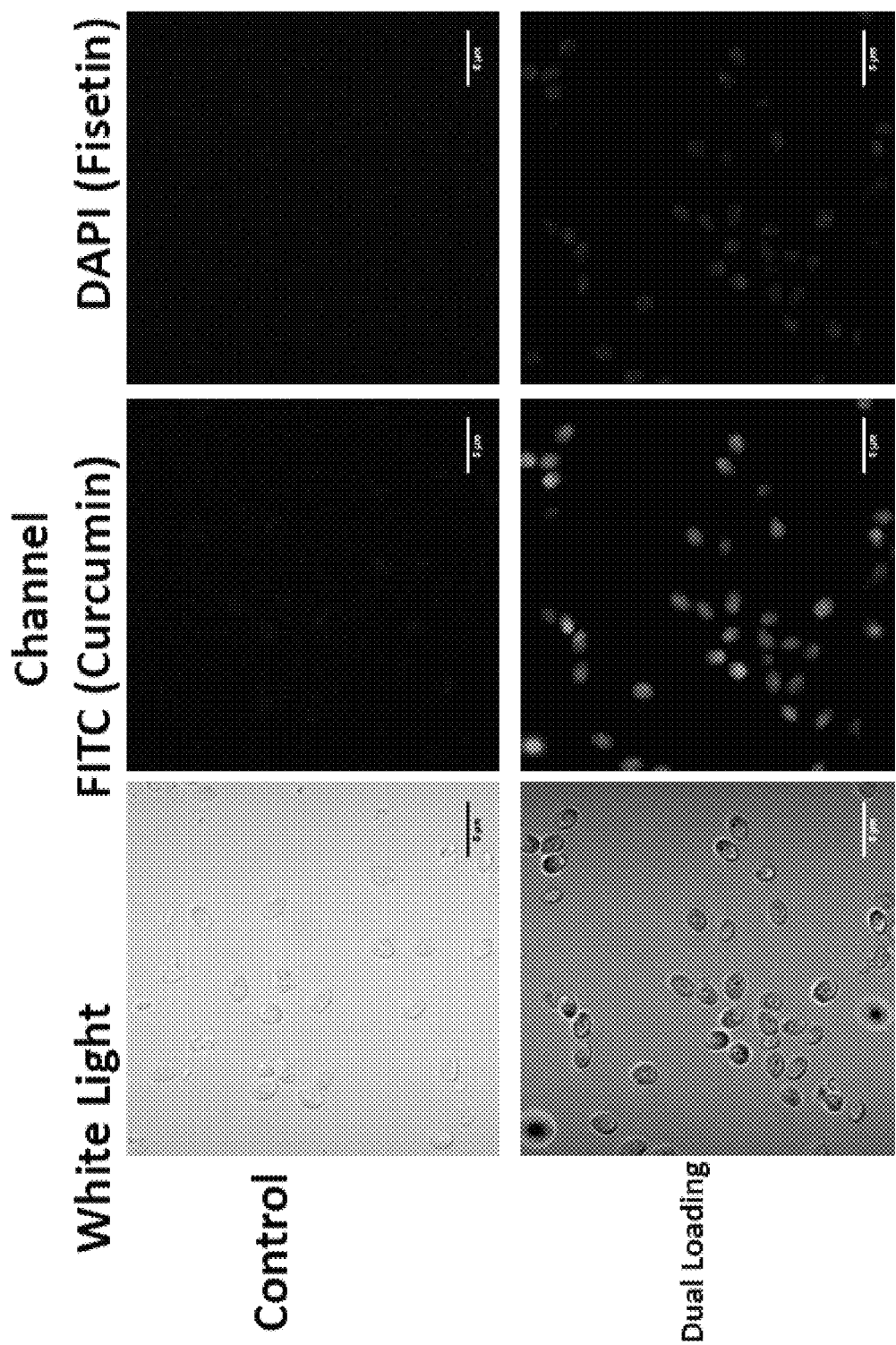
FIG. 6 illustrates confocal and multiphoton fluorescence imaging of dual loaded curcumin and fisetin into yeast cells. The top row represents the control as observed under the white light, FITC and DAPI (multiphoton) channels; note that only the white light image was altered in order to enhance the contrast. The bottom row represents the dual loaded yeast cells as observed under the white light, FITC and DAPI (multiphoton) channels; note that only the white light image was altered in order to enhance the contrast. The DAPI multiphoton channel is able to visualize the fluorescence of fisetin within the sample while the FITC channel is able to elucidate the presence of curcumin within the same sample. Magnification: 100×.
Figure 7:
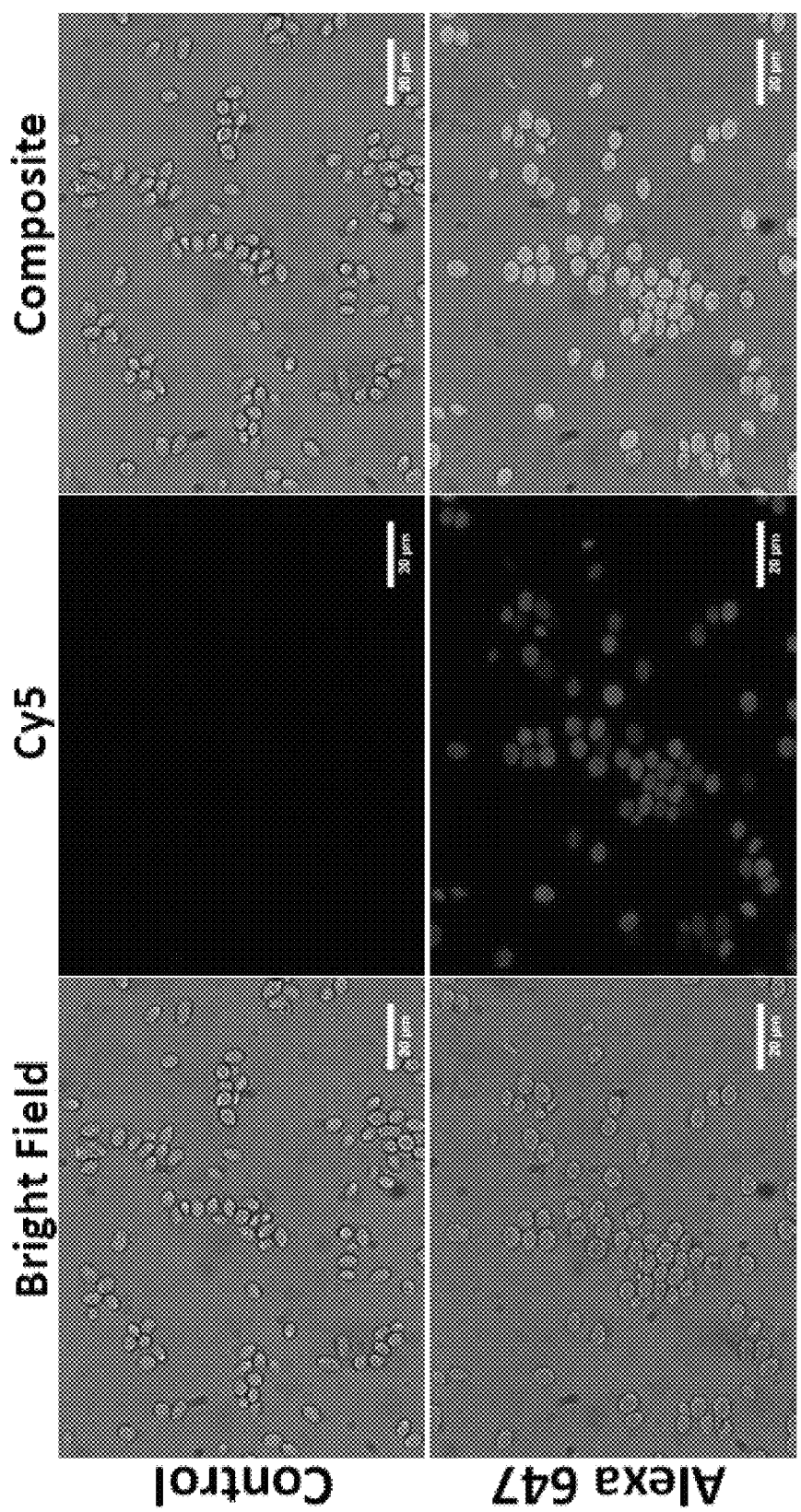
FIG. 7 illustrates fluorescence microscopy of insulin conjugated to Alexa 647 in yeast. Control yeast were treated under vacuum condition with unlabeled insulin. A fluorophore, Alexa 647, was conjugated to insulin and was treated in the same manner as the control. From left to right, top row: White light image of control yeast; Image of control yeast in Cy5 channel; Composite image of control yeast. From left to right, bottom row: White light image of Alexa 647 conjugated insulin encapsulated in yeast; Image of Alexa 647 conjugated insulin encapsulated in yeast in Cy5 channel; Composite image of Alexa 647 conjugated insulin encapsulated in yeast. The S/N for the control is 1.02 while that for the yeast containing retinol is 1.66. The S/N value represents the average signal intensity divided by the average background intensity. Magnification: 60×.

Provided are methods for the highly efficient and rapid encapsulation of bioactives in lipid membranes and isolated lipid bioactives (e.g., cells and fat or lipid globules) without the requirement of elevated temperatures. The methods enable translation of the cell based encapsulation process to industrial practice. Based on their unique structural and compositional features, encapsulation of bioactive agents in cells (e.g., yeast, algae, bacteria cells), oleosomes and milk fat globules increases and improves the oxidative stability of encapsulated bioactive compounds. For example, encapsulation of hydrophobic bioactives (demonstrated using the model hydrophobic bioactive, curcumin) into inactivated yeast using vacuum and/or high pressure processing (HPP) is 4-5-fold more efficient than conventional diffusion techniques under a given solvent condition. Further, encapsulation of hydrophilic bioactives (demonstrated using the model hydrophobic bioactive, fisetin) into inactivated yeast using vacuum or HPP is generally more efficient (1.4-2.3×) than conventional diffusion techniques. In addition, the pressure assisted encapsulation processes also significantly enhance the rate of encapsulation (at least 35 fold reduction in time required for the encapsulation). Introduction of food-grade surfactants increases mass of encapsulated bioactive per unit mass of yeast cells by two-fold.

Moreover, whereas simple diffusion techniques are unable to encapsulate larger molecules such as insulin (~5-6 kDa) without cell wall modification (Pham-Hoang, Bao Ngoc, et al., 2013), the vacuum and/or HPP infusion methods described herein successfully encapsulate insulin within cells without cell modification. Employing vacuum and/or HPP infusion methods for bioactive loading into lipid membrane microcapsules can be applied to other natural systems, including milk fat globules and subcellular organelles. Furthermore, vacuum and/or HPP infusion methods allow for dual loading of both hydrophobic and hydrophilic compounds.

In addition, cell-based encapsulants and the lipid membrane microcapsules described herein provide increased storage stability, processing stability and in vivo delivery stability of the encapsulated bioactives. Storage stability (e.g., chemical stability, oxidative stability and pH stability) of bioactives is significantly improved (e.g., at least 5-fold for retinol) as compared to other encapsulation systems, including nanoparticles and emulsions. By avoiding exposure of the bioactives to heating, processing stability of bioactives is also improved as compared to emulsions. For example, loss of retinol during thermal processing was reduced by at least 25-30% by employing vacuum and/or HPP infusion methods. Cell-based encapsulants provide only limited release (less than 20% of the encapsulated amount) of encapsulated material during gastric digestion. This is highly desirable for compounds that can be damaged by the pH and enzymatic environment in the gastric compartment of the gut.

2. Lipid Membrane Microcapsules Loaded with Bioactive Agents

Provided are lipid membrane microcapsules loaded with one or more bioactive agents. In varying embodiments, the lipid membrane microcapsules are naturally occurring entities (e.g., whole inactivated cells, plant oleosomes or milk fat or lipid globules), loaded with one or more bioactive agents that are heterologous or non-endogenous to the lipid membrane microcapsule or loaded with one or more bioactive agents at concentrations substantially higher than what would occur in the naturally occurring lipid membrane microcapsule (e.g., cells, plant oleosomes or milk fat or lipid globules). In varying embodiments, the lipid membrane microcapsule is a subcellular organelle of a cell or is from a subcellular organelle of a cell. In some embodiments, the subcellular organelle is selected from the group consisting of nucleus, a mitochondrion, chloroplast, Golgi body, nucleoid, microsome, vacuole, adiposome, cytoplasm and endoplasmic reticulum. In varying embodiments, the lipid membrane microcapsule is an exosome or is from an exosome. In varying embodiments, the lipid membrane microcapsules have an average or mean diameter in the range of about 0.03 μm to about 100 μm, e.g., in the range of about 0.10 μm to about 100 μm.

In varying embodiments, the lipid membrane microcapsule is a whole or intact cell. Cells of use are edible to a mammal, e.g., approved by FDA for specific uses or Generally Regarded as Safe (GRAS). The cell can be a live cell, but usually is an inactivated cell. The cells can be inactivated using any method known in the art. In some embodiments, the cell is inactivated by chemical treatment (e.g., exposure to an alcohol or an aldehyde). In varying embodiments, the cell has been lyophilized and reconstituted. Cells having cell walls are useful for encapsulating bioactives. In varying embodiments, the lipid membrane microcapsule can be a yeast cell, an algal cell, a plant cell or a bacterial cell. As appropriate, the cell wall permeability of the cell can be unmodified or modified, e.g., by exposure of the cell to a chelation agent, exposure to a reducing agent and/or by altering the cell cultivation environment (e.g., through varying nitrogen levels in the growth media and/or through supplementing cultures with $CO_2$).

In varying embodiments, the lipid membrane microcapsule is a yeast cell. Yeast cells of interest include without limitation, an ascomycetes cell, e.g., a Saccharomyces cell, e.g., a Saccharomyces cerevisiae cell. In some embodiments, the yeast cell is selected from the group consisting of Saccharomyces cerevisiae, Candida utilis, Lipomyces starkeyi and Phaffia rhodozyma. Other fungal/yeast cells of interest include without limitation, Saccharomyces fragilis, Fusarium moniliforme, Rhizopus niveus, Rhizopus oryzae, Aspergillus niger, Aspergillus oryzae, Candida guilliermondii, Candida lipolytica, Candida pseudotropicalis, Mucor pusillus Lindt, Mucor miehei, Rhizomucor miehei, Morteirella vinaceae, Endothia parasitica, Kluyveromyces lactis (previously called Saccharomyces lactis), Kluyveromyces marxianus, Lipomyces starkeyi, Rhodotorula colostri, Rhodotorula dairenensis, Rhodotorula glutinis, Rhodosporium diobovatum, Schizosaccharomyces pombe and Eremothecium ashbyii.

In varying embodiments, the lipid membrane microcapsule is an algal cell. Algal cells of interest include without limitation, Chlorophyta (green algae), Rhodophyta (red algae), Stramenopiles (heteronkonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae). In some embodiments, the algal cell is selected from the group consisting of Chlamydomonas reinhardtii, Dunaliella salina, Haematococcus pluvialis, Chlorella vulgaris, Acutodesmus obliquus, and Scenedesmus dimorphus. In some embodiments, the green alga is selected from the group consisting of Chlamydomonas, Dunaliella, Haematococcus, Chlorella, and Scenedesmaceae. In some embodiments, the Chlamydomonas is a Chlamydomonas reinhardtii. In varying embodiments the Chlorella is a Chlorella minutissima or a Chlorella sorokiniana cell. Other algal cells of interest include without limitation, Gigartinaceae and Soliericeae of the class Rodophyceae (red seaweed): Chondrus crispus, Chondrus ocellatus, Eucheuma cottonii, Eucheuma spinosum, Gigartina acicularis, Gigartina pistillata, Gigartina radula, Gigartina stellate, Furcellaria fastigiata, Analipus japonicus, Eisenia bicyclis, Hizikia fusiforme, Kjellmaniella gyrata, Laminaria angustata, Laminaria longirruris, Laminaria Longissima, Laminaria ochotensis, Laminaria claustonia, Laminaria saccharina, Laminaria digitata, Laminariajaponica, Macrocystis pyrifera, Petalonia fascia, Scytosiphon lome, Gloiopeltis furcata, Porphyra crispata, Porhyra deutata, Porhyraperforata, Porhyra suborbiculata, Porphyra tenera, and Rhodymenis palmate.

In varying embodiments, the lipid membrane microcapsule is a bacterial cell. Bacterial cells of interest include without limitation Bifidobacterium cells and Lactobacillus cells (e.g., L. casei). In some embodiments, the bacterial cell is a gram negative bacterial cell, for example, an E. coli cell or an Agrobacterium tumefaciens (i.e., Rhizobium radiobacter) cell. Other bacterial cells of interest include without limitation, Bacteroides fragilis, Streptomyces natalensis, Streptomyces chattanoogensis, Streptomyces rubiginosus, Actinoplane missouriensis, Streptomyces olivaceus, Streptomyces olivochromogenes, Streptomyces griseus, Bacillus coagulans, Bacillus cereus, Bacillus stearothermophilus, Bacillus subtilis, Xanthomonas campestris, Micrococcus lysodeikticus, Acetobactor suboxydans, Lactococcus lactis, Streptococcus lactis, Streptococcus cremoris, Streptococcus lactis subspecies diacetylactis, Leuconostoc citovorum, Leuconostoc dextranicum, Lactobacillus casei, Lactobacillus-fermentum, and Lactobacillus bulgaricus.

In varying embodiments, the lipid membrane microcapsule is loaded with one or more hydrophilic bioactive agents, one or more hydrophobic bioactive agents or a combination of one or more hydrophilic bioactive agents and one or more hydrophobic bioactive agents, as defined herein. In varying embodiments, a hydrophilic bioactive agent refers to a compound comprising a solubility of greater than or equal to 500 µg/ml in deionized water. In varying embodiments a hydrophobic bioactive agent refers to a compound comprising a solubility of less than or equal to 100 µg/ml in deionized water. The bioactive agents can be any compound sufficiently small to be loaded into the lipid membrane microcapsule. In varying embodiments, the bioactive agents can be small organic compounds, polypeptides, peptides, polynucleotides, carbohydrates, bioactive lipids and/or fatty acids. In varying embodiments, the one or more bioactives have a molecular weight in the range of about 10 Da to about 30 kDa. In some embodiments, the small organic compound is selected from the group consisting of a phenolic acid, a flavonoid, a terpenoid, a carotenoid, an alkaloid, a phytosterol, a lipid-soluble vitamin, a water-soluble vitamin, a bioactive lipid, a stilbenoid, a coumarin, a lignoid, a xanthonoid, a glycoside, an anthraquinone, and mixtures thereof.

Illustrative hydrophobic active agents of interest include without limitation, e.g., alkaloids, carotenoids, phenolic acids, phytosterols, sulfur-containing compounds, bioactive lipids, and lipid-soluble vitamins. In some embodiments, the phenolic acid is selected from the group consisting of a hydroxybenzoic acid, a hydroxycinnamic acid, and derivatives and mixtures thereof. In some embodiments, the phenolic acid is a hydroxybenzoic acid derivative selected from the group consisting of p-hydroxybenzoic acid, gallic acid, protocatechuic acid, vanillic acid and syringic acid. In some embodiments, the phenolic acid is a hydroxycinnamic acid derivative selected from the group consisting of p-coumaric acid, caffeic acid, ferulic acid, curcurmin, chlorogenic acid and sinapic acid. In some embodiments, the phytosterol is selected from the group consisting of sitosterol (3β-stigmast-5-en-3ol); sitostanol (3β,5α-stigmastan-3-ol), campesterol (3β-ergost-5-en-3-ol), campestanol (3β3,5α-ergostan-3-ol), stigmasterol (3β-stigmasta-5,22-dien-3-ol), brassicasterol (3β-ergosta-5,22-dien-3-ol), and mixtures thereof. In some embodiments, the lipid-soluble vitamin is selected from the group consisting of vitamin A (retinol, beta-carotene), retinal, retinoic acid, retinyl esters (e.g., retinyl acetate, retinyl palmitate and retinyl propionate) and provitamin A carotenoids (e.g., beta-carotene, alpha-carotene and beta-cryptoxanthin), vitamin E, vitamin D, vitamin K, and mixtures thereof. In some embodiments, the terpenoid is selected from the group consisting of carotenoids (lycopene, lutein, zeaxanthin, β-carotene, β-cryptoxanthin, retinol and its derivatives), saponins (ginsenoside, astragaloside, and phanoside), terpenoid acids (dehydrotrametenolic acid), and mixtures thereof. In some embodiments, the bioactive lipid is selected from the group consisting of Docosahexaenoic Acid (DHA); Eicosapentaenoic Acid (EPA); Alpha-linolenic Acid (ALA), omega-6 fatty acids (Arachidonic acids), and mixtures thereof. In some embodiments, the sulfur-containing compound is selected from the group consisting of isothiocyanates (sulforaphane, allyl isothiocyanate, and phenethyl isothiocyanate).

Illustrative hydrophilic agents of interest include without limitation, e.g., water-soluble vitamins and flavonoids. In some embodiments, the flavonoid is selected from the group consisting of flavonols (fisetin, quercetin, kaempferol, myricetin, and galangin), flavones (luteolin, apigenin, and chrysin), flavanols (catechin, epicatechin, epigallocatechin (EGC), epicatechin gallate (ECG), and EGC gallate (EGCG)), flavanones (naringenin, hesperitin, and eriodictyol), biflavanoids (isocryptomerin and amentoflavone), anthocyanidins and/or anthocyanins (fisetin, cyanidin, malvidin, peonidin, pelargonidin, and delphinidin), isoflavonoids (genistein, daidzein, glycitein, and formononetin), chalcones (isobavachalcone, kanzonol C, erioschalcones A and B, and panduratin C), quinones, xanthones, acridones, kalihinanes, artemisinin and its derivatives, quinine and its derivatives, and mixtures thereof. In some embodiments, the alkaloid is selected from the group consisting of β-carbolines (nostocarboline, manzanine A, and homofascaplysin), xanthines (caffeine, theophylline, and theobromine), phenethylamines (dopamine, epinephrine, and norepinephrine), quinolones (berberine, protopine, and β-hydrastine), isoquinolines (schulzeines A, B and C) carbazoles (mahanimbine), bis-benzylisoquinolines (fangachinoline, tetrandine and stephenanthrine), quinolizidines (lupanine and 2-thionosparteine), and mixtures thereof. In some embodiments, the water-soluble vitamin is selected from the group consisting of vitamin C, B vitamins (B-1, B-2, B-3, B-6, B-7, B-9, B-12, B10 or coenzyme b10), nicotinic acid, niacinamide, nicotinamide, 5-methyltetrahydrofolate (5-MTHF), and mixtures thereof.

In some embodiments, at least one hydrophobic bioactive and at least one hydrophilic bioactive are encapsulated into the lipid membrane microcapsule. In some embodiments, the hydrophobic bioactive is selected from the group consisting of curcurmin, an omega-3 lipid, an omega-6 lipid, retinol, betacarotene, and mixtures thereof; and the hydrophilic bioactive comprises catechin and/or epicatechin.

In some embodiments, the bioactive is a colorant selected from natural or/and artificial color compounds. The natural color compounds may be selected in form of purified anthocyanin, polyphenolic compounds and/or in form of extract from fruits and/or vegetables that are rich in anthocyanins and/or polyphenolics. Anthocyanin compounds both in purified forms or in natural extracts may be selected from derivatives of anthocyanidins (aglycones): cyanidin (Cy), peonidin (Pn), pelargonidin (Pg), malvidin (Mv), delphinidin (Dp), and petunidin (Pt). The other polyphenolic compounds may include color compounds derived from carotenoids such as beta-carotene and or phenolic acids and their derivatives such as curcumins. The artificial color compounds may include FD&C Blue No. 1, FD&C Blue No. 2, FD&C Green No. 3, FD&C Red No. 3, FD&C Red No. 40, FD&C Yellow No. 5, FD&C Yellow No. 6, Orange B, and Citrus Red No. 2, a fluorescein dye, a rhodamine dye, an anthocyanin, a coumarin, a pyrene dye, a xanthene dye, an azo dye, and mixtures thereof. In some embodiments, the bioactive is a flavorant selected from the group consisting of diacetyl (buttery), isoamyl acetate (banana), benzaldehyde (bitter almond), cinnamic aldehyde (cinnamon), ethyl propionate (fruity), methyl anthranilate (grape), limonene (orange), ethyl decadienoate (pear), allyl hexanoate (pineapple), ethyl maltol (cotton candy), ethylvanillin (vanilla), methyl salicylate (wintergreen), 2-methyl-2-pentenoic acid (fresh strawberry), 2-methyl-4-pentenoic acid (cooked strawberry), menthol, glutamic acid, glycine, guanylic acid, inosinic acid, a 5'-ribonucleotide salt, acetic acid, ascorbic acid, citric acid, fumaric acid, lactic acid, malic acid, phosphoric acid, tartaric acid, and mixtures thereof. In some embodiments, the bioactive is a vitamin selected from the group consisting of retinol, retinal, retinoic acid, retinyl esters (e.g., retinyl acetate, retinyl palmitate and retinyl propionate) and provitamin A carotenoids (e.g., beta-carotene, alpha-carotene and beta-cryptoxanthin), retinol (vitamin A), thiamine (vitamin B1), riboflavin (vitamin B2), niacin, pyridoxine HCl (vitamin B6), folate, cyanocobalamin (vitamin B12), biotin, pantothenic acid, vitamin C, vitamin D (including cholecalciferol (D2) and ergocalciferol (D3)), vitamin E, vitamin K, and mixtures thereof. In some embodiments, the bioactive is a chemotherapeutic agent selected from the group consisting of alkylating agent(s), stimulant(s), platinum-coordination complex(es), anti-metabolite(s), plant alkaloid(s) and/or terpenoid(s), vinca alkaloid(s), podophyllotoxin(s), camptothecin(s), anthracycline(s), aromatase inhibitor(s), taxane(s), topoisomerase inhibitor(s), antibiotic(s), hormone(s), differentiating agent(s), kinase inhibitor(s), antineoplastic agent(s), and mixtures thereof.

Bioactive agents encapsulated within the lipid membrane microcapsules described herein are stable for extended periods of time, e.g., protected against or exhibit decreased degradation due to any of a number of reasons, including exposure to oxidation, light (photo damage), high or low pH (acidic or basic), temperature extremes (e.g., heat or freezing), and/or storage conditions (e.g., extended time periods above freezing, e.g., at temperatures in the range of about 0° C. to about 45° C.). Generally, the lipid membrane microcapsules can withstand pressures of at least about 100 MPa, temperatures of at least about 50° C., and a pH in the range of about 2 to about 10. In varying embodiments, the one or more bioactives encapsulated into the lipid membrane microcapsule are chemically stable for at least 5 days, e.g., at least about 6, 7, 8, 9, 10, 14, 21 or more, days, e.g., at a temperature in the range of about 4° C. to about 45° C., e.g., about 4° C. to about 30° C., in an isotonic solution and a pH in the range of about 6-8. In varying embodiments, the lipid membrane microcapsule releases less than 25%, e.g., less than 20%, 15%, 10%, 5%, or less, of the encapsulated bioactive in a gastric acidic environment or simulated gastric acid environment.

In varying embodiments, the lipid membrane microcapsules can have a targeting moiety attached or bound to the external surface, e.g., that specifically binds to an antigen or ligand of interest (e.g., a tumor associated antigen). For example, an immunoglobulin or another non-immunoglobulin antigen binding molecule can be attached to the external surface of the lipid membrane microcapsule. In some embodiments, the composition of the lipid membrane microcapsule (e.g., the type and/or species of cell) is selected for targeting ligands naturally present on the external surface. For example, yeast cell wall components contain beta-glucans that have natural affinity to bind various immunological components within the intestine and modulate immunological responses. Specific types or species of cells used as microcapsules can be selected based on their native components on the external surface which facilitate the targeted delivery of bioactives to desired cells and/or tissues, e.g., specific sections of the intestine. As a further example, mannoproteins on yeast cell walls have affinity to bind pathogenic bacteria and prevent their colonization in the gut. This affinity can be combined with the loading and delivery of antimicrobial compounds which may significantly enhance the activity of targeting pathogens and prevent their colonization. Illustrative examples of antimicrobial compounds include without limitation antimicrobial peptides such as defensins, cathelicidins (e.g., LL-37), C-type lectins (such as the regenerating islet-derived protein (REG) family), ribonucleases (RNases) and S100 proteins (e.g., calprotectin). In a further example, affinity of inactive cells from the natural flora of skin to provide controlled delivery of products to the skin. Inactive microbial cells isolated from natural flora of skin can be used as an encapsulation carrier for the delivery of bioactives to skin. Illustrative examples of 'natural' resident skin flora include without limitation *Propionibacterium acnes, Staphylococcus epidermis, Staphylococcus aureus, Corynebacterium diphtheria, Corynebacterium jeikeium,* and *Pseudomonas aeruginosa.*

For agricultural applications, encapsulation of compounds of interest in inactivated *agrobacterium* cells will provide high affinity binding of the bacterial cells (inactivated) to plants. This approach finds use for targeted delivery of pesticides, herbicides, fungicides and fertilizers to specific sections of plants such as roots, leaves etc. It is well known that specific strains of *agrobacterium* have affinity to bind various sections of plant tissues. See, e.g., Ohyama, et al., *Plant Physiology* (1979) 63(2):382-387. Similarly other plant pathogens such as fungal pathogens may also be used in inactive form for high affinity binding to plant structures.

3. Methods of Loading Bioactive Agents into Lipid Membrane Microcapsules

Provided are methods for the highly efficient and rapid loading and encapsulation of bioactives in lipid membrane microcapsules. The lipid membrane microcapsules can be a cell, a naturally occurring entity (e.g., a whole inactivated cell, plant oleosome or milk fat or lipid globule), or a subcellular organelle as described above and herein.

In varying embodiments, the methods entail subjecting a lipid membrane microcapsule or a population of lipid membrane microcapsules to vacuum pressure in the presence of one or more bioactive agents. In varying embodiments, the lipid membrane microcapsule or a population of lipid membrane microcapsules are suspended in a solution that can be either aqueous or non-aqueous (e.g., 100% ethanol); isotonic, hypertonic or hypotonic to the microcapsule, and containing saturating levels of the bioactives to be loaded or encapsulated into the microcapsules. As appropriate, the vacuum pressure (e.g., negative pressure) can be at least about 3 Torr, e.g., at least about 4 Torr, 5 Torr, 6 Torr, 7 Torr, 8 Torr, 9 Torr, and is generally less than about 10 Torr. The microcapsules are subjected to vacuum pressure for a time period sufficient to successfully load one or more bioactives into the microcapsules. In varying embodiments, the lipid membrane microcapsule is subjected to vacuum pressure for less than about 30 minutes, e.g., less than about 25, 20, 15 or 10 minutes. In varying embodiments, the lipid membrane microcapsule is sealed in a container comprising at least about 50% of absolute vacuum levels, e.g., at least about 55%, 60%, 65%, 70%, 75%, 80%, 85% or 90% of absolute vacuum levels, e.g., at least about 91%, 92%, 93%, 94%, 95%, 96%, 97%, 98% or 99% of absolute vacuum levels.

The vacuum pressure applied is of a level such that the lipid membrane microcapsule or population of microcapsules remains substantially intact once the pressure is removed or withdrawn. That is, less than about 5% of the bioactive(s) loaded into the microcapsules are released over a period of time of 10-15 minutes under conditions of repeated washing with excess water and centrifugation.

In varying embodiments, the methods comprise first subjecting the lipid membrane microcapsule to vacuum pressure, and second subjecting the lipid membrane microcapsule to positive external pressure in the presence of one or more bioactive agents. In varying embodiments, the lipid membrane microcapsule or a population of lipid membrane microcapsules is suspended in a solution that can be either aqueous or non-aqueous (e.g., 100% ethanol); isotonic, hypertonic or hypotonic to the microcapsule, and containing saturating levels of the bioactives to be loaded or encapsulated into the microcapsules. When exposing the microcapsules to vacuum pressure followed by positive external pressure, the microcapsules can be exposed to lower vacuum pressure levels. In some embodiments, when subjecting the lipid membrane microcapsule to positive external pressure, the lipid membrane microcapsule is sealed in a container comprising at least about 50% of absolute vacuum levels, e.g., at least about 55%, 60%, 65%, 70%, 75%, 80%, 85% or 90% of absolute vacuum levels, e.g., at least about 91%, 92%, 93%, 94%, 95%, 96%, 97%, 98% or 99% of absolute vacuum levels. In some embodiments, the positive external pressure is at least about 30 MPa, e.g., at least about 35 MPa, 40 MPa, 45 MPa or 50 MPa. In varying embodiments, the lipid membrane microcapsule is subjected to positive external pressure for less than about 90 minutes, e.g., for less than about 80, 70, 60, 50, 40, 30, 20 or 10 minutes.

The one or more bioactives can be loaded or encapsulated into the microcapsules by application of one or more iterations of vacuum pressure (and optionally including positive external pressure). For example, in some embodiments, the lipid membrane microcapsules can be subjected to 2, 3, 4, 5, 6, 7, 8, 9, 10 or more, iterations of vacuum pressure (and optionally positive external pressure). In varying embodiments, additional bioactive is added between iterations or applications of vacuum pressure. In some embodiments, no additional bioactive is added between iterations or applications of vacuum pressure.

Generally, the loading of bioactive into the microcapsules does not comprise heating or is performed at ambient temperature. In varying embodiments, the loading is performed at a temperature of less than about 38° C., e.g., less than about 37° C., 36° C., 35° C., 34° C., 33° C., 32° C., 31° C., 30° C., 29° C., 28° C., 27° C., 26° C., 25° C., but higher than freezing temperature (higher than 0° C.). In some embodiments, the loading does not comprise plasmolysing the lipid membrane microcapsule. In some embodiments, the methods further comprise plasmolysing the lipid membrane microcapsule. In varying embodiments, the loaded lipid membrane microcapsule releases less than about 5% of the encapsulated compound. In varying embodiments, the loading efficiency of the bioactive is at least about 15%, e.g., at least about 20%, 25%, 30%, 35%, 40%, 45%, 50%, 55%, 60%, 65%, 70%, 75%, 80%, 85%, or more. In some embodiments, the lipid membrane microcapsule is subjected to positive external pressure for less than 10 minutes, and wherein the loading efficiency of the bioactive is at least about 20%, e.g., at least about 25%, 30%, 35%, 40%, 45%, 50%, 55%, 60%, 65%, or more.

4. Compositions

Further provided are compositions comprising the bioactive-loaded lipid membrane microcapsules described herein.

In varying embodiments, the compositions are edible by a mammal, e.g., a human. In varying embodiments, the edible composition is a beverage, a food (an infant food, a snack food), a nutraceutical, a compressed cake, a powder, a suspension, or a capsule. In some embodiments, the compositions comprise a pharmaceutical formulation comprising the lipid membrane microcapsules formulated for oral, rectal, vaginal, topically, intravenous, intralesional, intraperitoneal, and/or intradermal administration.

5. Methods of Treating Disease Conditions

Further provided are methods of preventing, reducing, ameliorating, mitigating and/or treating a disease condition in a mammal in need thereof, comprising administering to the mammal an effective amount of a lipid membrane microcapsule as described above and herein. In varying embodiments, the lipid membrane microcapsule is administered via a route selected from the group consisting of orally, rectally, vaginally, topically, intravenously, intraperitoneally, intradermally and intralesionally. In varying embodiments, the disease condition is selected from obesity, metabolic syndrome, Type II diabetes, cardiovascular diseases, cancer prevention and therapy, inflammatory diseases, gut inflammation (inflammatory bowel disease, Crohn's disease), and skin disorders (including atopic dermatitis, healing of burn and scars, skin-rejuvenation, inflammation, infection and wounds).

In one embodiment, provided are methods of preventing, reducing, ameliorating, mitigating and/or treating inflammation of the gut (e.g., irritable bowel syndrome, inflammatory bowel disease, or Crohn's disease) in an individual in need thereof, comprising administering to the individual an effective amount of a lipid membrane microcapsule co-loaded with curcurmin and catechin. In varying embodiments, the lipid membrane microcapsule is administered enterally, e.g., orally or rectally.

In varying embodiments, about 1 µg to about 100 grams microcapsules are administered. The microcapsules can be administered one or multiple times, as necessary or desired.

EXAMPLES

The following examples are offered to illustrate, but not to limit the claimed invention.

Example 1

Encapsulation Systems for Improving Chemical Stability of Encapsulants

In this example, chemically inactivated yeast, algal and bacterial cells are the encapsulation matrix for both hydrophobic and hydrophilic bioactives. The influence of cell wall structure and lipid composition of cells on encapsulation efficiency and stability of bioactives are determined. Encapsulation efficiency achieved using pressure assisted encapsulation approaches are compared with the conventional diffusion based encapsulation approach. Stability of cell encapsulated bioactives is compared with emulsion encapsulated hydrophobic bioactives and aqueous solution of hydrophilic bioactives respectively.

Materials and Methods

Selection of Bioactives:

Two hydrophilic aqueous soluble bioactives (fisetin and quercetin) and two hydrophobic aqueous insoluble bioactives (curcumin and beta-carotene) bioactives are selected as model systems. These bioactives are selected because of their significant nutraceutical and antioxidant properties and challenges (e.g., limited shelf life, degradation during processing and challenges in delivery, significant challenges in their oral delivery without encapsulation due to limited solubility, and/or pH instability of the selected bioactives) [14, 16, 75, 76].

Selection and Culturing of Yeast and Algal Cells to Influence Intracellular Lipid Content:

Increased lipid content both improves the relative encapsulation efficiency of hydrophobic bioactives and the oxidative stability of encapsulated bioactives. In this aim, three strains (*Saccharomyces cerevisiae, Candida utilis, Phaffia rhodozyma*) of yeast with high and low lipid content (high lipid ascomycete and *Saccharomyces cerevisiae* (low lipid)) are selected. Similarly, and two strains of algal cells are selected (*Chlorella minutissima* (UTEX 2341), *Chlorella sorokiniana* (UTEX 2805). The yeast and algal cells are cultured to achieve varying levels of lipid content by influencing the extracellular nutrients, e.g. in the case of algal cells, deprivation of nitrogen in extracellular media can shift the metabolism to generate lipids, with varying levels of nitrogen, intracellular lipid content is modulated. The intracellular lipids are extracted from freeze dried yeast and algal cells and measured using established gravimetric methods. To induce lipogenesis, 5 mL of the pre-culture are transferred into a 500 mL baffled conical flask with 95 mL of media A (50 g/L glucose, 1.5 g/L yeast extract, 0.5 g/L $NH_4Cl$, 7.0 g/L $KH_2PO_4$, 2.5 g/L $Na_2HPO_4.2H_2O$, 1.5 g/L $MgSO_4.7H_2O$, 0.08 g/L $FeCl_3.6H_2O$, 10.0 mg/L $ZnSO_4.7H_2O$, 0.07 mg/L $MnSO_4.H_2O$, 0.1 mg/L $CuSO_4$, 0.063 mg/L $Co(NO_3)_2$) and closed with a foam cap. To repress lipogenesis, 5 mL of the pre-culture are transferred into a 500 mL standard conical flask with 245 mL of media A and covered with aluminum foil. Cultures are incubated in a rotary shaking incubator at 30° C. and 250 rpm for 10 days.

Modification of Cell Wall of Yeast and Algal Cells:

By increasing the cellular permeability, the encapsulation efficiency within these cells can be significantly improved. However, it is possible that increased permeability of cells may also adversely affect the chemical stability of encapsulated bioactives due to increased diffusion of oxidative species. To modify the cell wall permeability, the selected strains of yeast and algal cells are treated with 250 mM concentration of EDTA and 100 mM DTT (Dithiothreitol) for 30 minutes at 4° C. The EDTA treatment has been selected as it influences the pectin-$Ca^{2+}$ crosslinks from the cell wall. The DTT treatment reduces the degree of disulfide crosslinking between cell-wall proteins [77]. The influence of chemical treatment on cell wall permeability is determined by a combination of a functional measurement and ultra-structural analysis. The functional measurement is based on measuring diffusion of fluorescently labeled dextran (500 Da; 2000 Da) in the control and treated cells by fluorescence spectroscopy and imaging [77]. The ultra-structural changes in cell wall structure resulting from chemical treatment are characterized by AFM imaging. For imaging of changes in cell walls with AFM imaging, yeast or algal cells are dried on a freshly cleaved mica and topographic images of cells (three independent preparations) are acquired and surface profile of the cells from these topographic images are quantified to determine the changes in cell wall ultrastructure [78].

Pressure Assisted Encapsulation of Bioactives in Inactivated Yeast and Algal Cells:

Prior to encapsulation of bioactives, selected strains of both yeast and algal cells are inactivated with a chemical treatment. Chemical inactivation of yeast or algal cells stops the metabolic processes while preserving the structure and chemical composition of the cells. To inactive the yeast or algal cells, the cells are treated with 35% ethanolic solution for 30 minutes. The concentration of ethanol is selected based on the results of the previous study [79].

Encapsulation of Bioactives into Inactivated Yeast or Algal Cells Via Vacuum Infusion.

Briefly, 1 gm of yeast or algal cells pellet is suspended in the 35% ethanolic solution of the selected bioactive compound. Hydrophobic (curcumin and retinol) or hydrophilic (quercetin and fisetin) bioactive compounds are readily soluble in 35% ethanolic solution. We have determined the % ethanol to achieve sufficient encapsulation of the selected encapsulated bioactive compounds using both the vacuum and high pressure assisted encapsulation process.

Yeast or algal cell samples suspended in the ethanolic solution with the bioactive compound are sealed in boilable vacuum bags (Prime Source) at 99% vacuum (Ultravac 250, Koch Equipment LLC). This commercially available vacuum sealing process provides adequate vacuum levels to improve encapsulation of the selected bioactives as demonstrated in our results. The sealed samples are covered with aluminum foil to prevent any photo-degradation of the bioactives and incubated at room temperature (25° C.) for 10 minutes. Samples are emptied into 50 mL centrifuge tubes, centrifuged at 2200 rpm for 10 minutes to pellet the cells and the pelleted cells are washed twice with ethanolic solution (35%) and then five times with excess water to remove unencapsulated bioactives.

Encapsulation of Bioactives into Inactivated Yeast or Algal Cells Via Low-Medium Pressure.

Yeast cells or algal cells suspended in 35% ethanolic solution of the selected bioactive compounds and sealed in 6×8 boilable vacuum bags (Prime Source) are subjected to pressure ranging between 35-100 MPa for 10 minutes (2 L Isostatic Food Press, Avure Technologies). The influence of pressure conditions (35, 70, 100 MPa) on encapsulation efficiency of the selected hydrophobic and hydrophilic bioactives are evaluated. Samples are emptied into 50 mL centrifuge tubes, centrifuged to pellet the cells (2200 rpm for 10 minutes) and the pelleted cells are washed twice with ethanolic solution (35%) and then five times with excess water to remove unencapsulated bioactives.

Encapsulation of Bioactives into Inactivated Yeast or Algal Cells Via Diffusion Process.

Briefly, yeast or algal samples in a 35% ethanolic solution of the selected bioactive compound are covered with a single layer of aluminum foil to prevent photolysis. Samples are then placed into a rotary incubator at 50° C. and 200 rpm for 24 hours. After removal from the incubator, cells are removed by centrifugation at 2000 rpm for 10 minutes. The supernatant is decanted to isolate the pelleted cells and the pelleted cells are washed as described above to remove unencapsulated bioactives.

Encapsulation Efficiency:

Cells are sonicated to disrupt the cellular structure. A methanol extraction is utilized to extract the encapsulated bioactives from the disrupted yeast or algal cells. 0.05 g of cells (wet basis) with encapsulated bioactives are sonicated to disrupt cellular structure and subsequently incubated with 1 mL methanol. Samples are then briefly vortexed and centrifuged at 14,000 rpm for 10 minutes. The concentration of bioactive compound dissolved in the organic phase is measured using UV-vis spectrophotometer. The peak absorbance wavelength for curcumin, retinol, fisetin and catechin is at 420 nm, 325 nm, 360 nm and 275 nm respectively. Measuring loading of these bioactive compounds in various emulsions and nanoparticles has been described [55, 57]. The encapsulation efficiency is determined as follows:

$$EE(\%) = \frac{C_E}{C_T} \times 100,$$

where $C_E$ is the mass of extracted bioactive from the cells after encapsulation and $C_T$ is the amount of bioactive initially added to the cells.

Determination of Oxidative Stability of the Encapsulated Bioactives:

Oxidative stability of the encapsulated bioactive compounds are measured under three different conditions: (a) spontaneous oxidation induced by oxygen; (b) metal ion induced oxidation; and (c) free radical induced oxidation. The results of cell encapsulated hydrophobic bioactives are compared with conventional oil in water emulsions stabilized by Tween 20. In the case of encapsulated hydrophilic bioactives, the results are compared with aqueous solution of the bioactives. For the oxidation induced by environmental oxygen, the cells with encapsulated bioactives are stored in the dark at various temperatures (5° C., 20° C. and 45° C.) and a decrease in concentration of the bioactives in these samples are measured as a function of storage time. For the metal ion induced oxidation, the cellular encapsulated bioactives and their respective controls are incubated with increasing concentration (35 to 500 micro molar) of $Fe^{2+}$ at the selected temperature (5° C., 20° C. and 45° C.) for a period of 2 weeks and a decrease in concentration of the bioactives in these samples is measured as a function of storage time. To simulate free radical induced oxidation, the encapsulated bioactives in cells and controls (both emulsion and aqueous suspension) are exposed to 5 mM concentration of AAPH (2,2'-azobis-2-methyl-propanimidamide, dihydrochloride), a water soluble peroxyl radical generator. This test simulates an accelerated oxidative stability test and has been previously used by us and others to evaluate the oxidative barrier properties of various encapsulation systems [40, 80-82]. Concentration of the bioactives is measured at 3 hour intervals over an incubation period of 96 hours.

Determination of the pH Stability of the Encapsulated Bioactives:

Stability of the bioactive compounds such as curcumin and quercetin is influenced by pH. This limits stability of the bioactives in food products and can also limit absorption in the intestine. The influence of selected pH levels (pH 4, 5, 6 and 7) on comparative stability of bio-encapsulated bioactives is determined with controls (conventional emulsions with curcumin) and aqueous solutions of hydrophilic bioactives such as quercetin. Concentration of the bioactive compounds as a function of incubation time at the selected pH conditions is measured.

Results

Bio-encapsulation Process:

We have developed an innovative bioencapsulation process that provides rapid and efficient infusion of bioactives in isolated cells and lipid bodies. In this process, yeast or algal cells incubated in a solution containing bioactive were subjected to a vacuum (97% vacuum) or mild-high hydrostatic pressure (35-100 MPa) for ~5-10 minutes. In this study, encapsulation efficiency of model hydrophobic (curcumin, retinol) and hydrophilic (fisetin—a flavonol) bioactive compounds achieved with the novel processing approach were measured. The results of these measurements were compared with the conventional process used for encapsulation of bioactive compounds in yeast cells.

The results in Tables 1-5 demonstrate that the herein described approach can achieve multifold higher encapsulation efficiency within 10 minutes of vacuum or high-pressure exposure compared to the conventional diffusion based process at atmospheric pressure. Furthermore, extended exposure of bioactive compounds to high temperature (50° C.) during the atmospheric pressure diffusion process may result in a significant degradation of these compounds. Similar encapsulation efficiency using pressure assisted encapsulation process technologies was also achieved with infusion of curcumin in algal cells.

TABLE 1

|  | Conventional Methods, 24 hours, 50° C. | Vacuum (5 minutes) | Mild Pressure (35 Mpa), 10 minutes |
|---|---|---|---|
| Curcumin | 18 | 66 | 68 |
| Retinol | 15 | 45 | 70 |
| Fisetin | 11 | 64 | 68 |

Comparative evaluation of encapsulation efficiency (percent ratio of encapsulated bioactive with respect to total bioactive in solution) of hydrophobic and hydrophilic bioactives in inactivated yeast with vacuum and mild pressure processing as compared to conventional method based on heating of the samples to facilitate diffusion.

TABLE 2

Encapsulation Using Saturated Solution of Curcumin Into Yeast

| Buffer | Method | Mass of Bioactive Added (mg) | Mass of Encapsulated Bioactive in Yeast (mg/g) | Encapsulation Efficiency (%) |
|---|---|---|---|---|
| 2% Tween 20 in 100 mM Tris Buffer, pH = 8 | Conventional Diffusion | 4.375 | 0.292 | 13.3 |
|  | Vacuum Infusion | 4.375 | 0.483 | 22.1 |
|  | HPP (200 MPa) | 4.375 | 0.415 | 19.0 |
| 100 mM PBS, pH = 6.5 | Conventional Diffusion | 1.1 | 0.064 | 11.6 |
|  | Vacuum Infusion | 1.1 | 0.305 | 55.4 |
|  | HPP (200 MPa) | 1.1 | 0.242 | 43.9 |

The buffer, initial mass of curcumin added, mass of curcumin encapsulated per mass of yeast and the encapsulation efficiencies from conventional diffusion compared to vacuum infusion and HPP are shown. The solutions (35% v/v ethanol) were saturated with bioactive, i.e., the maximum mass of curcumin within the solvent system without observable precipitation.

TABLE 3

Encapsulation Using Saturated Solution of Fisetin Into Yeast

| Buffer | Method | Mass of Bioactive Added (mg) | Mass of Encapsulated Bioactive in Yeast (mg/g) | Encapsulation Efficiency (%) |
|---|---|---|---|---|
| 2% Tween 20 in 100 mM Tris Buffer, pH = 8 | Conventional Diffusion | 7.875 | 2.31 | 58.7 |
|  | Vacuum Infusion | 7.875 | 3.18 | 80.7 |
|  | HPP (200 MPa) | 7.875 | 2.16 | 54.8 |
| 100 mM PBS, pH = 6.5 | Conventional Diffusion | 5.220 | 1.11 | 42.6 |
|  | Vacuum Infusion | 5.220 | 2.75 | 105.3 |
|  | HPP (200 MPa) | 5.220 | 2.59 | 99.3 |

The buffer, initial mass of fisetin added, mass of fisetin encapsulated per mass of yeast and the encapsulation efficiencies from conventional diffusion compared to vacuum infusion and HPP are shown. The solutions (35% v/v ethanol) were saturated with bioactive, i.e., the maximum mass of fisetin within the solvent system without observable precipitation.

TABLE 4

Encapsulation of Curcumin in Algae Cells Using Pressure Assisted Encapsulation

| Sample | Encapsulation Efficiency (%) | Mass of Encapsulated Bioactive in Algae (mg/g) |
|---|---|---|
| *Chlorella minutissima* | 92.1 | 0.184 |
| *Chlorella sorokiniana* | 88.8 | 0.355 |

Encapsulation efficiency of curcumin into algae after vacuum sealing. Cells were split into equal amounts and treated with 5% ethanol, one aliquot treated with curcumin and the other without curcumin. 100 mg and 50 mg of *C. minutissima* and *C. sorokiniana*, respectively, were used for both the control and treatment. The supernatant from the pelleted cells was collected and then measured at $\Lambda$ = 425 nm.

TABLE 5

| Sample | Conventional Diffusion Single Loading, Curcumin | Conventional Diffusion Single Loading, Fisetin | Vacuum Dual Loading, Curcumin | Vacuum Dual Loading, Fisetin |
|---|---|---|---|---|
| Mass of Bioactive Added (mg) | 0.625 | 0.500 | 0.625 | 0.500 |
| Mass of Encapsulated Bioactive in Yeast (mg/g) | 0.134 | 0.061 | 0.442 | 0.480 |
| Encapsulation Efficiency (%) | 21.5 | 12.2 | 70.8 | 96.0 |

Dual loading of curcumin and fisetin into yeast cells via vacuum infusion. The infusion was carried out as described herein with the exception that both curcumin and fisetin were added together into the infusion solution.

To further validate that the bioactives were encapsulated within cells, the localization of bioactives in yeast cells was imaged using fluorescence confocal microscopy. This imaging measurement was based on the endogenous fluorescence properties of the bioactive compounds. In our previous study, we have demonstrated that localization of bioactives in emulsion can be imaged based on endogenous contrast properties of the bioactive compounds [55-57]. The results of imaging measurements, including control yeast cells, are illustrated in FIGS. 1-7. These results clearly demonstrate that both the hydrophobic and hydrophilic bioactive compounds were encapsulated in yeast cells.

Overall, these results demonstrate an approach to effectively encapsulate both hydrophobic and hydrophilic bioactive compounds in yeast cells. It is important to note that using this approach, the concentration of bioactives per unit weight of cells can be significantly higher than those naturally present in plant materials and in other common encapsulation systems such as emulsions [44]. In summary, we have developed an innovative approach to encapsulate desired bioactives compounds using a cell-based bio-carrier system. It is also envisioned that multiple bioactive compounds can be simultaneously encapsulated with high efficiency in cell based bio-carriers using this innovative approach.

Figure 8:
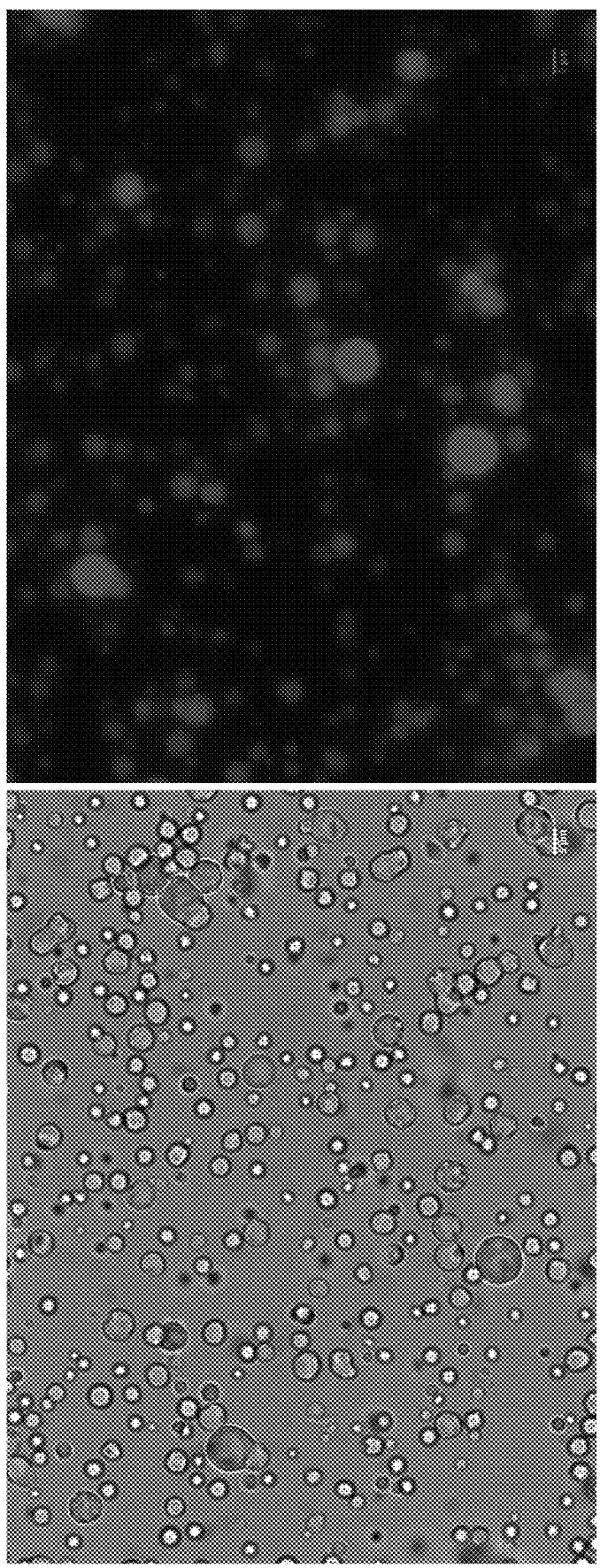
FIG. 8 illustrates encapsulation of a hydrophobic dye in milk fat globules. Scale bar represents a length of 5 μm.

Encapsulation of Hydrophobic Dye Molecules in Milk Fat Globules:

FIG. 8 shows the imaging data illustrating encapsulation of a hydrophobic Nile red dye in milk fat globules. For this study, Nile red dye in ethanol was added to the milk fat globules (final ethanol conc. of 10%) and the sample was incubated for 30 minutes. The ethanol was removed by vacuum after incubation. A homogenous distribution of fluorescence within oil droplets provide evidence that hydrophobic bioactives can be encapsulated in intact milk fat globules isolated from raw milk cream. See also, FIG. 9, which shows encapsulation of β-carotene into raw milk fat globules using vacuum infusion.

Figure 10:
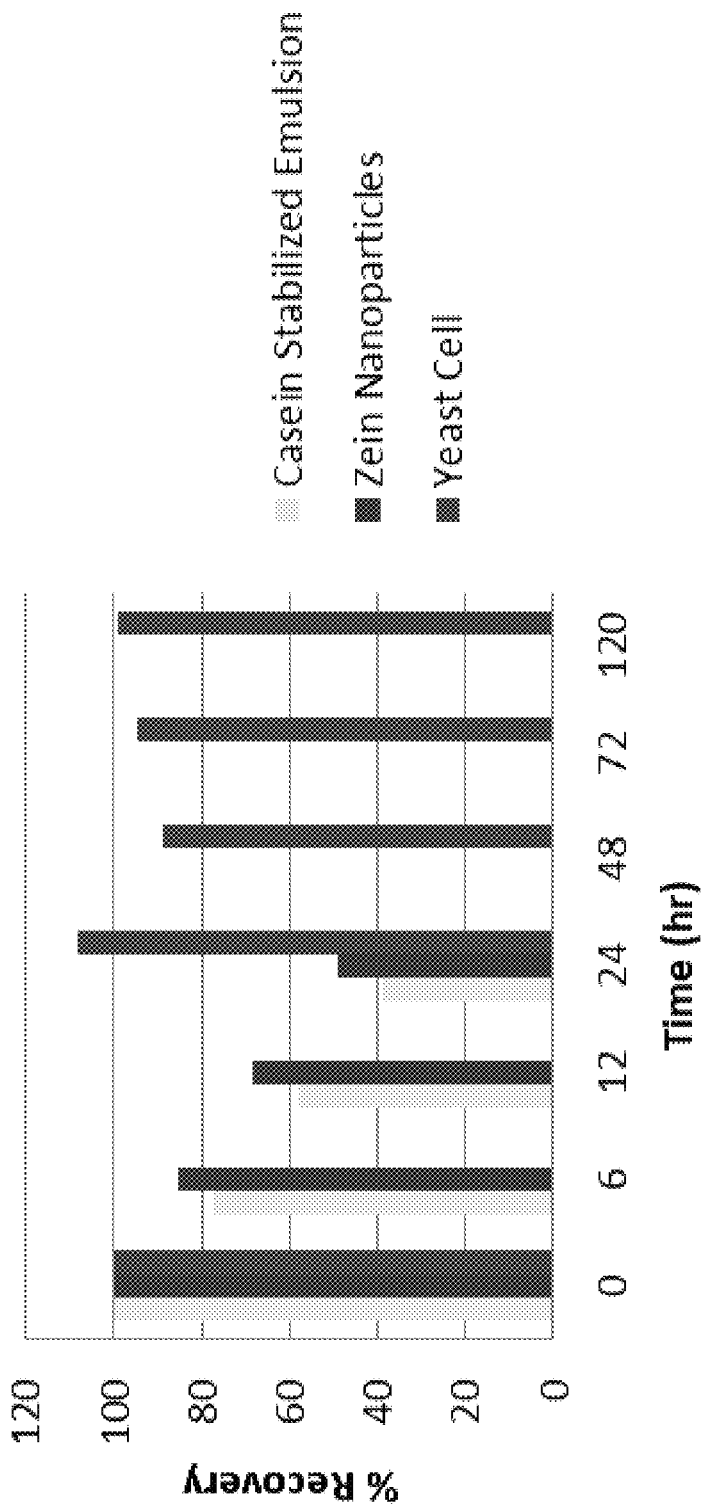
FIG. 10 illustrates stability of retinol encapsulated yeast cells as compared to retinol in emulsion and nanoparticles at room temperature. Stability of all-trans retinol encapsulated in casein stabilized emulsion, zein nanoparticles and yeast cells. The percent recovery of retinol in model systems after exposure to atmospheric oxygen is shown. Yeast cells provided the most stability to retinol, nearly 100% up to 5 days, while zein and casein systems have <10% after 4 days.
Figure 11:
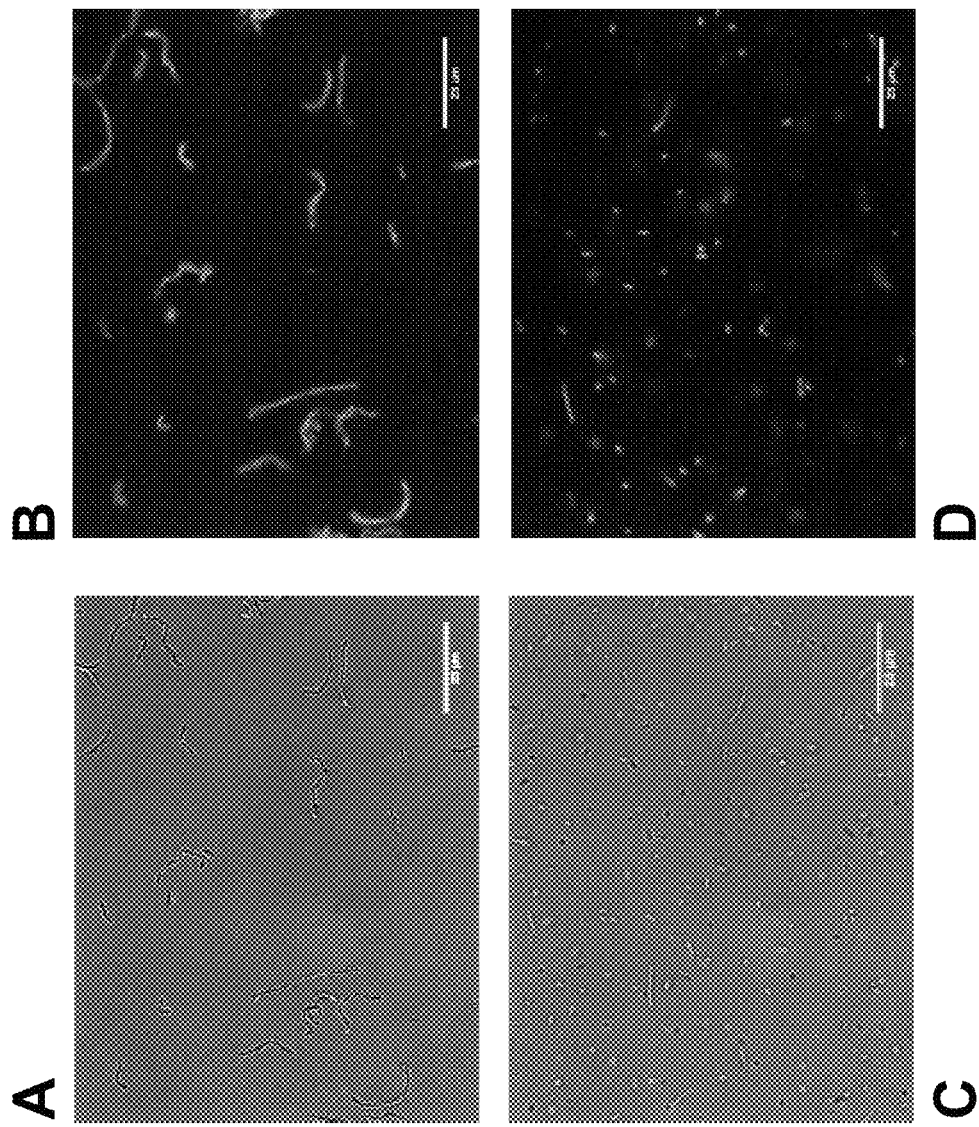
FIGS. 11A-D illustrate encapsulation of bioactives in bacteria (gram positive and gram negative). A) White light image of *Lactobacillus casei* (S1) with encapsulated curcumin. Exposure time: 100 ms; Magnification: 60×. B) Fluorescence image of *L. casei* (S1) with encapsulated curcumin acquired in the FITC channel (Ex/Em, 495/519). Exposure time: 100 ms; Magnification: 60×. C) White light image of *E. coli* (BL21) with encapsulated curcumin. Exposure time: 100 ms; Magnification: 60×. D) Fluorescence image of *E. coli* (BL21) with encapsulated curcumin acquired in the FITC channel (Ex/Em, 495/519). Exposure time: 100 ms; Magnification: 60×.
Figure 12:
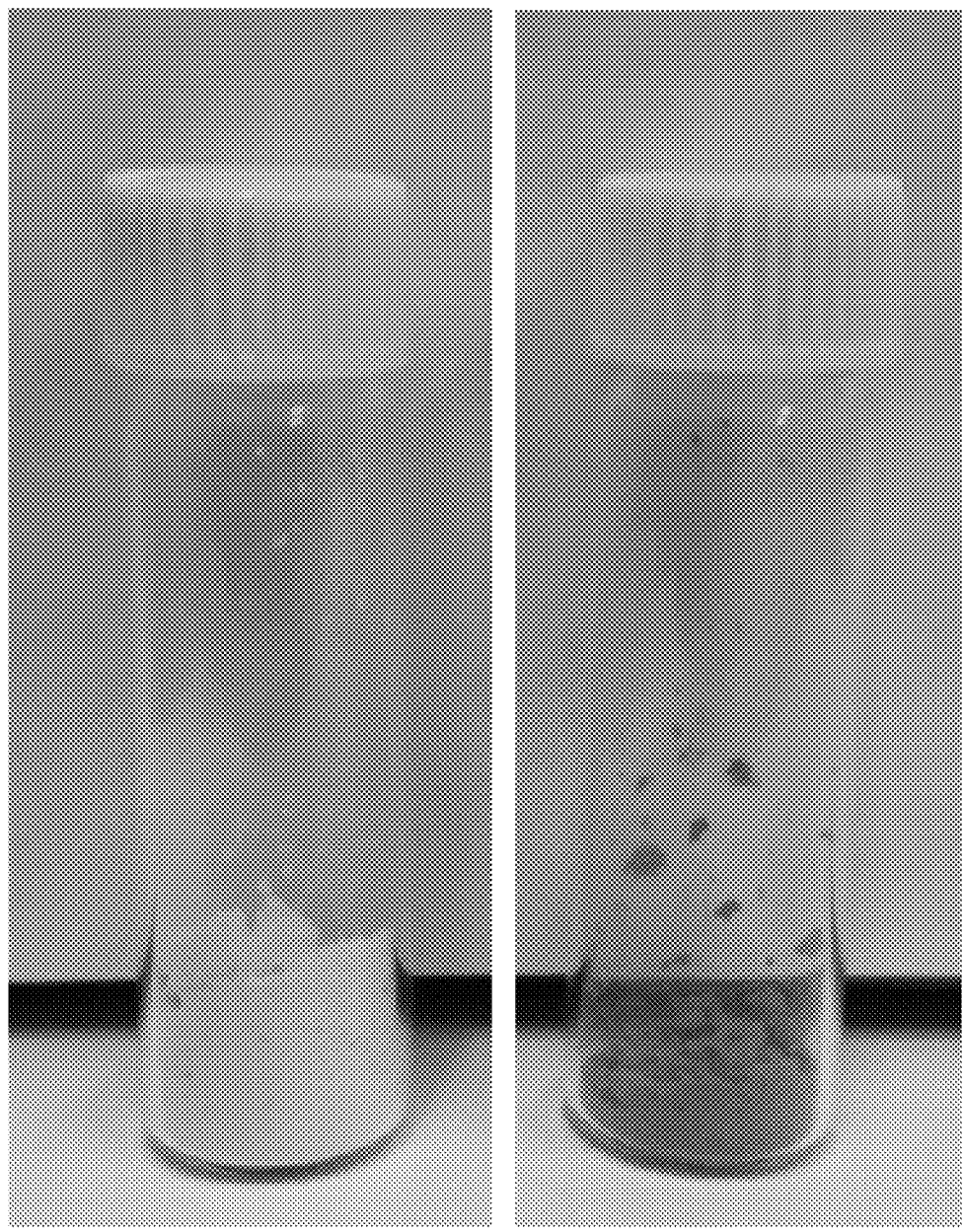
FIGS. 12A-B illustrates pressure enhanced encapsulation of grape skin extract in yeast cells. A. Control cells. B. Grape skin extract encapsulated in yeast cells. The grapeskin extract was provided from DDW (D.D. Williamson) The Color House (ddwcolor.com). Briefly, the grapeskin extract was dissolved in ultrapure water at a concentration of 30.77 mg/mL. Absolute ethanol was added to the grapeskin extract dissolved in water to yield a 35% (v/v) ethanol solution. Baker's yeast, *S. cerevisiae*, was washed and prepared as before. The yeast was added to the 35% ethanol (v/v) solution to yield a 20% (w/v) suspension, in which the final concentration of grapekskin extract to yeast was 100 mg/g. Samples were subjected to 99% vacuum for 5 seconds and then incubated, covered, for 10 minutes. The samples were washed five times (5×) with an excess of water and centrifuged at 2100× g for 5 minutes.

Storage Stability of Encapsulated Bioactives:

FIG. 10 and Table 6 demonstrate that retinol encapsulated within yeast cells was significantly more stable compared to retinol encapsulated within casein emulsion or zein nanoparticles. Retinol was selected as a model bioactive as it is highly susceptible to oxidative degradation at room temperature. These results validate that the bio-based encapsulation approach can improve the oxidative stability of retinol at room temperature.

TABLE 6

Thermal Stability Of Retinol In Cell Encapsulated Versus Emulsions

| Sample | 2% Tween 20 Emulsion | 2% Whey Protein Isolate Emulsion | 4% Ludox HS-30 Emulsion | Yeast Encapsulated Retinol |
|---|---|---|---|---|
| % Recovery | 62.5 | 65.4 | 58.7 | 100* |

*indicates value over 100%

Comparative percent recovery of retinol in emulsions and yeast after processing at 70° C. for 30 minutes. The retinol was extracted using methanol and the absorbance was measured at 325 nm.

TABLE 7

Influence of Intracellular Lipid Content on Yeast Species

| Sample | Commercial Baker's Yeast | S. Cerevisiae (68-115) Suppressed | S. Cerevisiae (68-115) Induced | L. starkeyi (51-55) Suppressed | L. starkeyi (51-55) Induced |
|---|---|---|---|---|---|
| Mass of Bioactive Added (mg) | 0.625 | 0.625 | 0.625 | 0.625 | 0.625 |
| Mass of Encapsulated Bioactive in Yeast (mg/g) | 0.392 | 0.238 | 0.260 | 0.466 | 0.559 |
| Encapsulation Efficiency (%) | 62.8 | 38.1 | 41.6 | 74.6 | 89.5 |

Encapsulation efficiency of curcumin into commercial and cultured yeasts. The data compare the encapsulation efficiency of curcumin into commercial baker's yeast and strains of S. cerevisiae and L. starkeyi cultured to either induce or suppress lipogenesis. All samples were vacuum infused using the previously described method with 35% ethanol. Samples were extracted with methanol and absorbance measurements taken at Λ = 425 nm.

To induce lipogeneis, 5 mL of the pre-culture are transferred into a 500 mL baffled conical flask with 95 mL of media A and closed with a foam cap. To repress lipogenesis, 5 mL of the pre-culture are transferred into a 500 mL standard conical flask with 245 mL of media A (50 g/L glucose, 1.5 g/L yeast extract, 0.5 g/L $NH_4Cl$, 7.0 g/L $KH_2PO_4$, 2.5 g/L $Na_2HPO_4.2H_2O$, 1.5 g/L $MgSO_4.7H_2O$, 0.08 g/L $FeCl_3.6H_2O$, 10.0 mg/L $ZnSO_4.7H_2O$, 0.07 mg/L $MnSO_4.H_2O$, 0.1 mg/L $CuSO_4$, 0.063 mg/L $Co(NO_3)_2$) and covered with aluminum foil. Cultures are incubated in a rotary shaking incubator at 30° C. and 250 rpm for 10 days.

TABLE 8

Encapsulation Efficiency of Curcurmin Into Bacteria

| | Curcumin | | Fisetin | |
|---|---|---|---|---|
| | E. coli (BL21) | L. casei (S1) | E. coli (BL21) | L. casei (S1) |
| Mass of Bioactive Added (mg) | 1.1 | 1.1 | 5.25 | 5.25 |
| Mass of Encapsulated Bioactive in Bacteria (mg/g) | 0.489 | 1.041 | 1.619 | 2.271 |
| Encapsulation Efficiency (%) | 44.4 | 94.6 | 30.8 | 43.2 |

The data compare the encapsulation efficiency of curcumin into strains of L. casei and E. coli. All samples were vacuum infused using the herein described method with 35% ethanol. Samples were extracted with methanol and dimethyl sulfoxide and absorbance measurements taken at Λ = 425 nm and 360 nm for curcumin and fisetin, respectively.

TABLE 9

Encapsulation Efficiency of Fisetin
Into Yeast Using Multiple Cycles

| Number of Cycles | Mass of Bioactive Added (mg) | Mass of Encapsulated Bioactive in Yeast (mg/g) | Encapsulated Efficiency (%) |
|---|---|---|---|
| 1 | 5.25 | 3.65 | 69.5 |
| 3 | 5.25 | 4.01 | 76.4 |

Encapsulation efficiency of fisetin into commercial yeasts using multiple cycles. The data set shows the mass of fisetin added, the mass of fisetin per gram yeast and the encapsulation efficiency. All samples were vacuum infused using the previously described method with 35% ethanol with one sample subjected to 99% vacuum three times (3x) with a 5 min incubation time between vacuum. Samples were extracted with dimethyl sulfoxide (DMSO) and absorbance measurements taken at $\Lambda$ = 365 nm. No additional fisetin was added between loading cycles.

REFERENCES FOR EXAMPLE 1

1. Emin, M. A., E. Mayer-Miebach, and H. P. Schuchmann, Retention of beta-carotene as a model substance for lipophilic phytochemicals during extrusion cooking. Lwt-Food Science and Technology, 2012. 48(2): p. 302-307.
2. Bricarello, D. A., M. J. Prada, and N. Nitin, Physical and chemical modifications of lipid structures to inhibit permeation of free radicals in a supported lipid membrane model. Soft Matter, 2012. 8(43): p. 11144-11151.
3. Chandler, P. N., C. Astete, and C. Sabliov, Stability of beta-carotene entrapped in Ca2+ crosslinked alginic acid nanoparticles. Agro Food Industry Hi-Tech, 2010. 21(5): p. 24-28.
4. Qian, C., et al., Inhibition of beta-carotene degradation in oil-in-water nanoemulsions: Influence of oil-soluble and water-soluble antioxidants. Food Chemistry, 2012. 135(3): p. 1036-1043.
5. Guzun-Cojocaru, T., et al., Oxidative stability of oil-in-water emulsions containing iron chelates: Transfer of iron from chelates to milk proteins at interface. Food Chemistry, 2011. 125(2): p. 326-333.
6. Guzun-Cojocaru, T., et al., Effect of iron chelates on oil-water interface, stabilized by milk proteins: The role of phosphate groups and pH. Prediction of iron transfer from aqueous phase toward fat globule surface by changes of interfacial properties. Food Hydrocolloids, 2010. 24(4): p. 364-373.
7. Alamed, J., D. J. McClements, and E. A. Decker, Influence of heat processing and calcium ions on the ability of EDTA to inhibit lipid oxidation in oil-in-water emulsions containing omega-3 fatty acids. Food Chemistry, 2006. 95(4): p. 585-590.
8. Choe, E. and D. B. Min, Mechanisms of Antioxidants in the Oxidation of Foods. Comprehensive Reviews in Food Science and Food Safety, 2009. 8(4): p. 345-358.
9. Bou, R., et al., Effect of different antioxidants on lycopene degradation in oil-in-water emulsions. European Journal of Lipid Science and Technology, 2011. 113(6): p. 724-729.
10. Jacobsen, C., et al., Antioxidant strategies for preventing oxidative flavour deterioration of foods enriched with n-3 polyunsaturated lipids: a comparative evaluation. Trends in Food Science & Technology, 2008. 19(2): p. 76-93.
11. Charoen, R., et al., Influence of interfacial composition on oxidative stability of oil-in-water emulsions stabilized by biopolymer emulsifiers. Food Chemistry, 2012. 131(4): p. 1340-1346.
12. Meynier, A., et al., n-3 fatty acid enriched eggs and production of egg yolk powders: An increased risk of lipid oxidation? Food Chemistry, 2014. 153: p. 94-100.
13. Gomez-Estaca, J., et al., Oxidative stability, volatile components and polycyclic aromatic hydrocarbons of cold-smoked sardine (*Sardina pilchardus*) and dolphinfish (*Coryphaena hippurus*). Lwt-Food Science and Technology, 2011. 44(6): p. 1517-1524.
14. Pedrosa, Z. V., et al., alpha-Tocopherol, retinol and ascorbic acid degradation during the processing and storage of shrimp food. Ciencia E Agrotecnologia, 2011. 35(2): p. 404-409.
15. Silva, L., et al., Oxidative stability of olive oil after food processing and comparison with other vegetable oils. Food Chemistry, 2010. 121(4): p. 1177-1187.
16. Bustos, R., et al., Oxidative stability of carotenoid pigments and polyunsaturated fatty acids in microparticulate diets containing krill oil for nutrition of marine fish larvae. Journal of Food Engineering, 2003. 56(2-3): p. 289-293.
17. Cheftel, J. C., Emerging Risks Related to Food Technology. Advances in Food Protection: Focus on Food Safety and Defense, 2011: p. 223-254.
18. Eriksson, M., I. Strid, and P. A. Hansson, Waste of organic and conventional meat and dairy products-A case study from Swedish retail. Resources Conservation and Recycling, 2014. 83: p. 44-52.
19. Pushkala, R., K. R. Parvathy, and N. Srividya, Chitosan powder coating, a novel simple technique for enhancement of shelf life quality of carrot shreds stored in macro perforated LDPE packs. Innovative Food Science & Emerging Technologies, 2012. 16: p. 11-20.
20. Taoukis, P. S., Commercialization of time-temperature integrators for foods. Case Studies in Novel Food Processing Technologies: Innovations in Processing, Packaging, and Predictive Modelling, 2010(197): p. 351-366.
21. Fukumoto, L. R. and G. Mazza, Assessing antioxidant and prooxidant activities of phenolic compounds. Journal of Agricultural and Food Chemistry, 2000. 48(8): p. 3597-3604.
22. Botterweck, A. A. M., et al., Intake of butylated hydroxyanisole and butylated hydroxytoluene and stomach cancer risk: Results from analyses in the Netherlands cohort study. Food and Chemical Toxicology, 2000. 38(7): p. 599-605.
23. Bothwell, T. H. and A. P. MacPhail, The potential role of NaFeEDTA as an iron fortificant. International Journal for Vitamin and Nutrition Research, 2004. 74(6): p. 421-434.
24. Kaya-Celiker, H. and K. Mallikarjunan, Better Nutrients and Therapeutics Delivery in Food Through Nanotechnology. Food Engineering Reviews, 2012. 4(2): p. 114-123.
25. McClements, D. J., et al., Structural Design Principles for Delivery of Bioactive Components in Nutraceuticals and Functional Foods. Critical Reviews in Food Science and Nutrition, 2009. 49(6): p. 577-606.
26. Sagalowicz, L. and M. E. Leser, Delivery systems for liquid food products. Current Opinion in Colloid & Interface Science, 2010. 15(1-2): p. 61-72.
27. Taneja, A. and H. Singh, Challenges for the Delivery of Long-Chain n-3 Fatty Acids in Functional Foods, in Annual Review of Food Science and Technology, Vol 3, M. P. Doyle and T. R. Klaenhammer, Editors. 2012. p. 105-123.
28. Coupland, J. N. and D. J. McClements, Lipid oxidation in food emulsions. Trends in Food Science & Technology, 1996. 7(3): p. 83-91.

29. Gasperlin, M., et al., Effect of colloidal carriers on ascorbyl palmitate stability. European Journal of Pharmaceutical Sciences, 2003. 19(4): p. 181-189.
30. Kanner, J., Metals and food oxidation, in Oxidation in Foods and Beverages and Antioxidant Applications, Vol 1: Understanding Mechanisms of Oxidation and Antioxidant Activity, E. A. Decker, R. J. Elias, and D. J. McClements, Editors. 2011. p. 36-56.
31. Lee, J. and E. A. Decker, Effects of Metal Chelator, Sodium Azide, and Superoxide Dismutase on the Oxidative Stability in Riboflavin-Photosensitized Oil-in-Water Emulsion Systems. Journal of Agricultural and Food Chemistry, 2011. 59(11): p. 6271-6276.
32. Nitin, N., R. V. Tikekar, and A. Johnson, Real-time measurement of oxygen transport across an oil-water emulsion interface. Journal of Food Engineering, 2011. 103(1): p. 14-20.
33. Tikekar, R. V., A. Johnson, and N. Nitin, Fluorescence imaging and spectroscopy for real-time, in-situ characterization of interactions of free radicals with oil-in-water emulsions. Food Research International, 2011. 44(1): p. 139-145.
34. Decker, E. A., J. R. Mancuso, and D. J. McClements, Iron-accelerated cumene hydroperoxide decomposition in hexadecane and trilaurin emulsions. Journal of Agricultural and Food Chemistry, 2000. 48(2): p. 213-219.
35. Jacobsen, C. and A. M. Haahr, Emulsifier type, metal chelation and pH affect oxidative stability of n-3-enriched emulsions. European Journal of Lipid Science and Technology, 2008. 110(10): p. 949-961.
36. Lewis, R. S. and M. Kavdia, Free radical profiles in an encapsulated pancreatic cell matrix model. Annals of Biomedical Engineering, 2002. 30(5): p. 721-730.
37. Lichtenberg, D., E. Schnitzer, and I. Pinchuk, Peroxidation of liposomal lipids. European Biophysics Journal with Biophysics Letters, 2007. 36(4-5): p. 499-515.
38. Berton, C., et al., Oxidative stability of oil-in-water emulsions stabilised with protein or surfactant emulsifiers in various oxidation conditions. Food Chemistry, 2012. 131(4): p. 1360-1369.
39. Berton, C., et al., Contribution of the Interfacial Layer to the Protection of Emulsified Lipids against Oxidation. Journal of Agricultural and Food Chemistry, 2011. 59(9): p. 5052-5061.
40. Zhao, Y., et al., Enhancing the barrier properties of colloidosomes using silica nanoparticle aggregates. Journal of Food Engineering, 2013. 118(4): p. 421-425.
41. Shi, G. R., et al., Characterization of yeast cells as a microencapsulation wall material by Fourier-transform infrared spectroscopy. Vibrational Spectroscopy, 2010. 53(2): p. 289-295.
42. Shi, G. R., et al., Stabilization and encapsulation of photosensitive resveratrol within yeast cell. International Journal of Pharmaceutics, 2008. 349(1-2): p. 83-93.
43. Paramera, E. I., S. J. Konteles, and V. T. Karathanos, Stability and release properties of curcumin encapsulated in *Saccharomyces cerevisiae*, beta-cyclodextrin and modified starch. Food Chemistry, 2011. 125(3): p. 913-922.
44. Paramera, E. I., S. J. Konteles, and V. T. Karathanos, Microencapsulation of curcumin in cells of *Saccharomyces cerevisiae*. Food Chemistry, 2011. 125(3): p. 892-902.
45. Kapchie, V. N., et al., Evaluation of enzyme efficiency for soy oleosome isolation and ultrastructural aspects. Food Research International, 2010. 43(1): p. 241-247.
46. Iwanaga, D., et al., Stabilization of soybean oil bodies using protective pectin coatings formed by electrostatic deposition. Journal of Agricultural and Food Chemistry, 2008. 56(6): p. 2240-2245.
47. Chen, B. C., et al., Physical and oxidative stability of pre-emulsified oil bodies extracted from soybeans. Food Chemistry, 2012. 132(3): p. 1514-1520.
48. Kapchie, V. N., et al., Oxidative stability of soybean oil in oleosomes as affected by pH and iron. Food Chemistry, 2013. 141(3): p. 2286-2293.
49. Kapchie, V. N., et al., Enzyme-assisted aqueous extraction of oleosomes from Soybeans (Glycine max). Journal of Agricultural and Food Chemistry, 2008. 56(5): p. 1766-1771.
50. Millichip, M., et al., Purification and characterization of oil-bodies (oleosomes) and oil-body boundary proteins (oleosins) from the developing cotyledons of sunflower (*Helianthus annuus* L). Biochemical Journal, 1996. 314: p. 333-337.
51. Beisson, F., et al., Large scale purification of an almond oleosin using an organic solvent procedure. Plant Physiology and Biochemistry, 2001. 39(7-8): p. 623-630.
52. Le, T. T., et al., Distribution and isolation of milk fat globule membrane proteins during dairy processing as revealed by proteomic analysis. International Dairy Journal, 2013. 32(2): p. 110-120.
53. Spitsberg, V. L., Bovine milk fat globule membrane as a potential nutraceutical. Journal of Dairy Science, 2005. 88(7): p. 2289-2294.
54. Singh, H., The milk fat globule membrane—A biophysical system for food applications. Current Opinion in Colloid & Interface Science, 2006. 11(2-3): p. 154-163.
55. Pan, Y., R. V. Tikekar, and N. Nitin, Effect of antioxidant properties of lecithin emulsifier on oxidative stability of encapsulated bioactive compounds. International Journal of Pharmaceutics, 2013. 450(1-2): p. 129-137.
56. Shah, N., et al., Distribution of curcumin within colloidal nanoparticles and its impact on stability and release kinetics of curcumin. Abstracts of Papers of the American Chemical Society, 2013. 245.
57. Tikekar, R. V., Y. J. Pan, and N. Nitin, Fate of curcumin encapsulated in silica nanoparticle stabilized Pickering emulsion during storage and simulated digestion. Food Research International, 2013. 51(1): p. 370-377.
58. Figueroa-Gonzalez, I., et al., Probiotics and prebiotics—perspectives and challenges. Journal of the Science of Food and Agriculture, 2011. 91(8): p. 1341-1348.
59. Ageitos, J. M., et al., Oily yeasts as oleaginous cell factories. Applied Microbiology and Biotechnology, 2011. 90(4): p. 1219-1227.
60. Frankel, E. N., et al., Oxidative stability of fish and algae oils containing long-chain polyunsaturated fatty acids in bulk and in oil-in-water emulsions. Journal of Agricultural and Food Chemistry, 2002. 50(7): p. 2094-2099.
61. Abe, K., H. Hattori, and M. Hirano, Accumulation and antioxidant activity of secondary carotenoids in the aerial microalga *Coelastrella striolata* var. *multistriata*. Food Chemistry, 2007. 100(2): p. 656-661.
62. Lange, N. and A. Steinbuchel, beta-Carotene production by *Saccharomyces cerevisiae* with regard to plasmid stability and culture media. Applied Microbiology and Biotechnology, 2011. 91(6): p. 1611-1622.
63. Storebakken, T., et al., Stability of astaxanthin from red yeast, *Xanthophyllomyces dendrorhous*, during feed processing: effects of enzymatic cell wall disruption and extrusion temperature. Aquaculture, 2004. 231(1-4): p. 489-500.

64. Charlwood, J., et al., Use of proteomic methodology for the characterization of human milk fat globular membrane proteins. Analytical Biochemistry, 2002. 301(2): p. 314-324.
65. Zhang, H., et al., Milk protein and fat play different roles in affecting the bioavailability and the antioxidant activity of jujube juice phenolics in rats. Molecular Nutrition & Food Research, 2012. 56(10): p. 1511-1519.
66. Lindmark-Mansson, H. and B. Akesson, Antioxidative factors in milk. British Journal of Nutrition, 2000. 84: p. S103-S110.
67. Fisk, I. D., et al., Aroma encapsulation and aroma delivery by oil body suspensions derived from sunflower seeds (*Helianthus annus*). European Food Research and Technology, 2011. 232(5): p. 905-910.
68. Lehner, A., F. Corbineau, and C. Bailly, Changes in lipid status and glass properties in cotyledons of developing sunflower seeds. Plant and Cell Physiology, 2006. 47(7): p. 818-828.
69. Nantiyakul, N., et al., Phytochemical Composition of Oryza sativa (Rice) Bran Oil Bodies in Crude and Purified Isolates. Journal of the American Oil Chemists Society, 2012. 89(10): p. 1867-1872.
70. Bengmark, S., M. D. Mesa, and A. Gil, Plant-derived health—the effects of turmeric and curcuminoids. Nutricion Hospitalaria, 2009. 24(3): p. 273-281.
71. Nair, S., et al., Micronutrient antioxidants in gastric mucosa and serum in patients with gastritis and gastric ulcer—Does *Helicobacter pylori* infection affect the mucosal levels? Journal of Clinical Gastroenterology, 2000. 30(4): p. 381-385.
72. Ribeiro, D., et al., Inhibition of LOX by flavonoids: a structure-activity relationship study. European Journal of Medicinal Chemistry, 2014. 72: p. 137-145.
73. Leonarduzzi, G., et al., Design and Development of Nanovehicle-Based Delivery Systems for Preventive or Therapeutic Supplementation with Flavonoids. Current Medicinal Chemistry, 2010. 17(1): p. 74-95.
74. Lin, Q. L., B. Akesson, and B. Bergenstahl, Effect of colloidal structures on the stability of five flavonoids with different hydrophilicity. Food Hydrocolloids, 2008. 22(4): p. 700-705.
75. Sun, M., et al., Advances in nanotechnology-based delivery systems for curcumin. Nanomedicine, 2012. 7(7): p. 1085-1100.
76. Cermak, R., et al., In vitro degradation of the flavonol quercetin and of quercetin glycosides in the porcine hindgut. Archives of Animal Nutrition, 2006. 60(2): p. 180-189.
77. Denobel, J. G., et al., Increased Cell-Wall Porosity in *Saccharomyces-Cerevisiae* after Treatment with Dithiothreitol or Edta. Journal of General Microbiology, 1989. 135: p. 2077-2084.
78. da Silva, A. and O. Teschke, Dynamics of the antimicrobial peptide PGLa action on *Escherichia coli* monitored by atomic force microscopy. World Journal of Microbiology & Biotechnology, 2005. 21(6-7): p. 1103-1110.
79. Flores, M. V., C. E. Voget, and R. J. J. Ertola, Permeabilization of Yeast-Cells (*Kluyveromyces*) with Organic-Solvents. Enzyme and Microbial Technology, 1994. 16(4): p. 340-346.
80. Tikekar, R. V. and N. Nitin, Distribution of Encapsulated Materials in Colloidal Particles and Its Impact on Oxidative Stability of Encapsulated Materials. Langmuir, 2012. 28(25): p. 9233-9243.
81. Tikekar, R. V. and N. Nitin, Effect of physical state (solid vs. liquid) of lipid core on the rate of transport of oxygen and free radicals in solid lipid nanoparticles and emulsion. Soft Matter, 2011. 7(18): p. 8149-8157.
82. Mosca, M., et al., Role of emulsifier layer, antioxidants and radical initiators in the oxidation of olive oil-in-water emulsions. Food Research International, 2013. 50(1): p. 377-383.
83. Zemke-White, W. L., K. D. Clements, and P. J. Harris, Acid lysis of macroalgae by marine herbivorous fishes: effects of acid pH on cell wall porosity. Journal of Experimental Marine Biology and Ecology, 2000. 245(1): p. 57-68.
84. Klis, F. M., et al., Dynamics of cell wall structure in *Saccharomyces cerevisiae*. Fems Microbiology Reviews, 2002. 26(3): p. 239-256.
85. D'Andrea, S., et al., Selective one-step extraction of *Arabidopsis thaliana* seed oleosins using organic solvents. Journal of Agricultural and Food Chemistry, 2007. 55(24): p. 10008-10015.
86. Tikekar, R. V., et al., "Click chemistry" based conjugation of lipophilic curcumin to hydrophilic epsilon-polylysine for enhanced functionality. Food Research International, 2013. 54(1): p. 44-47.
87. Luo, Z., R. V. Tikekar, and N. Nitin, Click Chemistry Approach for Imaging Intracellular and Intratissue Distribution of Curcumin and Its Nanoscale Carrier. Bioconjugate Chemistry, 2014. 25(1): p. 32-42.

Example 2

Bio-Encapsulation of Functional Ingredients to Modulate Gut Microbiota and Obesity-Associated Inflammation This example provides innovations in the areas of encapsulation process technology, imaging and delivery of bioactives using food grade encapsulation materials to enhance delivery of dietary bioactives to the colon tissue. This enhanced delivery of bioactives to the colon reduces systemic inflammation.

The methods utilize process technology for encapsulation of both hydrophobic and hydrophilic compounds in inactivated yeast and algal cells with high encapsulation efficiency, as demonstrated in our data herein (over 60% of the saturation concentration of the bioactives).

The methods further utilize cell-based carriers (e.g., yeast, bacterial and algal cells) for efficient delivery of bioactives to the colon tissue. Yeast is an established probiotic [20-22] and live yeast cells can survive both gastric and intestinal digestion. To deliver bioactives to the colon, we have selected the cell-based carriers. Without this food grade cell-based carrier, many bioactives, such as catechins, can be absorbed in the small intestine and some bioactive compounds, such as curcumin, can be degraded by hydrolysis in the small intestine or may not be bioavailable due to its limited solubility in aqueous environment. These food grade carriers are distinct from the pharmaceutical approaches based on synthetic polymers or non-food grade materials.

Further provided are food grade carriers for simultaneous delivery of multiple bioactives to distinct sections of the intestine. By altering permeability of cell walls, delivery efficiency in both small intestine and colon can be controlled. Simultaneous delivery of multiple bioactives finds use for evaluating synergistic interaction among the bioactive compounds.

Evidence of Synergistic Interactions Between Bioactives:

A considerable body of research has shown that foods containing the flavan-3-ols, catechin and epicatechin and their oligomers and polymers, such as green tea, cocoa and grape seeds, significantly reduce risk factors for metabolic diseases. The phenolic compound, curcumin, also prevents obesity-related metabolic diseases. The absorption of curcumin, and oligomers and polymers of (epi-)catechin or their derivatives, such as gallates, is negligible. Both flavan-3-ols and curcumin [73] also have known strong antimicrobial properties. The simultaneous delivery of catechin and curcumin using the bio-encapsulation approach described herein alters the microbiome in a manner different from each alone, enhances the reduction of inflammation, and increases improvements in gut health. Catechin and curcumin in vitro had a synergistic effect on reducing growth of human colon adenocarcinoma (HCT 15 and HCT 116) cells and human larynx cancer (Hep G-2) cells [74]. The combination of epigallocatechin-3-gallate (EGCG), curcumin and lovastatin was also more effective earlier against esophageal cancer cell lines TE-8 and SKGT-4 than individual compounds [75]. These studies and other studies of the increased efficacy of curcumin and phenolic compound cocktails against cancer cell lines imply that combinations have different mechanisms of actions and may act differently or be more effective in changing the profile of the gut microbiota than individual compounds.

Bio-Encapsulation Systems:

Yeast and algal cells were selected as model encapsulating systems because these cells can withstand gastric digestion, as demonstrated in our preliminary data, and has a known pre-biotic effect in animals [76, 77]. Several strains of yeast and algae have GRAS status and can be easily grown without extensive resources. Prior work by others [78-80] have relied on diffusion based methods typically combined with extended heating (over 24 hours) for encapsulation of hydrophobic flavor and some bioactive compounds in yeast, vegetal or tissue matrices. However, mass transfer into yeast employing only simple diffusion is slow, on the time scale of days and has very low encapsulation efficiency (<15%) [79, 80]. Furthermore, the heating process can itself damage the bioactive compounds. To address these limitations, we have used vacuum or a combination of vacuum and high pressure to infuse extracts or nutraceutical compounds in both inactivated yeast and algal cells. Our method utilizing vacuum or a combination of vacuum and high pressure requires only 5-10 minutes with significantly higher encapsulation efficiencies compared to diffusion-limited techniques. Yeast and algal cells are highly stable under both thermal and pressure forces at levels typically used in food processing operations.

One of the limitations with both direct supplementation and synthetic encapsulation systems is the lack of biological complexity. Biological complexity present in plant cells and other biological systems facilitates the delivery of significant amounts of bioactives to the colon tissue, including gut microbes. It is widely believed that delivery of bioactives and vitamins through diet is significantly more effective that direct supplementation. Delivery of bioactives to the colon significantly influences circulating and tissue inflammation through several pathways.

Materials and Methods

Yeast and Algal Strains and Chemical Treatment for Inactivation of Cells and Changes in Permeability of Cell Wall:

A strain of yeast (*Saccharomyces cerevisiae*) and a strain of algae cells (*Chlorella minutissima* (UTEX 2341) are selected. These selected strains have a GRAS status and can be readily incorporated into diverse food products. We seek to influence the cell wall permeability of the selected strains of yeast and algal cells to achieve high levels of encapsulation efficiency while restricting the release of bioactives in gastric and small intestinal environment. To inactive the yeast and algal cells, the cells are treated with 35% ethanolic solution for 30 minutes. To modify the cell wall permeability, the selected strains of yeast and algal cells are treated with 250 mM concentration of EDTA and 100 mM DTT (Dithiothreitol) for 30 minutes at 4° C. The EDTA treatment has been selected as it influences the pectin-$Ca^{2+}$ crosslinks. The DTT treatment reduces the degree of disulfide cross-linking between cell-wall proteins [89]. The influence of chemical treatment on cell wall permeability is determined by a combination of a functional measurement and ultra-structural analysis. The functional measurement is based on measuring diffusion of fluorescently labeled dextran (500 Da; 2000 Da) in the control and treated cells by fluorescence spectroscopy and imaging [89]. The ultra-structural changes in cell wall structure resulting from chemical treatment are characterized by AFM imaging. For imaging of changes in cell walls with AFM imaging, yeast or algal cells are dried on a freshly cleaved mica, topographic images of cells (three independent preparations) are acquired, and surface profile of the cells from these topographic images are quantified to determine the changes in cell wall ultrastructure [90].

Encapsulation Efficiency of Bioactives in Inactivated Native and Modified Strains of Yeast and Algal Cells:

Yeast cells or algal cells with and without cell wall modification are suspended in 35% ethanolic solution of the selected bioactive compounds and sealed in 6×8 boilable vacuum bags (Prime Source). The sample is subjected to a pressure of 35 MPa for 10 minutes (2 L Isostatic Food Press, Avure Technologies). Samples are emptied into 50 mL centrifuge tubes, centrifuged to pellet the cells (2200 rpm for 10 minutes) and the pelleted cells are washed twice with ethanolic solution (35%) and then five times with excess water to remove un-encapsulated bioactives. The encapsulation efficiency of the selected bioactive compounds in both the cell wall modified and unmodified strains of the yeast and algal cells are quantified. The cells are lysed using sonication and the encapsulated bioactives are extracted using 100% methanol. The concentration of bioactives in methanolic extract is measured using UV-Vis. analysis.

In-Vitro Simulated Digestion and Release of Encapsulated Bioactives:

The influence of cell wall permeability on the release of encapsulated bioactives during simulated gastric and intestinal digestion is determined; and formulation of yeast or algal cells which can persist during simulated digestion and has a potential to deliver significant payload of bioactives to the colon tissue is identified. Based on these results, one yeast formulation and one algal formulation per bioactive compound is evaluated using an in-vivo model system.

Simulated Gastric Digestion to Measure Release of Encapsulated Bioactives:

Simulated gastric fluid (SGF) is prepared according to the procedure described in our recent study [91]. For these measurements, both native and cell wall modified yeast or algal cells with encapsulated bioactives are used. The control samples for these measurements also includes native yeast or algal cells without any encapsulated bioactives. This digestion mixture is placed in a dialysis cassette. The dialysis cassette is placed in 1 L of SGF and maintained at a temperature of 37±2° C. The solution from the dialysis cassette is sampled (200 µL) every 30 minutes and encapsulated bioactives retained within the sample is measured.

The concentration of extracted curcumin and catechin is measured using UV-Vis measurement at 425 nm and 275 nm and normalized with respect to the absorbance measurements from the control samples.

Simulated Intestinal Digestion to Measure Release of Encapsulated Bioactives:

Simulated intestinal fluid (SIF) is prepared according to the procedure described in our recent study [91]. For these measurements, both native and cell wall modified yeast or algal cells with encapsulated bioactives are used. Samples are incubated at 37° C. in simulated intestinal fluid. To measure the release of encapsulated bioactives, samples are collected at 0.5, 1, 2 and 3 hours respectively. The samples (200 µL) at each time point are centrifuged (2000 rpm) at 25° C. for 30 minutes to separate the cells from the supernatant. The concentration of released bioactive compounds in the supernatant is measured using the UV-Vis spectroscopy as described above.

Acute In-Vivo Study:

Formulations for the delivery of the bioactive compounds to the colon tissue are identified. The yeast and algae cells that show satisfactory resistance to in vitro simulated gastric and intestinal digestion are fed to mice to confirm their release in the cecum and colon. Mice are fed AIN-93M diet for 1 week prior to feeding test materials. Seven groups (catechin+algal, catechin+yeast, curcumin+algal, curcumin+yeast, curcumin, catechin, control) of five male C57BL/6 mice each are gavaged with 100 mg cells containing bioactives suspended in 200 µl saline (or equivalent amount of free bioactives or 0.5% methylcellulose in saline in case of control) and continued on AIN93M diet. To image delivery of curcumin to the colon, curcumin monoalkyne analog is used in this study. The dose does not exceed 1% of liquid suspension of body weight. Mice are killed after 8 hrs under isoflurane anesthesia and blood, small intestine, cecum, colon, cecum content, colon content, epidydimal adipose, and liver collected. Imaging and/or extraction is used to determine curcumin uptake in organ sections. HPLC of plasma is used to determine curcumin and (epi-)catechin levels in blood. Methanolic extracts of organs are used to determine (epi-)catechin by HPLC since oligomers and higher condensed catechins are not absorbed. Comparisons between the two treatments are made by Students t test, with significance level at $p<0.05$.

LC-MS and Data Analysis:

The tissue homogenates and blood samples are analyzed using LC-MS. For analytical measurements, the tissue lysates and blood plasma are centrifuged to pellet proteins at 4° C. at 12,000×g for 30 minutes and the supernatant is passed through 0.22 um membranes prior to reverse phase UHPLC-ESI-MS/MS analysis. General HPLC-ESI-MS/MS conditions for analysis of curcumin are as follows: Column: Agilent Poroshell 120 EC-C18 (2.7 um, 4.6×50 mm), Flow rate 0.4 ml/min; Solvents: A 5% acetonitrile adjusted to pH 3.5 and solvent B: 100% acetonitrile. Gradient: 0-0.2 min, 15% B; 0.2-10 min, 15-45% B; 10-14 min, 45-52% B; 14-16 min, 100% B. Re-equilibration for 5 min with 100% A [83]. Results obtained from these measurements are compared with imaging results. Similarly, LC-MS analytical procedure is adapted based on the results of a previous study [92].

Imaging and Data Analysis:

After completion of the in-vivo incubation time periods, the isolated tissue samples are imaged using a combination of widefield and high resolution imaging. Widefield imaging provides a spatial map on a macroscale to characterize distribution of curcumin monoalkyne in a colon tissue. To address challenges with autofluorescence of tissues in widefield imaging, the proposed research uses combination of NIR (near infra-red) fluorophores and spectral imaging methods to improve discrimination of fluorescence signal from background autofluorescence. After widefield imaging, tissues are analyzed using high resolution confocal imaging. For high resolution imaging, intestinal tissues are transversely sectioned (200 micron thick sections) and stained using a "click chemistry" reaction between the monoalkyne curcumin and azide modified fluorophores (Alexa 647-Azide). Imaging technologies, including click chemistry based in-situ imaging of tissues has been employed [93-97].

Results

Figure 13:
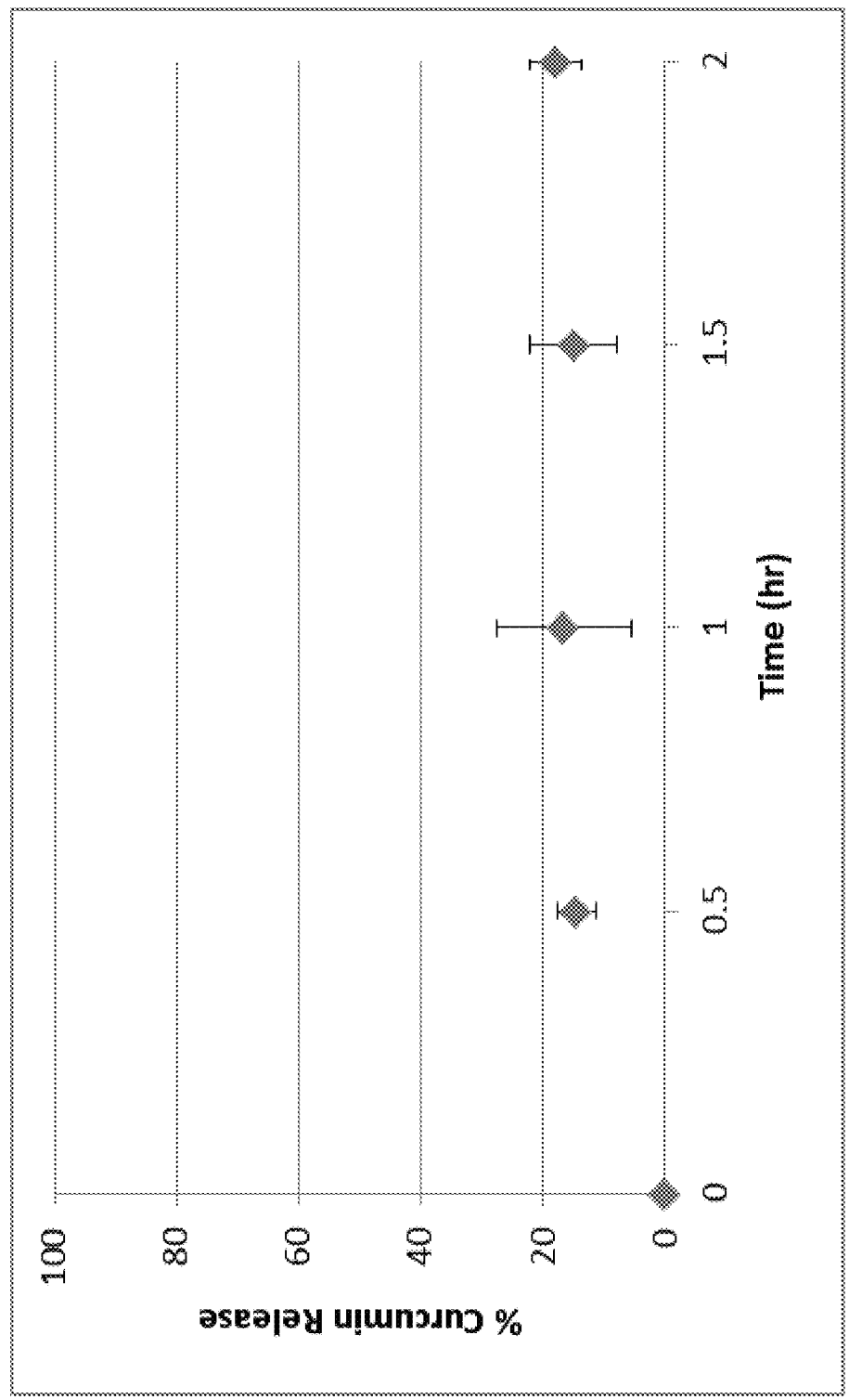
FIG. 13 illustrate percent release of curcumin from yeast during simulated gastric digestion (pH=1.2). The sample was maintained in a dialysis bag (MWCO=3.5 k) in 1 L of simulated gastric fluid (SGF) at 37° C. and 250 rpm for the duration of the digestion. Yeast cells were extracted with methanol at each time point and the absorbance measured at $\lambda$=425 nm.

In-Vitro Digestion Measurements:

To effectively deliver bioactive compounds to the colon tissue, it is desired that the encapsulated compounds are not released during gastric and early stages of intestinal digestion. In our preliminary study, we investigated the potential of yeast cells to prevent release of encapsulated compound during gastric digestion. The results in FIG. 13 demonstrate that less than 20% of the encapsulated curcumin was released from the yeast cells after 2 hours of simulated gastric digestion. In addition, visual analysis of yeast cells demonstrated no significant change in cell morphology after 2 hours of simulated gastric digestion. These results are in agreement with the observations that yeast cells have probiotic function and live yeast cells can survive both gastric and intestinal digestion [20-22].

REFERENCES FOR EXAMPLE 2

1. Kim, M. S., et al., Strict vegetarian diet improves the risk factors associated with metabolic diseases by modulating gut microbiota and reducing intestinal inflammation. Environmental Microbiology Reports, 2013. 5(5): p. 765-775.
2. Burcelin, R., et al., Intestinal microbiota and novel therapeutic perspectives for the treatment of metabolic diseases. M S-Medecine Sciences, 2013. 29(8-9): p. 800-806.
3. Vajro, P., G. Paolella, and A. Fasano, Microbiota and Gut-Liver Axis: Their Influences on Obesity and Obesity-Related Liver Disease. Journal of Pediatric Gastroenterology and Nutrition, 2013. 56(5): p. 461-468.
4. Delzenne, N. M., A. M. Neyrinck, and P. D. Cani, Gut microbiota and metabolic disorders: how prebiotic can work? British Journal of Nutrition, 2013. 109: p. S81-S85.
5. Vipperla, K. and S. J. O'Keefe, The Microbiota and Its Metabolites in Colonic Mucosal Health and Cancer Risk. Nutrition in Clinical Practice, 2012. 27(5): p. 624-635.
6. Hullar, M. A. J. and J. W. Lampe, The Gut Microbiome and Obesity. Obesity Treatment and Prevention: New Directions, 2012. 73: p. 67-79.
7. De Bandt, J. P., A. J. Waligora-Dupriet, and M. J. Butel, Intestinal microbiota in inflammation and insulin resistance: relevance to humans. Current Opinion in Clinical Nutrition and Metabolic Care, 2011. 14(4): p. 334-340.
8. Moreira, A. P. B., et al., Influence of a high-fat diet on gut microbiota, intestinal permeability and metabolic endotoxaemia. British Journal of Nutrition, 2012. 108(5): p. 801-809.
9. Nakamura, Y. K. and S. T. Omaye, Metabolic diseases and pro- and prebiotics: Mechanistic insights. Nutrition & Metabolism, 2012. 9.
10. Laugerette, F., et al., Complex links between dietary lipids, endogenous endotoxins and metabolic inflammation. Biochimie, 2011. 93(1): p. 39-45.

11. Cani, P. D. and N. M. Delzenne, Involvement of the gut microbiota in the development of low grade inflammation associated with obesity: focus on this neglected partner. Acta Gastro-Enterologica Belgica, 2010. 73(2): p. 267-269.
12. Cani, P. D., et al., Role of gut microflora in the development of obesity and insulin resistance following high-fat diet feeding. Pathologie Biologie, 2008. 56(5): p. 305-309.
13. Neyrinck, A. M., et al., *Curcuma longa* Extract Associated with White Pepper Lessens High Fat Diet-Induced Inflammation in Subcutaneous Adipose Tissue. Plos One, 2013. 8(11).
14. Machado, J., et al., *Helicobacter Pylori* Infection: Curcumin Reduces Gastric Inflammation by Modulating Intestinal Microbiota? *Helicobacter*, 2012. 17: p. 97-97.
15. Bae, H., et al., Ascorbic acid, capsaicinoid, and flavonoid aglycone concentrations as a function of fruit maturity stage in greenhouse-grown peppers. Journal of Food Composition and Analysis, 2014. 33(2): p. 195-202.
16. Cermak, R., et al., The influence of postharvest processing and storage of foodstuffs on the bioavailability of flavonoids and phenolic acids. Molecular Nutrition & Food Research, 2009. 53: p. S184-S193.
17. Dekker, M. and R. Verkerk, Modelling the consequences of variability in food production chains on human health. Proceedings of the 3rd International Symposium on Applications of Modelling as an Innovative Technology in the Agri-Food Chain, 2005(674): p. 71-76.
18. Schweiggert, R. M., et al., Carotenoids are more bioavailable from papaya than from tomato and carrot in humans: a randomised cross-over study. British Journal of Nutrition, 2014. 111(3): p. 490-498.
19. Schweiggert, R. M., et al., Influence of chromoplast morphology on carotenoid bioaccessibility of carrot, mango, papaya, and tomato. Food Chemistry, 2012. 135 (4): p. 2736-2742.
20. Czerucka, D., T. Piche, and P. Rampal, Yeast as probiotics—*Saccharomyces boulardii*. Alimentary Pharmacology & Therapeutics, 2007. 26(6): p. 767-778.
21. Newbold, C. and A. Olvera-Ramirez, The use of yeast-based probiotics to meet new challenges in ruminant production. Journal of Animal Science, 2006. 84: p. 425-425.
22. Tiago, F. C. P., et al., Adhesion to the yeast cell surface as a mechanism for trapping pathogenic bacteria by *Saccharomyces* probiotics. Journal of Medical Microbiology, 2012. 61(9): p. 1194-1207.
23. Clearfield, M., et al., The "New Deadly Quartet" for Cardiovascular Disease in the 21st Century: Obesity, Metabolic Syndrome, Inflammation and Climate Change: How Does Statin Therapy Fit into this Equation? Current Atherosclerosis Reports, 2014. 16(1).
24. Rana, J. S., et al., Cardiovascular metabolic syndrome—an interplay of, obesity, inflammation, diabetes and coronary heart disease. Diabetes Obesity & Metabolism, 2007. 9(3): p. 218-232.
25. Axling, U., et al., Green tea powder and *Lactobacillus plantarum* affect gut microbiota, lipid metabolism and inflammation in high-fat fed C57BL/6J mice. Nutrition & Metabolism, 2012. 9.
26. Diamant, M., E. E. Blaak, and W. M. de Vos, Do nutrient-gut-microbiota interactions play a role in human obesity, insulin resistance and type 2 diabetes? Obesity Reviews, 2011. 12(4): p. 272-281.
27. Gu, Y. Y., et al., Dietary cocoa reduces metabolic endotoxemia and adipose tissue inflammation in high-fat fed mice. Journal of Nutritional Biochemistry, 2014. 25(4): p. 439-445.
28. Ji, Y., Y. Sakata, and P. Tso, Nutrient-induced inflammation in the intestine. Current Opinion in Clinical Nutrition and Metabolic Care, 2011. 14(4): p. 315-321.
29. Scholz, S. and G. Williamson, Interactions affecting the Bioavailability of dietary polyphenols in vivo. International Journal for Vitamin and Nutrition Research, 2007. 77(3): p. 224-235.
30. Silva, L., et al., Oxidative stability of olive oil after food processing and comparison with other vegetable oils. Food Chemistry, 2010. 121(4): p. 1177-1187.
31. Unnadkat, N. R. and R. J. Elias, Oxidative Stability of (−)-Epigallocatechin Gallate in the Presence of Thiols. Journal of Agricultural and Food Chemistry, 2012. 60(43): p. 10815-10821.
32. Jimenez, A. M., et al., Effect of industrial processing and storage on antioxidant activity of apricot (*Prunus armeniaca* v. *bulida*). European Food Research and Technology, 2008. 227(1): p. 125-134.
33. Pan, Y., R. V. Tikekar, and N. Nitin, Effect of antioxidant properties of lecithin emulsifier on oxidative stability of encapsulated bioactive compounds. International Journal of Pharmaceutics, 2013. 450(1-2): p. 129-137.
34. Jitoe-Masuda, A., A. Fujimoto, and T. Masuda, Curcumin: From Chemistry to Chemistry-Based Functions. Current Pharmaceutical Design, 2013. 19(11): p. 2084-2092.
35. Rachmawati, H., et al., Development of curcumin nanocrystal: Physical aspects. Journal of Pharmaceutical Sciences, 2013. 102(1): p. 204-214.
36. Bricarello, D. A., M. J. Prada, and N. Nitin, Physical and chemical modifications of lipid structures to inhibit permeation of free radicals in a supported lipid membrane model. Soft Matter, 2012. 8(43): p. 11144-11151.
37. Tikekar, R. V., A. Johnson, and N. Nitin, Real-time measurement of oxygen transport across an oil-water emulsion interface. Journal of Food Engineering, 2011. 103(1): p. 14-20.
38. Alasalvar, C., et al., Turkish tombul hazelnut (*Corylus avellana* L.). 2. Lipid characteristics and oxidative stability. Journal of Agricultural and Food Chemistry, 2003. 51(13): p. 3797-3805.
39. Yi, J., et al., The physicochemical stability and in vitro bioaccessibility of beta-carotene in oil-in-water sodium caseinate emulsions. Food Hydrocolloids, 2014. 35: p. 19-27.
40. Kapchie, V. N., et al., Oxidative stability of soybean oil in oleosomes as affected by pH and iron. Food Chemistry, 2013. 141(3): p. 2286-2293.
41. Qian, C., et al., Physical and chemical stability of beta-carotene-enriched nanoemulsions: Influence of pH, ionic strength, temperature, and emulsifier type. Food Chemistry, 2012. 132(3): p. 1221-1229.
42. Zhou, L. and R. J. Elias, Factors Influencing the Antioxidant and Pro-Oxidant Activity of Polyphenols in Oil-in-Water Emulsions. Journal of Agricultural and Food Chemistry, 2012. 60(11): p. 2906-2915.
43. Tikekar, R. V., A. Johnson, and N. Nitin, Fluorescence imaging and spectroscopy for real-time, in-situ characterization of interactions of free radicals with oil-in-water emulsions. Food Research International, 2011. 44(1): p. 139-145.

44. Choi, S. J., et al., Influence of Droplet Charge on the Chemical Stability of Citral in Oil-in-Water Emulsions. Journal of Food Science, 2010. 75(6): p. C536-C540.
45. Velasco, J., C. Dobarganes, and G. Marquez-Ruiz, Oxidative rancidity in foods and food quality. Chemical Deterioration and Physical Instability of Food and Beverages, 2010(186): p. 3-32.
46. Cercaci, L., et al., Phytosterol oxidation in oil-in-water emulsions and bulk oil. Food Chemistry, 2007. 102(1): p. 161-167.
47. Ahmed, K., et al., Nanoemulsion- and emulsion-based delivery systems for curcumin: Encapsulation and release properties. Food Chemistry, 2012. 132(2): p. 799-807.
48. Rich, G. T., et al., Solubilization of carotenoids from carrot juice and spinach in lipid phases: II. Modeling the duodenal environment. Lipids, 2003. 38(9): p. 947-956.
49. Brown, J., et al., TLR-signaling networks: an integration of adaptor molecules, kinases, and cross-talk. J Dent Res, 2011. 90(4): p. 417-27.
50. Creely, S. J., et al., Lipopolysaccharide activates an innate immune system response in human adipose tissue in obesity and type 2 diabetes. Am J Physiol Endocrinol Metab, 2007. 292(3): p. E740-7.
51. Nakarai, H., et al., Adipocyte-macrophage interaction may mediate LPS-induced low-grade inflammation: potential link with metabolic complications. Innate Immun, 2012. 18(1): p. 164-170.
52. Brun, P., et al., Increased intestinal permeability in obese mice: new evidence in the pathogenesis of nonalcoholic steatohepatitis. Am J Physiol Gastrointest Liver Physiol, 2007. 292(2): p. G518-25.
53. Neal, M. D., et al., Enterocyte TLR4 mediates phagocytosis and translocation of bacteria across the intestinal barrier. J Immunol, 2006. 176(5): p. 3070-9.
54. Dasu, M. R., et al., Increased toll-like receptor (TLR) activation and TLR ligands in recently diagnosed type 2 diabetic subjects. Diabetes Care, 2010. 33(4): p. 861-8.
55. Serino, M., et al., Intestinal microflora and metabolic diseases. Diabetes Metab, 2009. 35(4): p. 262-72.
56. Suzuki, T. and H. Hara, Role of flavonoids in intestinal tight junction regulation. J Nutr Biochem, 2011. 22(5): p. 401-8.
57. Kim, C. Y. and K. H. Kim, Curcumin prevents leptin-induced tight junction dysfunction in intestinal Caco-2 BBe cells. J Nutr Biochem, 2014. 25(1): p. 26-35.
58. Hervert-Hernandeza D., G. I., Dietary Polyphenols and Human Gut Microbiota: a Review. Food Reviews International, 2011. 27: p. 154-169.
59. Puupponen-Pimia R., A. A., Oksman-Caldentey K M, Myllarinen P, Saarela M, Mattila-Sandholm T, Poutanen K, Development of functional ingredients for gut health. Trends in Food Science & Technology, 2002. 13(1): p. 3-11.
60. Etxeberria, U., et al., Impact of Polyphenols and Polyphenol-Rich Dietary Sources on Gut Microbiota Composition. J Agric Food Chem, 2013. 61(40): p. 9517-9533.
61. Tzounis, X., et al., Flavanol monomer-induced changes to the human faecal microflora. Br J Nutr, 2008. 99(4): p. 782-92.
62. Pozuelo, M. J., et al., Grape antioxidant dietary fiber stimulates *Lactobacillus* growth in rat cecum. J Food Sci, 2012. 77(2): p. H59-62.
63. Yamakoshi J., T. S., Kikuchi M., Kubota Y., Konishi H., Mitsuoka T, Effect of Proanthocyanidin-Rich Extract from Grape Seeds on Human Fecal Flora and Fecal Odor. Microbial Ecology in Health and Disease, 2001. 13: p. 25-31.
64. Garrett, W. S. D., 2011 #122}, et al., Enterobacteriaceae act in concert with the gut microbiota to induce spontaneous and maternally transmitted colitis. Cell Host Microbe, 2010. 8(3): p. 292-300.
65. Delzenne, N. M., A. M. Neyrinck, and P. D. Cani, Modulation of the gut microbiota by nutrients with prebiotic properties: consequences for host health in the context of obesity and metabolic syndrome. Microb Cell Fact, 2011. 10 Suppl 1: p. S10.
66. Santacruz, A., et al., Gut microbiota composition is associated with body weight, weight gain and biochemical parameters in pregnant women. Br J Nutr, 2010. 104(1): p. 83-92.
67. Ley, R. E., et al., Microbial ecology: human gut microbes associated with obesity. Nature, 2006. 444 (7122): p. 1022-3.
68. Kimura, I., et al., The gut microbiota suppresses insulin-mediated fat accumulation via the short-chain fatty acid receptor GPR43. Nat Commun, 2013. 4: p. 1829.
69. Wang, Z., et al., Gut flora metabolism of phosphatidylcholine promotes cardiovascular disease. Nature, 2011. 472(7341): p. 57-63.
70. Li, F., et al., Microbiome remodelling leads to inhibition of intestinal farnesoid X receptor signalling and decreased obesity. Nat Commun, 2013. 4: p. 2384.
71. Backhed, F., et al., The gut microbiota as an environmental factor that regulates fat storage. Proc Natl Acad Sci USA, 2004. 101(44): p. 15718-23.
72. Sayin, S. I., et al., Gut microbiota regulates bile acid metabolism by reducing the levels of tauro-beta-muricholic acid, a naturally occurring FXR antagonist. Cell Metab, 2013. 17(2): p. 225-35.
73. Bhawana, et al., Curcumin Nanoparticles: Preparation, Characterization, and Antimicrobial Study. Journal of Agricultural and Food Chemistry, 2011. 59(5): p. 2056-2061.
74. Manikandan, R., et al., Synergistic anticancer activity of curcumin and catechin: An in vitro study using human cancer cell lines. Microscopy Research and Technique, 2012. 75(2): p. 112-116.
75. Ye, F., et al., Suppression of esophageal cancer cell growth using curcumin, (−)-epigallocatechin-3-gallate and lovastatin. World Journal of Gastroenterology, 2012. 18(2): p. 126-135.
76. Pinloche, E., et al., Use of a colon simulation technique to assess the effect of live yeast on fermentation parameters and microbiota of the colon of pig. Journal of Animal Science, 2012. 90: p. 353-355.
77. Jouany, J. P., et al., Effect of live yeast culture supplementation on apparent digestibility and rate of passage in horses fed a high-fiber or high-starch diet. Journal of Animal Science, 2008. 86(2): p. 339-347.
78. Paramera, E. I., S. J. Konteles, and V. T. Karathanos, Microencapsulation of curcumin in cells of *Saccharomyces cerevisiae*. Food Chemistry, 2011. 125(3): p. 892-902.
79. Paramera, E. I., S. J. Konteles, and V. T. Karathanos, Stability and release properties of curcumin encapsulated in *Saccharomyces cerevisiae*, beta-cyclodextrin and modified starch. Food Chemistry, 2011. 125(3): p. 913-922.
80. Shi, G. R., et al., Stabilization and encapsulation of photosensitive resveratrol within yeast cell. International Journal of Pharmaceutics, 2008. 349(1-2): p. 83-93.
81. Zhao, Y., N. Nitin, and R. V. Tikekar, Engineering of interfacial permeability in silica nanoparticles stabilized oil-in-water Pickering emulsion to control transport across emulsion interface. Abstracts of Papers of the American Chemical Society, 2013. 245.
82. Tikekar, R. V., et al., "Click chemistry" based conjugation of lipophilic curcumin to hydrophilic epsilon-polylysine for enhanced functionality. Food Research International, 2013. 54(1): p. 44-47.
83. Luo, Z., R. V. Tikekar, and N. Nitin, Click Chemistry Approach for Imaging Intracellular and Intratissue Distribution of Curcumin and Its Nanoscale Carrier. Bioconjugate Chemistry, 2014. 25(1): p. 32-42.
84. Ageitos, J. M., et al., Oily yeasts as oleaginous cell factories. Applied Microbiology and Biotechnology, 2011. 90(4): p. 1219-1227.
85. Frankel, E. N., et al., Oxidative stability of fish and algae oils containing long-chain polyunsaturated fatty acids in bulk and in oil-in-water emulsions. Journal of Agricultural and Food Chemistry, 2002. 50(7): p. 2094-2099.
86. Abe, K., H. Hattori, and M. Hirano, Accumulation and antioxidant activity of secondary carotenoids in the aerial microalga *Coelastrella striolata* var. *multistriata*. Food Chemistry, 2007. 100(2): p. 656-661.
87. Lange, N. and A. Steinbuchel, beta-Carotene production by *Saccharomyces cerevisiae* with regard to plasmid stability and culture media. Applied Microbiology and Biotechnology, 2011. 91(6): p. 1611-1622.
88. Storebakken, T., et al., Stability of astaxanthin from red yeast, *Xanthophyllomyces dendrorhous*, during feed processing: effects of enzymatic cell wall disruption and extrusion temperature. Aquaculture, 2004. 231(1-4): p. 489-500.
89. Denobel, J. G., et al., Increased Cell-Wall Porosity in *Saccharomyces-Cerevisiae* after Treatment with Dithiothreitol or Edta. Journal of General Microbiology, 1989. 135: p. 2077-2084.
90. da Silva, A. and O. Teschke, Dynamics of the antimicrobial peptide PGLa action on *Escherichia coli* monitored by atomic force microscopy. World Journal of Microbiology & Biotechnology, 2005. 21(6-7): p. 1103-1110.
91. Tikekar, R. V., Y. J. Pan, and N. Nitin, Fate of curcumin encapsulated in silica nanoparticle stabilized Pickering emulsion during storage and simulated digestion. Food Research International, 2013. 51(1): p. 370-377.
92. Chang, C. L. and R. T. Wu, Quantification of (+)-catechin and ( )-epicatechin in coconut water by LC-MS. Food Chemistry, 2011. 126(2): p. 710-717.
93. Luo, Z., et al., Optical molecular imaging approach for rapid assessment of response of individual cancer cells to chemotherapy. Journal of Biomedical Optics, 2012. 17(10).
94. Nitin, N., et al., Molecular imaging of glucose uptake in oral neoplasia following topical application of fluorescently labeled deoxy-glucose. International Journal of Cancer, 2009. 124(11): p. 2634-2642.
95. Nitin, N., D. J. Javier, and R. Richards-Kortum, Oligonucleotide-coated metallic nanoparticles as a flexible platform for molecular Imaging agents. Bioconjugate Chemistry, 2007. 18(6): p. 2090-2096.
96. Nitin, N., et al., Optical Molecular Imaging of Epidermal Growth Factor Receptor Expression to Improve Detection of Oral Neoplasia. Neoplasia, 2009. 11(6): p. 542-551.
97. Nitin, N., et al., Peptide-linked molecular beacons for efficient delivery and rapid mRNA detection in living cells. Nucleic Acids Research, 2004. 32(6).
98. Lih, F. L. and R. E. Levin, Relative Effectiveness of Yeast-Cell Wall Digesting Enzymes on *Yarrowia-Lipolytica*. Microbios, 1990. 63(255): p. 109-115.
99. Yuasa, H., et al., Application of acid-treated yeast cell wall (AYC) as a pharmaceutical additive. II: effects of curing on the medicine release from AYC-coated tablets. International Journal of Pharmaceutics, 2000. 209(1-2): p. 69-77.
100. Michel, G., et al., The cell wall polysaccharide metabolism of the brown alga *Ectocarpus siliculosus*. Insights into the evolution of extracellular matrix polysaccharides in Eukaryotes. New Phytologist, 2010. 188(1): p. 82-97.
101. Bartley, G. E., et al., Hypocholesterolemic effects of hydroxypropyl methylcellulose are mediated by altered gene expression in hepatic bile and cholesterol pathways of male hamsters. J Nutr, 2010. 140(7): p. 1255-60.
102. Kim, H., et al., HPMC supplementation reduces abdominal fat content, intestinal permeability, inflammation, and insulin resistance in diet-induced obese mice. Mol Nutr Food Res, 2012. 56(9): p. 1464-76.

Example 3

Fermentation Gut Bacteria Association with Microcapsules

*E. coli* (ATCC 8739) stained with SYBR Green dye was mixed with equal amounts of microcapsules (milk fat globules, oil emulsion or yeast cells) separately. The carriers were loaded with Nile Red dye in advance. After incubation of the *E. coli* with the microcapsules at 37° C. for 24 hours, fluorescence images of the mixtures were acquired. In contrast to the WPI emulsion based microcapsule interfaces, inactivated yeast cell and MFGM (milk fat globular membrane) carriers had significant interaction and binding affinity with the bacteria. Thus, yeast cells and MFGM provide a favorable delivery mechanism for bioactives to the colon (where the fermentation in the gut takes place). Furthermore, based on our data demonstrating encapsulation of bioactives in bacterial cells, bacterial cells also serve as carriers for the delivery of bioactives to the colon tissue. The results are depicted in FIG. 14. Similar binding was observed after incubation of the *E. coli* with the microcapsules at 37° C. for 5 minutes.

Example 4

High Affinity Binding of Yeast Microcarriers with Skin and Release of Compounds into Tissue Dye-loaded yeast cells were attached on porcine mouth mucosa tissue. Yeast cells were labeled with propidium iodide (PI) dye and applied on the surface of porcine oral cavity tissues. After incubations for corresponding time spans, residue was removed by multiple washings, e.g., with water. Significant fluorescence signals of attached yeast were detected after 30 min of incubation, with improved pixel intensity by extended topical administration time. The results are depicted in FIG. 15. The results show that yeast as a microcarrier has a strong binding affinity to mouth mucosa, which serves as a water-resistant and controlled-release delivery system without additional patch or gel material. This can enhance customer compliance and economic efficiency. Similar binding was observed after incubation of the yeast cell microcapsules with the porcine mouth mucosa for 5-10 minutes.

Dye-loaded yeast cells were attached on porcine skin. Yeast cells were labeled with PI, then topically incubated with porcine skin for 30 min. Fluorescence images were taken after rinsing off non-attached yeast cells on the tissue.

The results are depicted in FIG. 16. As depicted, the PI-labeled yeast cells attached to the skin surface after short incubation time, demonstrating that bioactive-loaded yeast cells serve as a local dermal delivery system. The dye-loaded yeast cells withstood multiple rinsing and locally released encapsulated bioactive chemicals into the porcine skin.

The Nile Red fluorescence signal contrast of porcine skin incubated with yeast encapsulation system and non-incubated porcine skin was evaluated. Yeast microcapsules were loaded with Nile Red dye and spread on porcine skin surface. After incubation at room temperature for 12 hours, fluorescence images were taken on the 20 μm-thick slice of tissue cross-section. The results are depicted in FIG. 17. Compared to natural fluorescence of pork skin, the yeast cells loaded with Nile Red dye elicited significantly augmented fluorescence signals demonstrating that Nile Red was effectively released from yeast cells, further permeated crossing the stratum corneum and reached the dermis layer. This encapsulation system thus provides an option for convenient, pain-free and efficient compound delivery, which can be self-administered and operate as an alternative to oral dosing or injections.

Figure 18A:
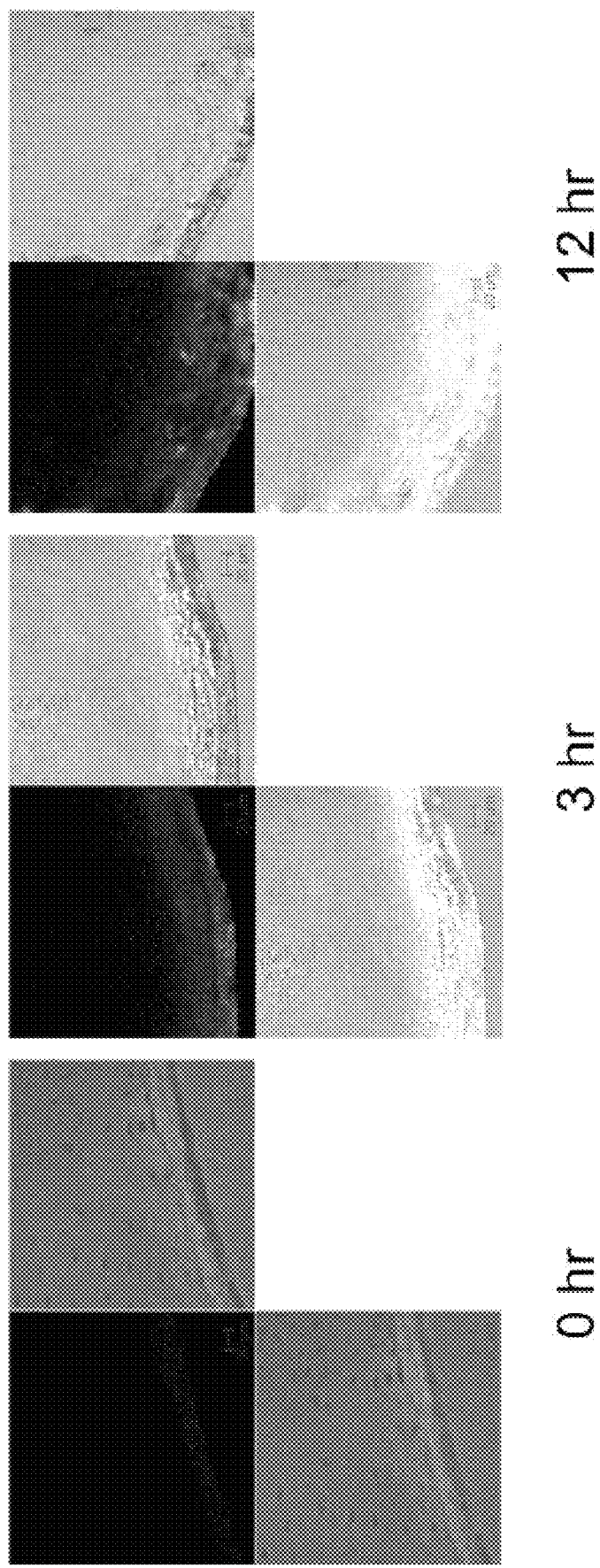
FIGS. 18A-B. (A) Curcumin release and diffusion in porcine mouth mucosa incubated with yeast cells encapsulating curcumin. (B) Curcumin signal intensity and diffusion length in porcine mouth mucosal tissues as a function of time.
Figure 18B:
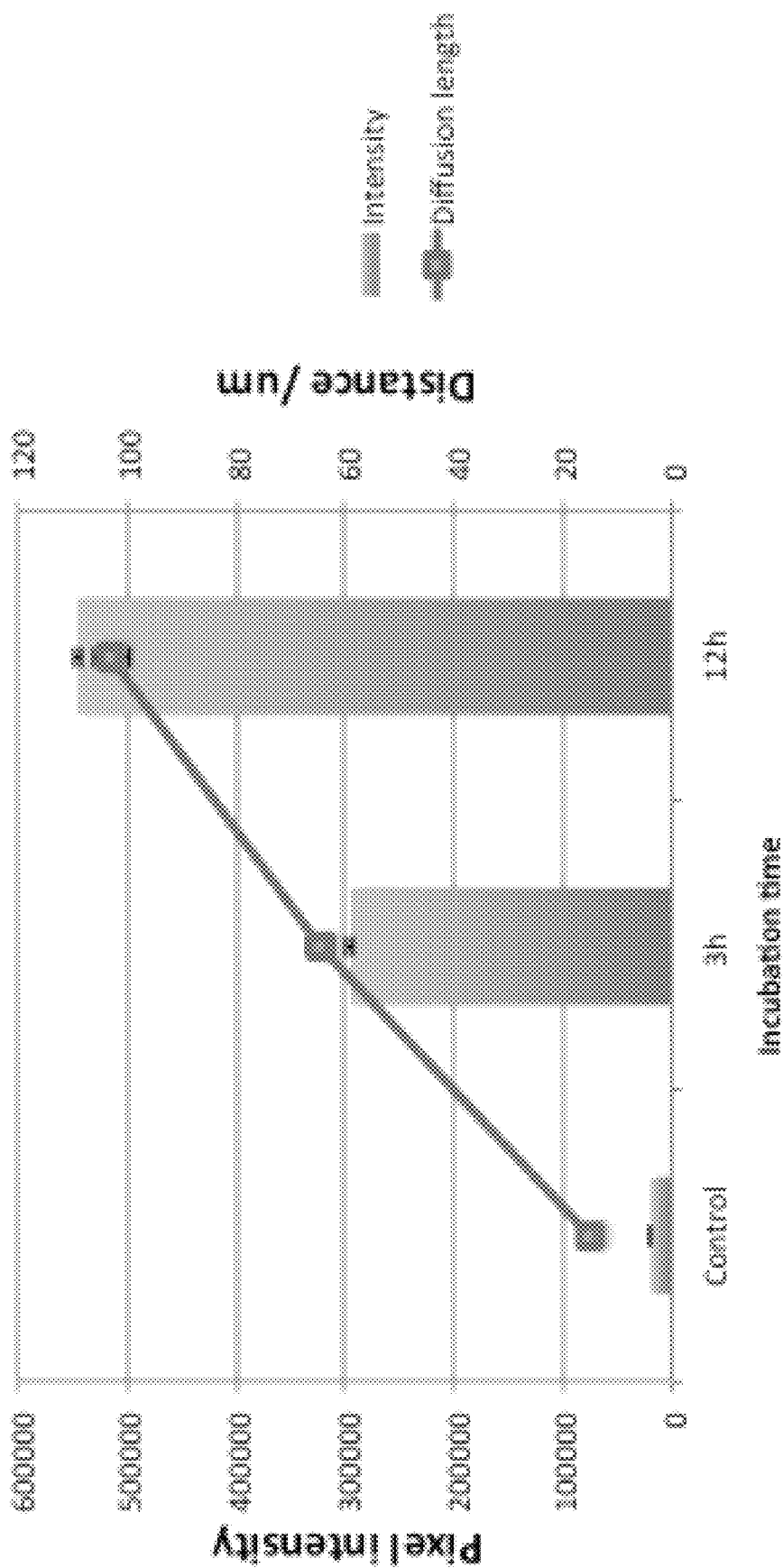

Curcumin release and diffusion in porcine mouth mucosa from yeast encapsulation system was evaluated. Yeast microcapsules loaded with curcumin were topically applied on the porcine oral cavity tissue. After incubations for corresponding time periods, curcumin permeation was detected by imaging the tissue cross-sections. Both integrated pixel intensity and penetration distance from skin top surface were calculated. The results are depicted in FIG. 18. Results indicate that curcumin diffused into mouth mucosa tissue with a strong time-dependent manner, while the compound remained intact after 12 h. Furthermore, the yeast carriers can be engineered to act as a programmable microcarrier system that can provide controlled or triggered release of bioactive components in oral mucosa. This engineering can be accomplished by physical, chemical and/or genetic modification of the cell wall and cytoplasmic composition of yeast cells including modification of their lipid content.

It is understood that the examples and embodiments described herein are for illustrative purposes only and that various modifications or changes in light thereof are suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of loading one or more bioactive agents into a lipid membrane microcapsule, comprising:
    subjecting the lipid membrane microcapsule in the presence of the one or more bioactive agents to a vacuum pressure of at least about 25% of absolute vacuum levels for a period of 30 minutes or less;
    wherein said bioactive agents enter an interior space of said microcapsule.

2. The method of claim 1, wherein the lipid membrane microcapsule is subjected to the one or more bioactive agents in a solution selected from the group consisting of an aqueous solution and a non-aqueous solution.

3. The method of claim 1, wherein said lipid membrane microcapsules are sealed in a container where the vacuum pressure (e.g., negative pressure) is in the range of at least about about 50% of absolute vacuum levels to at least about 99% absolute vacuum levels.

4. The method of claim 1, further comprising, after subjecting the lipid membrane microcapsule to vacuum pressure, subjecting the lipid membrane microcapsule to positive external pressure.

5. The method of claim 1, wherein the lipid membrane microcapsule is subjected to multiple iterations of vacuum pressure.

6. The method of claim 4, wherein the lipid membrane microcapsule is subjected to multiple iterations of vacuum pressure and positive external pressure.

7. The method of claim 5, wherein the bioactive lipid membrane microcapsule is subjected to additional bioactive between each iteration of vacuum pressure.

8. The method of claim 4, wherein the lipid membrane microcapsule is subjected to positive external pressure for less than 10 minutes.

9. The method of claim 1, wherein the lipid membrane microcapsule is a cell.

10. The method of claim 9, wherein the cell comprises a cell wall.

11. The method of claim 10, wherein the permeability of the cell or cell wall is modified.

12. The method of claim 1, wherein the lipid membrane microcapsule is a subcellular organelle of a cell or is from a subcellular organelle of a cell.

13. The method of claim 1, wherein the one or more bioactive agents are selected from the group consisting of a small organic compound, a peptide, a polypeptide, a polynucleotide, and a fatty acid.

14. The method of claim 13, wherein the one or more bioactive agents have a molecular weight in the range of about 10 Da to about 30 kDa.

15. The method of claim 1, wherein said one or more bioactive agent is selected from the group consisting of a hydrophobic bioactive, a hydrophilic bioactive, and a combination of at least one hydrophobic bioactive and at least one hydrophilic bioactive agent.

16. The method of claim 4, wherein said positive external pressure is in the range of about 30 MPa to about 50 MPa.

17. The method of claim 16, wherein the lipid membrane microcapsule is subjected to a vacuum pressure for less than 30 minutes and a positive external pressure for less than 90 minutes.

18. The method of claim 17, wherein the lipid membrane microcapsule is subjected to iterations of vacuum pressure and positive external pressure in the range between 2 and 10 iterations.

19. The method of claim 17, wherein the lipid membrane microcapsule is subjected to iterations of vacuum pressure of between about 3 Torr and about 10 Torr.

* * * * *